US006414148B1

(12) United States Patent
Thomas et al.

(10) Patent No.: US 6,414,148 B1
(45) Date of Patent: Jul. 2, 2002

(54) QUINAZOLINE DERIVATIVES AND PHARMACEUTICAL COMPOSITIONS CONTAINING THEM

(75) Inventors: Andrew Peter Thomas; Craig Johnstone; Edward Clayton; Elaine Sophie Elizabeth Stokes, all of Macclesfield (GB); Jean-Jacques Marcel Lohmann; Laurent Francois Andre Hennequin, both of Reims Cedex (FR)

(73) Assignees: Zeneca Limited, London (GB); Zeneca Pharma S.A., Cedex (FR)

( * ) Notice: Subject to any disclaimer, the term of this patent is extended or adjusted under 35 U.S.C. 154(b) by 0 days.

(21) Appl. No.: 09/269,595

(22) PCT Filed: Sep. 23, 1997

(86) PCT No.: PCT/GB97/02588

§ 371 (c)(1),
(2), (4) Date: Mar. 25, 1999

(87) PCT Pub. No.: WO98/13354

PCT Pub. Date: Apr. 2, 1998

(30) Foreign Application Priority Data

Sep. 25, 1996 (EP) ............................................. 96402033
May 9, 1997 (EP) ............................................. 97401042

(51) Int. Cl.$^7$ .......................................... C07D 239/72
(52) U.S. Cl. .................... 544/283; 544/284; 544/293
(58) Field of Search ..................... 544/293, 283, 544/284

(56) References Cited

U.S. PATENT DOCUMENTS

| | | | |
|---|---|---|---|
| 5,457,105 A | 10/1995 | Barker .................... | 514/234.5 |
| 5,475,001 A | 12/1995 | Barker .................... | 514/258 |
| 5,569,658 A | 10/1996 | Barker .................... | 514/250 |
| 5,580,870 A | 12/1996 | Barker et al. ........... | 514/234.5 |
| 5,616,582 A | 4/1997 | Barker .................... | 514/234.5 |
| 5,770,599 A | 6/1998 | Gibson ................... | 514/228.2 |
| 5,770,603 A | 6/1998 | Gibson ................... | 514/259 |
| 5,814,630 A | 9/1998 | Barker et al. ........... | 514/234.5 |
| 5,821,246 A | 10/1998 | Brown et al. ............ | 514/253 |
| 5,866,572 A | 2/1999 | Barker et al. ........... | 514/234.5 |
| 5,932,574 A | 8/1999 | Barker .................... | 514/234.5 |
| 5,942,514 A | 8/1999 | Barker .................... | 514/254 |
| 5,952,333 A | 9/1999 | Barker .................... | 514/254 |
| 5,955,464 A | 9/1999 | Barker .................... | 514/254 |
| 5,962,458 A | 10/1999 | Lohmann et al. ........ | 514/254 |
| 6,015,814 A | 1/2000 | Barker .................... | 514/254 |
| 6,071,921 A | 6/2000 | Lohmann et al. ........ | 514/254 |
| 6,184,225 B1 | 2/2001 | Thomas et al. .......... | 514/254 |

FOREIGN PATENT DOCUMENTS

| | | | |
|---|---|---|---|
| EP | 566226 | * | 1/1993 |
| EP | 566 226 | | 10/1993 |
| JP | 54-2327 | | 9/1979 |
| WO | 9732856 | * | 1/1993 |
| WO | WO 96/29331 | | 10/1996 |
| WO | 97 22596 | | 6/1997 |
| WO | 97 32856 | | 9/1997 |

OTHER PUBLICATIONS

Klohs, Wayne D. et al. "Antiangiogenic Agts.", Curr. Opin. Biotech. 10/6.544–49, Jun. 1999.*
Golovkin et al., Nauchin TR–VSES–NAUCHO–ISSLED INST FARM, 1990, 28, 70–75.
Schonowsky et al., Chinazolinderivate, ihre Herstellung und biologische Wirkung, Quinazaolines, their Preparation and Biological Activity, Z. Naturforsch, 37b, 1982, pp. 907–911.

* cited by examiner

Primary Examiner—Richard Raymond
Assistant Examiner—Sudhaker B. Patel
(74) Attorney, Agent, or Firm—Morgan, Lewis & Bockius LLP

(57) ABSTRACT

The invention relates to quinazoline derivatives of formula (1)

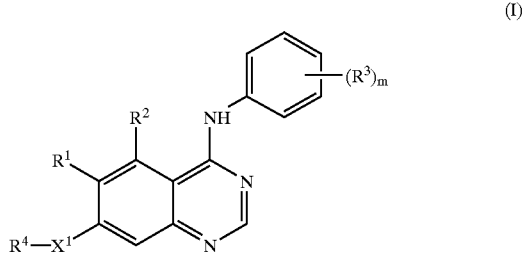

wherein m is an integer from 1 to 2; $R^1$ represents hydrogen, hydroxy, halogeno, nitro, trifluoromethyl, cyano, $C_{1-3}$alkyl, $C_{1-3}$alkoxy, $C_{1-3}$alkylthio, or —$NR^5R^6$ (wherein $R^5$ and $R^6$, which may be the same or different, each represents hydrogen or $C_{1-3}$alkyl); $R^2$ represents hydrogen, hydroxy, halogeno, methoxy, amino or nitro; $R^3$ represents hydroxy, halogeno, $C_{1-3}$alkyl, $C_{1-3}$alkoxy, $C_{1-3}$alkanoyloxy, trifluoromethyl, cyano, amino or nitro; $X^1$ represents —O—, —$CH_2$—, —S—, —SO—, —$SO_2$—, —$NR^7CO$—, —$CONR^8$—, —$SO_2NR^9$—, —$NR^{10}SO_2$— or —$NR^{11}$— (wherein $R^7$, $R^8$, $R^9$, $R^{10}$ and $R^{11}$ each independently represents hydrogen, $C_{1-3}$alkyl or $C_{1-3}$alkoxy$C_{2-3}$alkyl); $R^4$ represents an optionally substituted 5 or 6 membered saturated carbocyclic or heterocyclic group or a group which is alkenyl, alkynyl or optionally substituted alkyl, which alkyl group may contain a heteroatom linking group, which alkenyl, alkynyl or alkyl group may carry a terminal optionally substituted group selected from alkyl and a 5 or 6 membered saturated carbocyclic or heterocyclic group, and salts thereof; processes for their preparation, pharmaceutical compositions containing a compound of formula (I) or a pharmaceutically acceptable salt thereof as active ingredient. The compounds of formula (I) and pharmaceutically acceptable salts thereof inhibit the effects of VEGF, a property of value in the treatment of a number of disease states including cancer and rheumatoid arthritis.

23 Claims, No Drawings

QUINAZOLINE DERIVATIVES AND PHARMACEUTICAL COMPOSITIONS CONTAINING THEM

This application is the national phase of international application PCT/GB97/02588 filed Sep. 23, 1997 which designated the U.S.

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folknan, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

European Patent Publication No. 0326330 discloses certain quinoline, quinazoline and cinnoline plant fungicides. Certain of these plant fungicides are also stated to possess insecticidal and miticidal activity. There is however no disclosure or any suggestion that any of the compounds disclosed may be used for any purpose in animals such as humans. In particular, the European Patent Publication contains no teaching whatsoever concerning angiogenesis and/or increased vascular permeability mediated by growth factors such as VEGF.

European Patent Publication No. 0566226 discloses anilinoquinazolines which have activity against epidermal growth factor (EGF) receptor tyrosine kinase. EP 0566226 contains no teaching whatsoever concerning angiogenesis and/or increased vascular permeability mediated by growth factors such as VEGF. Moreover compounds of EP 0566226 which have been tested do not show significant activity against VEGF receptor tyrosine kinase.

The present invention is based on the surprising discovery that certain quinazolines inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess good activity against VEGF receptor tyrosine kinase whilst possessing some activity against EGF receptor tyrosine kinase. Furthermore, some compounds of the present invention, possess substantially higher potency against VEGF receptor tyrosine kinase than against EGF receptor tyrosine kinase or FGF R1 receptor tyrosine kinase. Thus certain compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase or FGF R1 receptor tyrosine kinase. While we do not wish to be bound by theoretical considerations such compounds may for example be of interest in treating tumours which are associated with VEGF, especially those tumours which are dependent on VEGF for their growth.

Other compounds of the invention possess good activity against both VEGF and EGF receptor tyrosine kinases. Indeed certain compounds possess substantially equivalent activities against VEGF and EGF receptor tyrosine kinases. It is believed that these compounds may be of interest in treating tumour states associated with both VEGF and EGF, especially where a patient is suffering from a condition in which tumours are present which are dependent on both VEGF and EGF for their growth.

According to one aspect of the present invention there is provided a quinazoline derivative of the formula I:

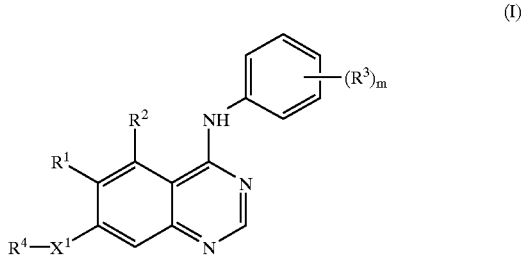

[wherein:

m is an integer from 1 to 2;

$R^1$ represents hydrogen, hydroxy, halogeno, nitro, trifluoromethyl, cyano, $C_{1-3}$alkyl, $C_{1-3}$alkoxy, $C_{1-3}$alkylthio, or —$NR^5R^6$ (wherein $R^5$ and $R^6$, which may be the same or different, each represents hydrogen or $C_{1-3}$alkyl);

$R^2$ represents hydrogen, hydroxy, halogeno, methoxy, amino or nitro;

$R^3$ represents hydroxy, halogeno, $C_{1-3}$alkyl, $C_{1-3}$alkoxy, $C_{1-3}$alkanoyolxy, trifluoromethyl, cyano, amino or nitro;

$X^1$ represents —O—, —$CH_2$—, —S—, —SO—, —$SO_2$—, —$NR^7CO$—, —$CONR^8$—, —$SO_2NR^9$—, —$NR^{10}SO_2$— or —$NR^{11}$— (wherein $R^7$, $R^8$, $R^9$, $R^{10}$ and $R^{11}$ each independently represents hydrogen, $C_{1-3}$alkyl or $C_{1-3}$alkoxy$C_{2-3}$alkyl);

$R^4$ is selected from one of the following eight groups:
1) $C_{1-5}$alkyl$R^{12}$ (wherein $R^{12}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl) or $C_{1-5}$alkyl$R^{13}$ (wherein $R^{13}$ is a group selected from pyrrolidin-1-yl, imidazolidin-1-yl and thiomorpholino, which group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
2) $C_{2-5}$alkenyl$R^{14}$ (wherein $R^{14}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
3) $C_{2-5}$alkynyl$R^{15}$ (wherein $R^{15}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N N-di($C_{1-4}$alkyl)carbamoyl, $C_{1-4}$alkanoyl and $C_{1-4}$alkoxycarbonyl);
4) $C_{1-5}$alkyl$X^2C_{1-5}$alkyl$X^3R^{16}$ (wherein $X^2$ and $X^3$ which may be the same or different are each —O—, —S—, —SO—, —$SO_2$—, —$NR^{17}CO$—, —$CONR^{18}$—, —$SO_2NR^{19}$—, —$NR^{20}SO_2$— or —$NR^{21}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl) and $R^{16}$ represents hydrogen or $C_{1-3}$alkyl) with the proviso that $X^1$ cannot be —$C_2$— when $R^4$ is $C_{1-5}$alkyl$X^2C_{1-5}$alkyl$X^3R^{16}$;
5) $C_{1-5}$alkyl$X^4COR^{22}$ (wherein $X^4$ represents —O— or —$NR^{23}$— (wherein $R^{23}$ represents hydrogen, $C_{1-3}$alkyl or $C_{1-3}$alkoxy$C_{2-3}$alkyl) and $R^{22}$ represents —$NR^{24}R^{25}$ or —$OR^{26}$ (wherein $R^{24}$, $R^{25}$ and $R^{26}$ which may be the same or different each represents hydrogen, $C_{1-4}$alkyl or $C_{1-3}$alkoxy$C_{2-3}$alkyl));
6) $C_{1-5}$alkyl$X^5R^{27}$ (wherein $X^5$ represents —O—, —S—, —SO—, —$SO_2$—, —OCO—, —$NR^{28}CO$—, —$CONR^{29}$—, —$SO_2NR^{30}$—, —$NR^{31}SO_2$— or —$NR^{32}$— (wherein $R^{28}$, $R^{29}$, $R^{30}$, $R^{31}$ and $R^{32}$ each independently represents hydrogen, $C_{1-3}$alkyl or $C_{1-3}$alkoxy$C_{2-3}$alkyl) or $X^5$ is carbonyl, and $R^{27}$ represents cyclopentyl, cyclohexyl or a 5 or 6 membered saturated heterocyclic group with one or two heteroatoms, selected independently from O, S and N, which cyclopentyl, cyclohexyl or heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl or $R^{27}$ is $C_{1-3}$alkyl with the proviso that when $R^{27}$ is $C_{1-3}$alkyl, $X^5$ is —S—, —SO—, —$SO_2$—, —$SO_2NR^{30}$— or —$NR^{31}SO_2$— and $X^1$ is not —$CH_2$—);
7) $C_{1-3}$alkoxy$C_{2-4}$alkyl provided that $X^1$ is —S—, or $X^1$ is —SO— or —$SO_2$—; and
8) $C_{1-3}$alkoxy$C_{2-4}$alkyl or $C_{1-4}$alkyl provided that $X^1$ is —O—; and additionally $R^4$ may be selected from the following five groups:
9) $C_{1-5}$alkyl$X^6C_{1-5}$alkyl$R^{33}$ (wherein $X^6$ represents —O—, —S—, —SO—, —$SO_2$—, —$NR^{34}CO$—, —$CONR^{35}$—, —$SO_2NR^{36}$—, —$NR^{37}SO_2$— or —$NR^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{33}$ represents cyclopentyl, cyclohexyl or a 5 or 6 membered saturated heterocyclic group with one or two heteroatoms, selected independently from O, S and N, which cyclopentyl, cyclohexyl or heterocyclic group may bear one or two substituents selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
10) $R^{39}$ (wherein $R^{39}$ is a group selected from pyrrolidin-3-yl, piperidin-3-yl and piperidin-4-yl which group may bear one or two substituents selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
11) $C_{1-5}$alkyl$R^{40}$ (wherein $R^{40}$ is piperazin-1-yl which bears at least one substituent selected from $C_{1-4}$alkanoyl, $C_{1-4}$alkoxycarbonyl, $C_{1-4}$hydroxyalkyl and —$CONR^{41}R^{42}$ (wherein $R^{41}$ and $R^{42}$ each independently represents hydrogen or $C_{1-4}$alkyl);
12) $C_{1-5}$alkyl$R^{43}$ (wherein $R^{43}$ is morpholino which may bear one or two substituents selected from oxo, $C_{1-4}$alkyl, $C_{1-4}$hydroxyalkyl, carbamoyl, $C_{1-4}$alkylcarbamoyl, N,N-di($C_{1-4}$alkyl)carbamoyl, $C_{1-4}$alkanoyl and $C_{1-4}$alkoxycarbonyl) with the proviso that when $R^4$ is $C_{1-5}$alkyl$R^{43}$, $X^1$ is —S—, —SO—, —$SO_2$—, —$SO_2NR^9$— or —$NR^{10}SO_2$—; and
13) $C_{1-5}$alkyl$R^{44}$ (wherein $R^{44}$ is morpholino which bears at least one and optionally two substituents selected from oxo, $C_{1-4}$alkyl, $C_{1-4}$hydroxyalkyl, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);

with the further proviso that when $R^4$ is selected from group 8) $R^1$ and/or $R^2$ is/are nitro or at least one $R^3$ is $C_{1-3}$alkanoyloxy;]
and salts thereof.

Preferably m is 2.

$R^1$ is advantageously hydrogen, hydroxy, cyano, nitro, trifluoromethyl, $C_{1-3}$alkyl, $C_{1-3}$alkoxy or amino.

$R^1$ is preferably hydrogen, hydroxy, cyano, nitro, trifluoromethyl, methyl, ethyl, methoxy or ethoxy, more preferably hydrogen, methyl or methoxy, most preferably hydrogen or methoxy, but especially methoxy.

$R^2$ is preferably hydrogen, fluoro, amino or nitro, but especially hydrogen.

In one embodiment of the present invention $R^3$ represents hydroxy, halogeno, $C_{1-2}$alkyl, $C_{1-2}$alkoxy, trifluoromethyl, cyano, amino or nitro.

Advantageously in another embodiment of the present invention one $R^3$ substituent is metahydroxy and the other one is selected from halogeno and methyl.

In another embodiment of the invention the phenyl group bearing $(R^3)_m$ is preferably of the formula II:

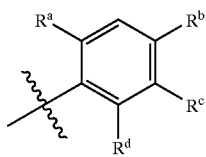

(II)

wherein:
$R^a$ represents hydrogen, methyl, fluoro or chloro, preferably hydrogen or fluoro;
$R^b$ represents hydrogen, methyl, methoxy, bromo, fluoro or chloro, especially hydrogen, methyl or chloro;
$R^c$ represents hydrogen or hydroxy;
$R^d$ represents hydrogen, fluoro or chloro, especially hydrogen or fluoro.

In a particular aspect of the present invention, the phenyl group bearing $(R^3)_m$ is the 3-hydroxy-4-methylphenyl group, the 2-fluoro-5-hydroxyphenyl group or the 4-chloro-2-fluorophenyl group, or the 4-bromo-2-fluorophenyl group, especially the 4-chloro-2-fluorophenyl group or the 4-bromo-2-fluorophenyl group more especially the 4-chloro-2-fluorophenyl group.

Advantageously $X^1$ represents —O—, —S—, —$NR^7CO$—, —$NR^{10}SO_2$— or —$NR^{11}$— (wherein $R^7$, $R^{10}$ and $R^{11}$ each independently represents hydrogen, $C_{1-2}$alkyl or $C_{1-2}$alkoxyethyl).

Preferably $X^1$ represents —O—, —S—, —$NR^7CO$— or —$NR^{10}SO_2$— (wherein $R^7$ and $R^{10}$ each independently represents hydrogen or $C_{1-2}$alkyl).

More preferably $X^1$ represents —O—, —S—, —$NR^7CO$— (wherein $R^7$ represents hydrogen or methyl). Particularly $X^1$ represents —O—, or —NHCO—, or —S—, especially —O—, or —S— more especially —O—. Conveniently $X^2$ and $X^3$ which may be the same or different each represents —O—, —S—, —SO—, —$SO_2$—, —$NR^{17}CO$—, or —$NR^{21}$— (wherein $R^{17}$ and $R^{21}$ each independently represents hydrogen, $C_{1-2}$alkyl or $C_{1-2}$alkoxyethyl).

Advantageously $X^2$ and $X^3$ which may be the same or different each represents —O—, —S—, —SO—, —$SO_2$— or —$NR^{21}$— (wherein $R^{21}$ represents hydrogen, $C_{1-2}$alkyl or $C_{1-2}$alkoxyethyl).

Preferably $X^2$ and $X^3$ which may be the same or different each represents —O—, —S— or —$NR^{21}$— (wherein $R^{21}$ represents hydrogen, $C_{1-2}$alkyl or $C_{1-2}$alkoxyethyl).

In a particular aspect of the present invention $X^3$ is —O— and $X^2$ is —$NR^{17}CO$— (wherein $R^{17}$ represents hydrogen, or methyl).

Advantageously $X^4$ represents —O— or —$NR^{23}$— (wherein $R^{23}$ represents hydrogen, $C_{1-3}$alkyl or $C_{1-2}$alkoxyethyl).

Advantageously $X^5$ represents —O—, —S—, —SO—, —$SO_2$—, —$NR^{28}CO$—, —$NR^{31}SO_2$— or —$NR^{32}$— (wherein $R^{28}$, $R^{31}$ and $R^{32}$ each independently represents hydrogen, $C_{1-2}$alkyl or $C_{1-2}$alkoxyethyl) or $X^5$ is carbonyl.

Preferably $X^5$ represents —O—, —S—, —SO—, —$SO_2$— or —$NR^{32}$— (wherein $R^{32}$ represents hydrogen, $C_{1-2}$alkyl or $C_{1-2}$alkoxyethyl).

More preferably $X^5$ represents —O— or —$NR^{32}$— (wherein $R^{32}$ represents hydrogen or $C_{1-2}$alkyl).

Advantageously $X^6$ represents —O—, —S—, —SO—, —$SO_2$—, —$NR^{34}CO$—, —$NR^{37}SO_2$— or —$NR^{38}$— (wherein $R^{34}$, $R^{37}$ and $R^{38}$ each independently represents hydrogen, $C_{1-2}$alkyl or $C_{1-2}$alkoxyethyl).

Preferably $X^6$ represents —O—.

Conveniently $R^4$ is selected from one of the following eight groups:
1) $C_{1-5}$alkyl$R^{12}$ (wherein $R^{12}$ is a group selected from 1,3-dioxolan-2-yl, 1,3-dioxan-2-yl, 1,3-dithiolan-2-yl, 1,3-dithian-2-yl, pyrrolidin-2-yl and pyrrolidin-3-yl, and piperidin-2-yl, piperidin-3-yl, piperidin-4-yl, morpholin-2-yl, morpholin-3-yl and piperazin-2-yl which group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl) or $C_{2-5}$alkyl$R^{45}$ (wherein $R^{45}$ is a group selected from imidazolidin-1-yl, pyrrolidin-1-yl and thiomorpholino, which group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
2) $C_{3-5}$alkenyl$R^{46}$ (wherein $R^{46}$ is a 5 or 6 membered saturated heterocyclic group with one or two heteroatoms, selected independently from O, S and N, which heterocyclic group is linked to $C_{3-5}$alkenyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl) or $C_{4-5}$alkenyl$R^{47}$ (wherein $R^{47}$ is a 5 or 6 membered saturated heterocyclic group with one or two heteroatoms of which one is N and the other is selected independently from O, S and N, which heterocyclic group is linked to $C_{4-5}$alkenyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
3) $C_{3-5}$alkynyl$R^{48}$ (wherein $R^{48}$ is a 5 or 6 membered saturated heterocyclic group with one or two heteroatoms, selected independently from O, S and N, which heterocyclic group is linked to $C_{3-5}$alkynyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl) carbamoyl, $C_{1-4}$alkanoyl and $C_{1-4}$alkoxycarbonyl) or $C_{4-5}$alkynyl$R^{49}$ (wherein $R^{49}$ is a 5 or 6 membered saturated heterocyclic group with one or two heteroatoms of which one is N and the other is selected independently from O, S and N, which heterocyclic group is linked to $C_{4-5}$alkynyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl);

4) $C_{2-3}$alkyl$X^2C_{2-3}$alkyl$X^3R^{16}$ (wherein $X^2$ and $X^3$ are as defined hereinbefore and $R^{16}$ represents hydrogen or $C_{1-3}$alkyl) with the proviso that $X^1$ cannot be —$CH_2$— when $R^4$ is $C_{2-3}$alkyl$X^2C_{2-3}$alkyl$X^3R^{16}$;

5) $C_{2-3}$alkyl$X^4COR^{22}$ (wherein $X^4$ is as defined hereinbefore and $R^{22}$ represents —$NR^{24}R^{25}$ or —$OR^{26}$ (wherein $R^{24}$, $R^{25}$ and $R^{26}$ which may be the same or different each represents hydrogen, $C_{1-4}$alkyl or $C_{1-2}$alkoxyethyl));

6) $C_{2-4}$alkyl$X^5R^{27}$ (wherein $X^5$ is as defined hereinbefore and $R^{27}$ represents cyclopentyl, cyclohexyl or a 5 or 6 membered saturated heterocyclic group with one or two heteroatoms, selected independently from O, S and N, which cyclopentyl, cyclohexyl or heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-4}$alkylcarbamoyl, N,N-di($C_{1-4}$alkyl)carbamoyl, $C_{1-4}$alkanoyl and $C_{1-4}$alkoxycarbonyl or $R^{27}$ is $C_{1-3}$alkyl with the proviso that when $R^{27}$ is $C_{1-3}$alkyl, $X^5$ is —S—, —SO—, —$SO_2$—, —$SO_2NR^{30}$— or —$NR^{31}SO_2$— and $X^1$ is not —$CH_2$—);

7) $C_{1-3}$alkoxy$C_{2-4}$alkyl provided that $X^1$ is —S—, or $X^1$ is —SO— or —$SO_2$—; and 8) $C_{1-3}$alkoxy$C_{2-4}$alkyl or $C_{1-4}$alkyl provided that $X^1$ is —O—; and additionally $R^4$ may conveniently be selected from the following four groups:

9) $C_{2-4}$alkyl$X^6C_{2-4}$alkyl$R^{33}$ (wherein $X^6$ is as defined hereinbefore and $R^{33}$ represents a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);

10) $C_{2-4}$alkyly$R^{40}$ (wherein $R^{40}$ is piperazin-1-yl which bears at least one substituent selected from $C_{2-3}$alkanoyl, $C_{1-3}$alkoxycarbonyl, $C_{1-3}$hydroxyalkyl and $CONR^{41}R^{42}$ (wherein $R^{41}$ and $R^{42}$ each independently represents hydrogen or $C_{1-3}$alkyl));

11) $C_{2-4}$alkyl$R^{43}$ (wherein $R^{43}$ is morpholino which may bear one or two substituents selected from oxo, $C_{1-3}$alkyl, $C_{1-3}$hydroxyalkyl, carbamoyl, $C_{1-3}$alkylcarbamoyl, N,N-di($C_{1-3}$alkyl)carbamoyl, $C_{2-3}$alkanoyl and $C_{1-3}$alkoxycarbonyl) with the proviso that when $R^4$ is $C_{2-4}$alkyl $R^{43}$, $X^1$ is —S—, —SO—, —$SO_2$—, —$SO_2NR^9$— or —$NR^{10}SO_2$—; and 12) $C_{2-4}$alkyl$R^{44}$ (wherein $R^{44}$ is morpholino which bears at least one and optionally two substituents selected from oxo, $C_{1-3}$alkyl, $C_{1-3}$hydroxyalkyl, carbamoyl, $C_{1-3}$alkylcarbamoyl, N,N-di($C_{1-3}$alkyl)carbamoyl, $C_{2-3}$alkanoyl and $C_{1-3}$alkoxycarbonyl);

with the further proviso that when $R^4$ is selected from group 8) $R^1$ and/or $R^2$ is/are nitro or at least one $R^3$ is $C_{1-3}$alkanoyloxy.

An additional convenient value of $R^4$ is $C_{2-3}$alkyl$X^2$methyl$X^3R^{16}$ (wherein $X^2$ and $X^3$ are as defined hereinbefore and $R^{16}$ represents hydrogen or $C_{1-3}$alkyl) with the proviso that $X^1$ cannot be —$CH_2$— when $R^4$ is $C_{2-3}$alkyl$X^2$methyl$X^3R^{16}$.

Advantageously $R^4$ is selected from one of the following seven groups:

1) $C_{1-4}$alkyl$R^{12}$ (wherein $R^{12}$ is a group selected from 1,3-dioxolan-2-yl, 1,3-dioxan-2-yl, 1,3-dithiolan-2-yl, 1,3-dithian-2-yl, pyrrolidin-2-yl and pyrrolidin-3-yl, and piperidin-2-yl, piperidin-3-yl, piperidin-4-yl, morpholin-2-yl, morpholin-3-yl and piperazin-2-yl which group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, $C_{2-3}$alkanoyl and $C_{1-3}$alkoxycarbonyl) or $C_{2-4}$alkyl$R^{45}$(wherein $R^{45}$ is a group selected from imidazolidin-1-yl, pyrrolidin-1-yl and thiomorpholino which group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, $C_{2-3}$alkanoyl and $C_{1-3}$alkoxycarbonyl);

2) 1-$R^{46}$prop-1-en-3-yl, 1-$R^{46}$but-2-en-4-yl, 1-$R^{46}$but-1-en-3-yl, 1-$R^{46}$pent-2-en-4-yl or 2-$R^{46}$pent-3-en-5-yl (wherein $R^{46}$ is a 5 or 6 membered saturated heterocyclic group with one or two heteroatoms, selected independently from O, S and N, which heterocyclic group is linked to the alkenyl group through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamnoyl, N,N-di($C_{1-3}$alkyl)carbamoyl, $C_{2-3}$alkanoyl and $C_{1-3}$alkoxycarbonyl) or 1-$R^{47}$but-2-en-4-yl, 1-$R^{47}$pent-2-en-4-yl or 2-$R^{47}$pent-3-en-5-yl (wherein $R^{47}$ is a 5 or 6 membered saturated heterocyclic group with one or two heteroatoms, of which one is N and the other is selected independently from O, S and N, which heterocyclic group is linked to the alkenyl group through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl) carbamoyl, $C_{2-3}$alkanoyl and $C_{1-3}$alkoxycarbonyl);

3) 1-$R^{48}$prop-1-yn-3-yl, 1-$R^{48}$but-2-yn-4-yl, 1-$R^{48}$but-1-yn-3-yl, 1-$R^{48}$pent-2-yn-4-yl or 2-$R^{48}$pent-3-yn-5-yl (wherein $R^{48}$ is a 5 or 6 membered saturated heterocyclic group with one or two heteroatoms, selected independently from O, S and N, which heterocyclic group is linked to the alkynyl group through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, $C_{2-3}$alkanoyl and $C_{1-3}$alkoxycarbonyl) or 1-$R^{49}$but-2-yn-4-yl, 1-$R^{49}$pent-2-yn-4-yl or 2-$R^{49}$pent-3-yn-5-yl (wherein $R^{49}$ is a 5 or 6 membered saturated heterocyclic group with one or two heteroatoms, of which one is N and the other is selected independently from O, S and N, which heterocyclic group is linked to the alkynyl group through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, $C_{2-3}$alkanoyl and $C_{1-3}$alkoxycarbonyl);

4) $C_{2-3}$alkylX$^2$C$_{2-3}$alkylX$^3$R$^{16}$ (wherein $X^2$ and $X^3$ are as defined hereinbefore and $R^{16}$ represents hydrogen or $C_{1-3}$alkyl) with the proviso that $X^1$ cannot be —CH$_2$— when $R^4$ is $C_{2-3}$alkylX$^2$C$_{2-3}$alkylX$^3$R$^{16}$;

5) $C_{2-3}$alkylX$^4$COR$^{22}$ (wherein $X^4$ is as defined hereinbefore and $R^{22}$ represents —NR$^{24}$R$^{25}$ or —OR$^{26}$ (wherein $R^{24}$, $R^{25}$ and $R^{26}$ which may be the same or different each represents hydrogen, $C_{1-4}$alkyl or $C_{1-2}$alkoxyethyl));

6) $C_{2-3}$alkylX$^5$R$^{27}$ (wherein $X^5$ is as defined hereinbefore and $R^{27}$ represents a group selected from cyclopentyl, cyclohexyl pyrrolidinyl and piperidinyl which group is linked to $X^5$ through a carbon atom and which group may carry one substituent selected from oxo, hydroxy, halogeno, $C_{1-2}$alkyl, $C_{1-2}$hydroxyalkyl and $C_{1-2}$alkoxy, and additional possible substituents are carbamoyl, $C_{1-2}$akylcarbamoyl, N,N-di($C_{1-2}$alkyl)carbamoyl, acetyl and $C_{1-2}$alkoxycarbonyl or $R^{27}$ is $C_{1-3}$alkyl with the proviso that when $R^{27}$ is $C_{1-3}$alkyl, $X^5$ is —S—, —SO—, —SO$_2$—, —SO$_2$NR$^{30}$— or —NR$^{31}$SO$_2$— and $X^1$ is not —CH$_2$—); and 7) $C_{1-2}$alkoxyC$_{2-3}$alkyl provided that $X^1$ is —S—, or $X^1$ is —SO— or —SO$_2$—; and additionally $R^4$ may advantageously be selected from the following four groups:

8) $C_{2-3}$alkylX$^6$C$_{2-3}$alkylR$^{33}$ (wherein $X^6$ is as defined hereinbefore and $R^{33}$ represents a 5 or 6 membered saturated heterocyclic group with one or two heteroatoms, selected independently from O, S and N, which heterocyclic group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl)carbamoyl, $C_{2-3}$alkanoyl, and $C_{1-3}$alkoxycarbonyl);

9) $C_{2-3}$alkylR$^{40}$ (wherein $R^{40}$ is piperazin-1-yl which bears at least one substituent selected from acetyl, $C_{1-2}$alkoxycarbonyl, $C_{1-2}$hydroxyalkyl and CONR$^{41}$R$^{42}$ (wherein $R^{41}$ and $R^{42}$ each independently represents hydrogen or $C_{1-2}$alkyl);

10) $C_{2-3}$alkylR$^{43}$ (wherein $R^{43}$ is morpholino which may bear one or two substituents selected from oxo, $C_{1-2}$alkyl, $C_{1-2}$hydroxyalkyl, carbamoyl, $C_{1-2}$alkylcarbamoyl, N,N-di($C_{1-2}$alkyl)carbamoyl, acetyl and $C_{1-2}$alkoxycarbonyl) with the proviso that when $R^4$ is $C_{2-3}$alkylR$^{43}$, $X^1$ is —S—, —SO—, —SO$_2$—, —SO$_2$NR$^9$— or —NR$^{10}$SO$_2$—; and 11) $C_{2-3}$alkylR$^{44}$ (wherein $R^{44}$ is morpholino which bears at least one and optionally two substituents selected from oxo, $C_{1-2}$alkyl, $C_{1-2}$hydroxyalkyl, carbamoyl, $C_{1-2}$alkylcarbamoyl, N,N-di($C_{1-2}$alkyl)carbamoyl, acetyl and $C_{1-2}$alkoxycarbonyl).

An additional advantageous value of $R^4$ is $C_{2-3}$alkylX$^2$methylX$^3$R$^{16}$ (wherein $X^2$ and $X^3$ are as defined hereinbefore and $R^{16}$ represents hydrogen or $C_{1-3}$alkyl) with the proviso that $X^1$ cannot be —CH$_2$— when $R^4$ is $C_{2-3}$alkyX$^2$xmethylX$^3$R$^{16}$.

Preferably $R^4$ is selected from one of the following seven groups:

1) $C_{1-3}$alkylR$^{12}$ (wherein $R^{12}$ is a group selected from 1,3dioxolan-2-yl, 1,3-dioxan-2-yl, 1,3-dithiolan-2-yl, 1,3-dithian-2-yl, pyrrolidin-2-yl and pyrrolidin-3-yl and piperidin-2-yl, piperidin-3-yl, piperidin-4-yl, morpholin-2-yl, morpholin-3-yl and piperazin-2-yl which group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, acetyl and $C_{1-3}$alkoxycarbonyl) or $C_{2-3}$alkylR$^{45}$ (wherein $R^{45}$ is a group selected from imidazolidin-1-yl, pyrrolidin-1-yl and thiomorpholino which group may bear one or two substituents selected from oxo, hydroxy, halogeno, $C_{1-3}$alkyl, $C_{1-3}$hydroxyalkyl and $C_{1-3}$alkoxy and additional possible substituents are carbamoyl, $C_{1-3}$alkylcarbamoyl, N,N-di($C_{1-3}$alkyl)carbamoyl, acetyl and $C_{1-3}$alkoxycarbonyl);

2) 1-R$^{46}$but-2-en-4-yl (wherein $R^{46}$ is a 5 or 6 membered saturated heterocyclic group with one or two heteroatoms, selected independently from O, S and N, which heterocyclic group is linked to the alkenyl group through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, acetyl and $C_{1-3}$alkoxycarbonyl) or 1-R$^{47}$but-2-en-4-yl (wherein $R^{47}$ is a 5 or 6 membered saturated heterocyclic group with one or two heteroatoms, of which one is N and the other is selected independently from O, S and N, which heterocyclic group is linked to the alkenyl group through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, acetyl and $C_{1-3}$alkoxycarbonyl);

3) 1-R$^{48}$but-2-yn-4-yl (wherein $R^{48}$ is a 5 or 6 membered saturated heterocyclic group with one or two heteroatoms, selected independently from O, S and N, which heterocyclic group is linked to the alkynyl group through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, acetyl and $C_{1-3}$alkoxycarbonyl) or 1-R$^{49}$but-2-yn-4-yl (wherein $R^{49}$ is a 5 or 6 membered saturated heterocyclic group with one or two heteroatoms, of which one is N and the other is selected independently from O, S and N, which heterocyclic group is linked to the alkynyl group through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy, and additional possible substituents are carbamoyl, $C_{1-3}$alkylcarbamoyl, N,N-di($C_{1-3}$alkyl)carbamoyl, acetyl and $C_{1-3}$alkoxycarbonyl);

4) $C_{2-3}$alkylX$^2$C$_{2-3}$alkylX$^3$R$^{16}$ (wherein $X^2$ and $X^3$ are as defined hereinbefore and $R^{16}$ represents hydrogen or $C_{1-3}$alkyl) with the proviso that $X^1$ cannot be —CH$_2$— when $R^4$ is $C_{2-3}$alkylX$^2$C$_{2-3}$alkylX$^3$R$^{16}$;

5) 2-(3,3-dimethylureido)ethyl, 3-(3,3-dimethylureido) propyl, 2-(3-methylureidoethyl)ethyl, 3-(3- methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl or 2-(1,3,3-trimethylureido)ethyl, 3-(1,3,3-trimethylureido)propyl, 2-(isopropoxycarbonylamino)ethyl, 3-(isopropoxycarbonylamino)propyl, 2-(isobutoxycarbonylamino)ethyl, 3-(isobutoxycarbonylamino)propyl, 2-(t-butoxycarbonylamino)ethyl or 3-(t-butoxycarbonylamino)propyl;

6) $C_{2-3}$alkyl$X^5R^{27}$ (wherein $X^5$ is as defined hereinbefore and $R^{27}$ is a group selected from cyclopentyl, cyclohexyl, pyrrolidinyl and piperidinyl which group is linked to $X^5$ through a carbon atom and which group may carry one substituent selected from oxo, hydroxy, halogeno, $C_{1-2}$alkyl, $C_{1-2}$hydroxyalkyl and $C_{1-2}$alkoxy and additional possible substituents are carbamoyl, $C_{1-2}$alkylcarbamoyl, N,N-di($C_{1-2}$alkyl)carbamoyl, acetyl and $C_{1-2}$alkoxycarbonyl or $R^{27}$ is $C_{1-2}$alkyl with the proviso that when $R^{27}$ is $C_{1-2}$alkyl, $X^5$ is —S—, —SO—, —SO$_2$—, —SO$_2$NR$^{30}$— or —NR$^{31}$SO$_2$— and $X^1$ is not —CH$_2$—); and 7) $C_{1-2}$alkoxy$C_{2-3}$alkyl provided that $X^1$ is —S—, or $X^1$ is —SO— or —SO$_2$—; and additionally $R^4$ may preferably be selected from the following three groups:

8) $C_{2-3}$alkyl$X^6C_{2-3}$alkyl$R^{33}$ (wherein $X^6$ is as defined hereinbefore and $R^{33}$ represent a 5 or 6 membered saturated heterocyclic group with one or two heteroatoms, selected independently from O, S and N, of which at least one is N, which heterocyclic group is linked to $C_{2-3}$alkyl through a nitrogen atom and which heterocyclic group may bear one or two substituents selected from oxo, hydroxy, halogeno, $C_{1-2}$alkyl, $C_{1-2}$hydroxyalkyl, $C_{1-2}$alkoxy, carbamoyl, $C_{1-2}$alkylcarbamoyl, N,N-di($C_{1-2}$alkyl)carbamoyl, acetyl and $C_{1-2}$alkoxycarbonyl);

9) $C_{2-3}$alkyl$R^{43}$ (wherein $R^{43}$ is morpholino which may bear one or two substituents selected from oxo, $C_{1-2}$alkyl, $C_{1-2}$hydroxyalkyl, carbamoyl, $C_{1-2}$alkylcarbamoyl, N,N-di($C_{1-2}$alkyl)carbamoyl, acetyl and $C_{1-2}$alkoxycarbonyl) with the proviso that when $R^4$ is $C_{2-3}$alkyl$R^{43}$, $X^1$ is —S—, —SO—, —SO$_2$—, —SO$_2$NR$^9$— or —NR$^{10}$SO$_2$—); and 10) $C_{2-3}$alkyl$R^{44}$ (wherein $R^{44}$ is morpholino which bears at least one and optionally two substituents selected from oxo, $C_{1-2}$alkyl, $C_{1-2}$hydroxyalkyl, carbamoyl, $C_{1-2}$alkylcarbamoyl, N,N-di($C_{1-2}$alkyl)carbamoyl, acetyl and $C_{1-2}$alkoxycarbonyl).

An additional preferred value of $R^4$ is $C_{2-3}$alkyl$X^2$methyl$X^3R^{16}$ (wherein $X^2$ and $X^3$ are as defined hereinbefore and $R^{16}$ represents hydrogen or $C_{1-3}$alkyl) with the proviso that $X^1$ cannot be —CH$_2$— when $R^4$ is $C_{2-3}$alkyl$X^2$methyl$X^3R^{16}$.

More preferably $R^4$ is selected from one of the following five groups:

1) $C_{1-3}$alkyl$R^{12}$ (wherein $R^{12}$ is a group selected from 1,3-dioxolan-2-yl, 1,3-dioxan-2-yl, 1,3-dithiolan-2-yl, 1,3-dithian-2-yl, pyrrolidin-2-yl and pyrrolidin-3-yl and piperidin-2-yl, piperidin-3-yl, piperidin-4-yl, morpholin-2-yl, morpholin-3-yl and piperazin-2-yl which group may bear one or two substituents selected from oxo, hydroxy, halogeno, $C_{1-2}$alkyl, $C_{1-2}$hydroxyalkyl and $C_{1-2}$alkoxy, and additional possible substituents are carbamoyl, $C_{1-2}$alkylcarbamoyl, N,N-di($C_{1-2}$alkyl)carbamoyl, acetyl and $C_{1-2}$alkoxycarbonyl) or $C_{2-3}$alkyl$R^{45}$ (wherein $R^{45}$ is a group selected from imidazolidin-1-yl, pyrrolidin-1-yl and thiomorpholino which group may bear one or two substituents selected from oxo, hydroxy, halogeno, $C_{1-2}$alkyl, $C_{1-2}$hydroxyalkyl and $C_{1-2}$alkoxy, and additional possible substituents are carbamoyl, $C_{1-2}$alkylcarbamoyl, N,N-di($C_{1-2}$alkyl)carbamoyl, acetyl and $C_{1-2}$alkoxycarbonyl);

2) 1-$R^{50}$but-2-en-4-yl (wherein $R^{50}$ is a group selected from imidazolidin-1-yl, 1,3-dioxolan-2-yl, 1,3-dioxan-2-yl, 1,3-dithiolan-2-yl, 1,3dithian-2-yl, piperidin-4-yl, pyrrolidin-1-yl, pyrrolidin-3-yl, piperazin-1-y1, morpholino and thiomorpholino and piperidino which group may bear one or two substituents selected from oxo, hydroxy, halogeno, $C_{1-2}$alkyl, $C_{1-2}$hydroxyalkyl and $C_{1-2}$alkoxy, and additional possible substituents are carbamoyl, $C_{1-2}$alkylcarbamoyl, N,N-di($C_{1-2}$alkyl) carbamoyl, acetyl and $C_{1-2}$alkoxycarbonyl); 3) 1-$R^{51}$but-2-yn-4-yl (wherein $R^{51}$ is a group selected from imidazolidin-1-yl, 1,3-dioxolan-2-yl, 1,3-dioxan-2-yl, 1,3-dithiolan-2-yl, 1,3-dithian-2-yl, piperidin-4-yl, pyrrolidin-1-yl, pyrrolidin-3-yl, pipeiain-1-yl, morpholino and thiomorpholino and piperidino which group may bear one or two substituents selected from oxo, hydroxy, halogeno, C1-2alkyl, $C_{1-2}$hydroxyalkyl and $C_{1-2}$alkoxy, and additional possible substituents are carbamoyl, $C_{1-2}$alkylcarbamoyl, N,N-di($C_{1-2}$alkyl) carbamoyl, acetyl and $C_{1-2}$alkoxycarbonyl);

4) $C_{2-3}$alkyl$X^2C_{2-3}$alkyl$X^3R^{16}$ (wherein $X^2$ and $X^3$ are as defined hereinbefore and $R^{16}$ represents hydrogen or $C_{1-3}$alkyl) with the proviso that $X^1$ cannot be —CH$_2$— when $R^4$ is $C_{2-3}$alkyl$X^2C_{2-3}$alkyl$X^3R^{16}$; and 5) $C_{1-2}$alkoxy$C_{2-3}$alkyl provided that $X^1$ is —S—, or $X^1$ is —SO— or —SO$_2$—; and additionally $R^4$ may more preferably be selected from the following four groups:

6) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, 2-(1,3,3-trimethylureido) ethyl, 3-(1,3,3-trimethylureido)propyl, 2-(isopropoxycarbonylamino)ethyl, 3-(isopropoxycarbonylamino)propyl, 2-(isobutoxycarbonylamino)ethyl, 3-(isobutoxycarbonylamino)propyl, 2-(t-butoxycarbonylamino)ethyl or 3-(t-butoxycarbonylamino)propyl;

7) $C_{2-3}$alkyl$X^5R^{27}$ (wherein $R^{27}$ is $C_{1-2}$alkyl and $X^5$ is —S—, —SO—, —SO$_2$—, —SO$_2$NR$^{30}$— or —NR$^{31}$SO$_2$— and with the proviso that $X^1$ is not —CH$_2$—);

8) $C_{2-3}$alkyl$X^6C_{2-3}$alkyl$R^{33}$ (wherein $X^6$ is as defined hereinbefore and $R^{33}$ represents a group selected from morpholino, 2-oxopyrrolidin-1-yl, pyrrolidin-1-yl, piperidino, piperazin-1-yl and 4-methylpiperazin-1-yl); and 9) $C_{2-3}$alkyl$R^{43}$ (wherein $R^{43}$ is morpholino which may bear one or two substituents selected from oxo, $C_{1-2}$alkyl, $C_{1-2}$hydroxyalkyl, carbamoyl, $C_{1-2}$alkylcarbamoyl, N,N-di($C_{1-2}$alkyl)carbamoyl, acetyl and $C_{1-2}$alkoxycarbonyl) with the proviso that when R⁴ is C₂₋₃alkylR⁴³, X¹ is —S—, —SO—, —SO₂—, —SO₂NR⁹— or —NR¹⁰SO₂—.

An additional more preferred value of R⁴ is C₂₋₃alkylX²methylX³R¹⁶ (wherein X² and X³ are as defined hereinbefore and R¹⁶ represents hydrogen or C₁₋₃alkyl) with the proviso that X¹ cannot be —CH₂— when R⁴ is C₂₋₃alkylX²methylX³R¹⁶.

Most preferably R⁴ is selected from one of the following five groups:

1) C₁₋₃alkylR¹² (wherein R¹² is 1,3-dioxolan-2-yl, 1,3-dioxan-2-yl, 1,3-dithiolan-2yl, 1,3-dithian-2-yl, pyrrolidin-2-yl or pyrrolidin-3-yl or piperidin-2-yl, piperidin-3-yl piperidin-4-yl, 1-methylpiperidin-2-yl, 1-methylpiperidin-3-yl, 1-methylpiperidin-4-yl, 1-methylpyrrolidin-2-yl, 1-methylpyrrolidin-3-yl, piperazin-2-yl, 1-methylpiperazin-2-yl, 4-methylpiperazin-2-yl, 1,4-dimethylpiperazin-2-yl, morpholin-2-yl, morpholin-3-yl, 4-methylmorpholin-2-yl or 4-methylmorpholin-3-yl) or C₂₋₃alkylR⁴⁵ (wherein R⁴⁵ is pyrrolidin-1-yl or thiomorpholino or 1,1-dioxothiomorpholino, 2-oxopyrrolidin-1-yl, 2(N-methylcarbamoyl)pyrrolidin-1-yl, 2-(N,N-diethylcarbamoyl)pyrrolidin-1-yl, 2-carbamoylpyrrolidin-1-yl, 2-oxoimidazolidin-1-yl or 3-methyl-2-oxoimidazolidin-1-yl);

2) 1-R⁵⁰but-2-en-4-yl (wherein R⁵⁰ is 2-oxoimidazolidin-1-yl, 1,3-dioxolan-2-yl, 1,3-dioxan-2-yl, 1,3-dithiolan-2-yl, 1,3-dithian-2-yl, piperidin-4-yl, 1-methylpiperidin-4-yl, pyrrolidin-1-yl, 1-methylpyrrolidin-3-yl, piperazin-1-yl, morpholino or thiomorpholino or 4-methylpiperazin-1-yl, piperidino or 3-methyl-2-oxoimidazolidin-1-yl);

3) 1-R⁵¹but-2-yn-4-yl (wherein R⁵¹ is 2-oxoimidazolidin-1-yl, 1,3-dioxolan-2-yl, 1,3-dioxan-2-yl, 1,3-dithiolan-2-yl, 1,3-dithian-2-yl, piperidin-4-yl, 1-methylpiperidin-4-yl, pyrrolidin-1-yl, 1-methylpyrrolidin-3-yl, piperazin-1-yl, morpholino or thiomorpholino or 4-methylpiperazin-1-yl, piperidino or 3-methyl-2-oxoimidazolidin-1-yl);

4) C₂₋₃alkylX²C₂₋₃alkylX³R¹⁶ (wherein X² and X³ are as defined hereinbefore and R¹⁶ represents hydrogen or C₁₋₃alkyl) with the proviso that X¹ cannot be —CH₂— when R⁴ is C₂₋₃alkylX²C₂₋₃alkylX³R¹⁶; and 5) C₁₋₂alkoxyC₂₋₃alkyl provided that X¹ is —S—, or X¹ is —SO— or —SO₂—; and additionally R⁴ may most preferably be selected from the following three groups:

6) C₂₋₃alkylX⁵R²⁷ (wherein R²⁷ is C₁₋₂alkyl and X⁵ is —S—, —SO—, —SO₂—, —SO₂NR³⁰— or —NR³¹SO₂— and with the proviso that X¹ is not —CH₂—);

7) C₂₋₃alkylX⁶C₂₋₃alkylR³³ (wherein X⁶ is as defined hereinbefore and R³³ represents a group selected from pyrrolidin-1-yl, 4-methylpiperazin-1-yl and morpholino); and 8) C₂₋₃alkylR⁴³ (wherein R⁴³ is morpholino which may bear one or two substituents selected from oxo, C₁₋₂alkyl, C₁₋₂hydroxyalkyl) with the proviso that when R⁴ is C₂₋₃alkylR⁴³, X¹ is —S—, —SO—, —SO₂—, —SO₂NR⁹— or —NR¹⁰SO₂—.

An additional most preferred value of R⁴ is C₂₋₃alkylX²methylX³R¹⁶ (wherein X² and X³ are as defined hereinbefore and R¹⁶ represents hydrogen or C₁₋₃alkyl) with the proviso that X¹ cannot be —CH₂— when R⁴ is C₂₋₃alkylX²methylX³R¹⁶.

Especially preferred values for the group R⁴-X¹ are 3-(methylsulphonyl)propoxy, (1-methylpiperidin-3-yl) methoxy, 4-(pyrrolidin-1-yl)but-2-en-1-yloxy, 2-(2-methoxyethoxy)ethoxy, 3-(1,1-dioxothiomorpholino) propoxy, 2-(2-(pyrrolidin-1-yl)ethoxy)ethoxy, 2-(2-(4-methylpiperazin-1-yl)ethoxy)ethoxy, 3-morpholinopropylthio, 2-([N-methoxyacetyl-N-methyl] amino)ethoxy, 2-(2-oxopyrrolidin-1-yl)ethoxy, 2-thiomorpholinoethoxy, 3-(2-carbamoylpyrrolidin-1-yl) propoxy, 3-(2-oxopyrrolidin-1-yl)propoxy and 2-(2-morpholinoethoxy)ethoxy.

More especially preferred values for the group R⁴-X¹ are 3-(methylsulphonyl)propoxy, (1-methylpiperidin-3-yl) methoxy and 4-(pyrrolidin-1-yl)but-2-en-1-yloxy.

In a particular aspect of the present invention there is provided a compound of the formula Ia:

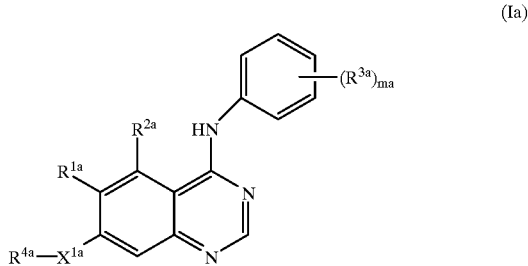

(Ia)

[wherein:
R¹ᵃ is hydrogen or methoxy;
R²ᵃ is hydrogen;
the phenyl group bearing (R³ᵃ)ₘₐ is the 4-chloro-2-fluorophenyl group or the 4-bromo-2-fluorophenyl group;
X¹ᵃ is —O—, —S—, —NR⁵ᵃCO— or —NR⁶ᵃSO₂— (wherein R⁵ᵃ and R⁶ᵃ each independently represents hydrogen or C₁₋₂alkyl);
R⁴ᵃ is selected from one of the following eleven groups:
1) C₁₋₄alkylR⁷ᵃ (wherein R⁷ᵃ is a group selected from 1,3-dioxolan-2-yl, 1,3-dioxan-2-yl, 1,3-dithiolan-2-yl, 1,3-dithian-2-yl, pyrrolidin-2-yl and pyrrolidin-3-yl, and piperidin-2-yl, piperidin-3-yl, piperidin-4-yl, morpholin-2-yl, morpholin-3-yl and piperazin-2-yl which group may bear one or two substituents selected from oxo, hydroxy, halogeno, C₁₋₃alkyl, C₁₋₃hydroxyalkyl, C₁₋₃alkoxy, carbamoyl, C₁₋₃alkylcarbamoyl, N,N-di(C₁₋₃alkyl)carbamoyl, C₂₋₃alkanoyl and C₁₋₃alkoxycarbonyl) or C₂₋₄alkylR⁸ᵃ (wherein R⁸ᵃ is a group selected from imidazolidin-1-yl, pyrrolidin-1-yl and thiomorpholino which group may bear one or two substituents selected from oxo, hydroxy, halogeno, C₁₋₃alkyl, C₁₋₃hydroxyalkyl, C₁₋₃alkoxy, carbamoyl, C₁₋₃alkylcarbamoyl, N,N-di(C₁₋₃alkyl)carbamoyl, C₂₋₃alkanoyl and C₁₋₃alkoxycarbonyl);

2) 1-R⁹ᵃprop-1-en-3-yl, 1-R⁹ᵃbut-2-en-4-yl, 1-R⁹ᵃbut-1-en-3-yl, 1-R⁹ᵃpent-2-en-4-yl or 2-R⁹ᵃpent-3-en-5-yl (wherein R⁹ᵃ is a 5 or 6 membered saturated heterocyclic group with one or two heteroatoms, selected independently from O, S and N, which heterocyclic group is linked to the alkenyl group through a carbon atom and which heterocyclic group may bear one or two substituents selected from oxo, hydroxy, halogeno, C₁₋₃alkyl, C₁₋₃hydroxyalkyl, C₁₋₃alkoxy, carbamoyl, C₁₋₃alkylcarbamoyl, N,N-di (C₁₋₃alkyl)carbamoyl, C₂₋₃alkanoyl and C₁₋₃alkoxycarbonyl) or 1-R¹⁰ᵃbut-2-en-4-yl, 1-R¹⁰ᵃpent-2-en-4-yl or 2-R¹⁰ᵃpent-3-en-5-yl (wherein $R^{10a}$ is a 5 or 6 membered saturated heterocyclic group with one or two heteroatoms, of which Eone is N and the other is selected independently from O, S and N, which heterocyclic group is linked to the alkenyl group through a nitrogen atom and which heterocyclic group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl)carbamoyl, $C_{2-3}$alkanoyl and $C_{1-3}$alkoxycarbonyl);

3) 1-$R^{11a}$prop-1-yn-3-yl, 1-$R^{11a}$but-2-yn-4-yl, 1-$R^{11a}$but-1-yn-3-yl, 1-$R^{11a}$pent-2-yn-4-yl or 2-$R^{11a}$pent-3-yn-5-yl (wherein $R^{11a}$ is a 5 or 6 membered saturated heterocyclic group with one or two heteroatoms, selected independently from O, S and N, which heterocyclic group is linked to the alkynyl group through a carbon atom and which heterocyclic group may bear one or two substituents selected from oxo; hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl)carbamoyl, $C_{2-3}$alkanoyl and $C_{1-3}$alkoxycarbonyl) or 1-$R^{12a}$but-2-yn-4-yl, 1-$R^{12a}$pent-2-yn-4-yl or 2-$R^{12a}$pent-3-yn-5-yl (wherein $R^{12a}$ is a 5 or 6 membered saturated heterocyclic group with one or two heteroatoms, of which one is N and the other is selected independently from O, S and N, which heterocyclic group is linked to the alkynyl group through a nitrogen atom and which heterocyclic group may bear one or two substituents selected from oxo, hydroxy, halogeno, $C_{1-3}$alkyl, $C_{2-3}$hydroxyalkyl, $C_{1-3}$alkoxy, carbamoyl, $C_{1-3}$alkylcarbamoyl, N,N-di($C_{1-3}$alkyl) carbamoyl, $C_{2-3}$alkanoyl and $C_{1-3}$alkoxycarbonyl);

4) $C_{2-3}$alkyl$X^{2a}C_{2-3}$alkyl$X^{3a}R^{13a}$ (wherein $X^{2a}$ and $X^{3a}$ which may be the same or different each represents —O—, —S—, —SO—, —SO$_2$—, —NR$^{14a}$CO—, or —NR$^{15a}$— (wherein $R^{14a}$ and $R^{15a}$ each independently represents hydrogen, $C_{1-2}$alkyl or $C_{1-2}$alkoxyethyl) and $R^{13a}$ represents hydrogen or $C_{1-3}$alkyl);

5) $C_{2-3}$alkyl$X^{4a}$COR$^{16a}$ (wherein $X^{4a}$ represents —O— or —NR$^{17a}$— (wherein $R^{17a}$ represents hydrogen $C_{1-3}$alkyl or $C_{1-2}$alkoxyethyl) and $R^{16a}$ represents —NR$^{18a}$R$^{19a}$ or —OR$^{20a}$ (wherein $R^{18a}$, $R^{19a}$ and $R^{20a}$ which may be the same or different each represents hydrogen, $C_{1-4}$alkyl or $C_{1-2}$alkoxyethyl));

6) $C_{2-3}$alkyl$X^{5a}R^{21a}$ (wherein $X^{5a}$ represents carbonyl, —O—, —S—, —SO—, —SO$_2$—, —NR$^{22a}$CO—, —NR$^{23a}$SO$_2$— or —NR$^{24a}$— (wherein $R^{22a}$, $R^{23a}$ and $R^{24a}$ each independently represents hydrogen, $C_{1-2}$alkyl or $C_{1-2}$alkoxyethyl) and $R^{21a}$ represents a group selected from cyclopentyl, cyclohexyl, pyrrolidinyl and piperidinyl which group is linked to $X^{5a}$ through a carbon atom and which group may carry one substituent selected from oxo, hydroxy, halogeno, $C_{1-2}$alkyl, $C_{1-2}$hydroxyalkyl, $C_{1-2}$alkoxy, carbamoyl, $C_{1-2}$alkylcarbamoyl, N,N-di($C_{1-2}$alkyl) carbamoyl, acetyl and $C_{1-2}$alkoxycarbonyl or $R^{21a}$ is $C_{1-3}$alkyl with the proviso that when $R^{21a}$ is $C_{1-3}$alkyl, $X^{5a}$ is —S—, —SO—, —SO$_2$— or —NR$^{23a}$SO$_2$—); and 7) $C_{1-2}$alkoxy$C_{2-3}$alkyl provided that $X^{1a}$ is —S—;

8) $C_{2-3}$alkyl$X^{6a}C_{2-3}$alkyl$R^{25a}$ (wherein $X^{6a}$ represents —O—, —S—, —SO$_2$—, —SO—, —NR$^{26a}$CO—, —NR$^{27a}$SO$_2$— or —NR$^{28a}$— (wherein $R^{26a}$, $R^{27a}$ and $R^{28a}$ each independently represents hydrogen, $C_{1-2}$alkyl or $C_{1-2}$alkoxyethyl) and $R^{25a}$ represents a 5 or 6 membered saturated heterocyclic group with one or two heteroatoms, selected independently from O, S and N, which heterocyclic group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl) carbamoyl, $C_{2-3}$alkanoyl, and $C_{1-3}$alkoxycarbonyl);

9) $C_{2-3}$alkyl$R^{29a}$ (wherein $R^{29a}$ is piperazin-1-yl which bears at least one substituent selected from acetyl, $C_{1-2}$alkoxycarbonyl, $C_{1-2}$hydroxyalkyl and CONR$^{30a}$R$^{31a}$ (wherein $R^{30a}$ and $R^{31a}$ each independently represents hydrogen or $C_{1-2}$alkyl);

10) $C_{2-3}$alkyl$R^{32a}$ (wherein $R^{32a}$ is morpholino which may bear one or two substituents selected from oxo, $C_{1-2}$alkyl, $C_{1-2}$hydroxyalkyl, carbamoyl, $C_{1-2}$alkylcarbamoyl, N,N-di($C_{1-2}$alkyl)cabamoyl, acetyl and $C_{1-2}$alkoxycarbonyl) with the proviso that when $R^{4a}$ is $C_{2-3}$alkyl$R^{32a}$, $X^{1a}$ is —S— or —NR$^{6a}$SO$_2$— (wherein $R^{6a}$ is as defined hereinbefore); and 11) $C_{2-3}$alkyl$R^{33a}$ (wherein $R^{33a}$ is morpholino which bears at least one and optionally two substituents selected from oxo, $C_{1-2}$alkyl, $C_{1-2}$hydroxyalkyl, carbamoyl, $C_{1-2}$alkylcarbamoyl, N,N-di($C_{1-2}$alkyl) carbamoyl, acetyl and $C_{1-2}$alkoxycarbonyl); and an additional value of $R^{4a}$ is $C_{2-3}$alkly$X^{2a}$methyl$X^{3a}R^{13a}$ (wherein $X^{2a}$ and $X^{3a}$ are as defined hereinbefore and $R^{13a}$ represents hydrogen or $C_{1-3}$alkyl);] and salts thereof.

Preferred compounds of the present invention, by virtue of their substantially equivalent activity against VEGF and EGF receptor tyrosine kinases include:

4-(4-chloro-2-fluoroanilino)-7-(1,3-dioxolan-2-ylmethoxy)-6-methoxyquinazoline, 4-(4-chloro-2-fluoroanilino)-6-methoxy-7-(4-morpholinobut-2-yn-1-yloxy)quinazoline, (E)-4-(4-chloro-2-fluoroanilino)-6-methoxy-7-(4-morpholinobut-2-en-1-yloxy)quinazoline, 4-(4-chloro-2-fluoroanilino)-7-(3-(2,6-dimethylmorpholino)propoxy)-6-methoxyquinazoline, 4-(4-chloro-2-fluoroanilino)-6-methoxy-7-(3-([N-methyl-N-methylsulphonyl]amino)propoxy) quinazoline, 7-(2-[N-tert-butoxycarbonylamino]ethoxy)-4-(4-chloro-2-fluoroanilino)-6-methoxyquinazoline, 4-(4-bromo-2-fluoroanilino)-6-methoxy-7-(3-([N-methyl-N-methylsulphonyl]amino)propoxy) quinazoline, 4-(4-chloro-2-fluoroanilino)-6-methoxy-7-(2-2-oxoimidazolidin-1-yl)ethoxy)quinazoline, 4-(4-chloro-2-fluoroanilino)-6-methoxy-7-(2-(3-oxomorpholino)ethoxy)quinazoline and 4-(4-bromo-2-fluoroanilino)-6-methoxy-7-(2-(3-oxomorpholino)ethoxy)quinazoline and salts thereof especially hydrochloride salts thereof.

More preferred compounds of the present invention, by virtue of their substantially equivalent activity against VEGF and EGF receptor tyrosine kinases include:

4-(4-chloro-2-fluoroanilino-6-methoxy-7-(2-thiomorpholinoethoxy)quinazoline, (S)-4-(4-bromo-2-fluoroanilino)-7-(3-(2-carbamoylpyrrolidin-1-yl)propoxy)-6-methoxyquinazoline, 4-(4-chloro-2-fluoroanilino)-6-methoxy-7-(3-(2oxopyrrolidin-1-yl)propoxy)quinazoline, 4-(4-chloro-2-fluoroanilino)-6-methoxy-7-(2-(2-oxopyrrolidin-1-yl)ethoxy)quinazoline, (S)-7-(3-(2-carbamoylpyrrolidin-1-yl)propoxy)-4-(4-chloro-2-fluoroanilino)-6-methoxyquinazoline, 4-(4-chloro-2-fluoroanilino)-6-methoxy-7-(2-(2-morpholinoethoxy)ethoxy)quinazoline and 4-(4-bromo-2-fluoroanilino)-6-methoxy-7-(3-(2-oxopyrrolidin-1-yl)propoxy)quinazoline and salts thereof especially hydrochloride salts thereof.

Particularly preferred compounds of the present invention, by virtue of their substantially equivalent activity against VEGF and EGF receptor tyrosine kinases include:

4-(4-chloro-2-fluoroanilino)-6-methoxy-7-(2-(2-methoxyethoxy)ethoxy)quinazoline and 4-(4-chloro-2-fluoroanilino)-6-methoxy-7-(1-methylpiperidin-3-yl)methoxyquinazoline and salts thereof especially hydrochloride salts thereof.

Additional particularly preferred compounds of the present invention, by virtue of their substantially equivalent activity against VEGF and EGF receptor tyrosine kinases include:

4-(4-bromo-2-fluoroanilino)-7-(3-(1,1-dioxothiomorpholino)propoxy)-6-methoxyquinazoline, 4-(4-bromo-2-fluoroanilino)-6-methoxy-7-(2-(2-methoxyethoxy)ethoxy)quinazoline, 4-(4-chloro-2-fluoroanilino)-6-methoxy-7-(2-(2-pyrrolidin-1-ylethoxy)ethoxy)quinazoline, 4-(4-chloro-2-fluoroanilino)-6-methoxy-7-(2-(2-[4-methylpiperazin-1-yl]ethoxy)ethoxy)quinazoline, 4-(4-chloro-2-fluoroanilino)-6-methoxy-7-(3-morpholinopropylthio)quinazoline, 4-(4-chloro-2-fluoroanilino)-6-methoxy-7-(2-([N-methyl-N-methoxyacetyl]amino)ethoxy)quinazoline and 4-(4-bromo-2-fluoroanilino)-6-methoxy-7-(2-(2-oxopyrrolidin-1-yl)ethoxy)quinazoline and salts thereof especially hydrochloride salts thereof.

Especially preferred compounds of the present invention, by virtue of their substantially equivalent activity against VEGF and EGF receptor tyrosine kinases include:

(E)-4-(4-chloro-2-fluoroanilino)-6-methoxy-7-(4-(pyrrolidin-1-yl)but-2-en-1-yloxy)quinazoline, 4-(4-chloro-2-fluoroanilino)-6-methoxy-7-(3-(methylsulphonyl)propoxy)quinazoline, (S)-4-(4-chloro-2-fluoroanilino)-6-methoxy-7-(1-methylpiperidin-3-yl)methoxyquinazoline and (R)-4-(4-chloro-2-fluoroanilino)-6-methoxy-7-(1-methylpiperidin-3-yl)methoxyquinazoline and salts thereof especially hydrochloride salts thereof, of which 4-(4-chloro-2-fluoroanilino)-6-methoxy-7-(3-(methylsulphonyl)propoxy)quinazoline and salts thereof especially hydrochloride salts thereof, is more especially preferred.

In a particular aspect of the present invention preferred compounds are:

4-(3-acetoxy-4-methylanilino)-6-methoxy-7-2-methoxyethoxy)quinazoline 4-(4-chloro-2-fluoroanilino)-7-(2-(1,3-dioxolan-2-yl)ethoxy)-6-methoxyquinazoline 4-(4-chloro-2-fluoroanilino)-6-methoxy-7-(2-(pyrrolidin-1-yl)ethoxy)quinazoline 4-(4-chloro-2-fluoroanilino)-6-methoxy-7-(3-(pyrrolidin-1-yl)propoxy)quinazoline 4-(4-chloro-2-fluoroanilino)-7-(1,3-dioxolan-2-ylmethoxy)-6-methoxyquinazoline 4-(4-chloro-2-fluoroanilino)-6-methoxy-7-(2-thiomorpholinoethoxy)quinazoline and salts thereof especially the hydrochloride salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms. The term "alkoxy" as used herein, unless stated otherwise includes "alkyl" —O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl" —O—groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C=O$, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–5 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–5 carbon atoms, preferably 3–5 carbon atoms.

In formula I, as hereinbefore defined, hydrogen will be present at positions 2 and 8 of the quinazoline group.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^7CO$—, it is the nitrogen atom bearing the $R^7$ group which is attached to the quinazoline ring and the carbonyl (CO) group is attached to $R^4$, whereas when $X^1$ is, for example, a group of formula —$CONR^8$—, it is the carbonyl group which is attached to the quinazoline ring and the nitrogen atom bearing the $R^8$ group is attached to $R^4$. A similar convention applies to the other two atom $X^1$ linking groups such as —$NR^{10}SO_2$— and —$SO_2NR^9$—. When $X^1$ is —$NR^{11}$— it is the nitrogen atom bearing the $R^{11}$ group which is linked to the quinazoline ring and to $R^4$. An analogous convention applies to other groups, thus when $R^4$ is, for example, a group of the formula $C_{1-5}$alkyl$X^5R^{27}$ and $X^5$ is a group —$NR^{28}CO$—, it is the nitrogen atom bearing the $R^{28}$ group which is attached to the alkyl chain which is attached to the quinazoline ring and the carbonyl (CO) group is attached to $R^{27}$, whereas when $X^5$ is, for example, a group of formula —$CONR^{29}$—, it is the carbonyl group which is attached to the alkyl chain which is attached to the quinazoline ring and the nitrogen atom bearing the $R^{29}$ group is attached to $R^{27}$. It is further to be understood that when $X^1$ represents —$NR^{11}$— and $R^{11}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^4$ is, for example, a group of formula $C_{1-5}$alkyl$X^2C_{1-5}$alkyl$X^3R^{16}$, it is the terminal $C_{1-5}$alkyl moiety which is bound to $X^1$, similarly when $R^4$ is, for example, a group of formula $C_{2-5}$alkenyl$R^{14}$ it is the $C_{2-5}$alkenyl moiety which is bound to $X^1$ and an analgous convention applies to other groups. When $R^4$ is a group 1-$R^{33}$prop-1-en-3-yl it is the first carbon to which the group $R^{33}$ is attached and it is the third carbon which is linked to $X^1$, similarly when $R^4$ is a group 2-$R^{33}$pent-3-en-5-yl it is the second carbon to which the group $R^{33}$ is attached and it is the fifth carbon which is linked to $X^1$, and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications, Publication Nos. 0520722, 0566226, 0602851 and 0635498. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (g) and (i) to (v) constitute further features of the present invention.

Synthesis of Compounds of Formula I (a) Compounds of the formula I and salts thereof may be prepared by the reaction of a compound of the formula III:

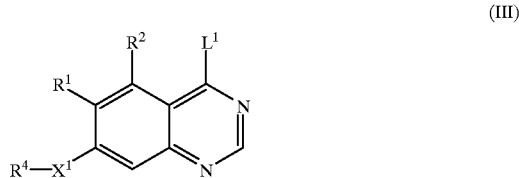

(III)

(wherein $R^1$, $R^2$, $X^1$ and $R^4$ are as defined hereinbefore and $L^1$ is a displaceable moiety), with a compound of the formula IV:

(IV)

(wherein $R^3$ and m are as defined hereinbefore) whereby to obtain compounds of the formula I and salts thereof. A convenient displaceable moiety $L^1$ is, for example, a halogeno, alkoxy (preferably $C_{1-4}$alkoxy), aryloxy or sulphonyloxy group, for example a chloro, bromo, methoxy, phenoxy, methanesulphonyloxy or toluene-4-sulphonyloxy group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide or sodium bis(trimethylsilyl)amide. The reaction is preferably effected in the presence of an inert solvent or diluent, for example an alkanol or ester such as methanol, ethanol, 2-propanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 150° C., preferably in the range 20 to 80° C.

The compound of the invention may be obtained from this process in the form of the free base or alternatively it may be obtained in the form of a salt with the acid of the formula H-L¹ wherein L¹ has the meaning defined hereinbefore. When it is desired to obtain the free base from the salt, the salt may be treated with a base as defined hereinbefore using a conventional procedure.

(b) Where the group of formula IIa:

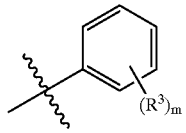

(IIa)

(wherein R³ and m are as hereinbefore defined) represents a phenyl group carrying one or more hydroxy groups, a compound of the formula I and salts thereof can be prepared by the deprotection of a compound of formula V:

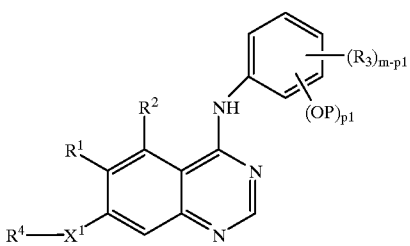

(V)

(wherein X¹, m, R¹, R², R³ and ⁴ are as hereinbefore defined, P represents a phenolic hydroxy protecting group and pl is an integer from 1 to 5 equal to the number of protected hydroxy groups and such that m-pl is equal to the number of R³ substituents which are not protected hydroxy). The choice of phenolic hydroxy protecting group P is within the standard knowledge of an organic chemist, forexample those included in standard texts such as "Protective Groups in Organic Synthesis" T. W. Greene and R. G. M. Wuts, 2nd Ed. Wiley 1991, including ethers (for example, methyl, methoxymethyl, allyl and benzyl and benzyl substituted with up to two substituents selected from $C_{1-4}$alkoxy and nitro), silyl ethers (for example, t-butyldiphenylsilyl and t-butyldimethylsilyl), esters (for example, acetate and benzoate) and carbonates (for example, methyl and benzyl and benzyl substituted with up to two substituents selected from $C_{1-4}$alkoxy and nitro). The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group P is acetate, the transformation may conveniently be effected by treatment of the quinazoline derivative with a base as defined hereinbefore and including ammonia, and its mono and di-alkylated derivatives, preferably in the presence of a protic solvent or co-solvent such as water or an alcohol, for example methanol or ethanol. Such a reaction can be effected in the presence of an additional inert solvent or diluent as defined hereinbefore and at a temperature in the range 0 to 50° C., conveniently at about 20° C.

(c) Production of those compounds of formula I and salts thereof wherein the substituent X¹ is —O—, —S— or —NR¹¹— or —SO₂—, —CONR⁸— or —SO₂NR⁹— can be achieved by the reaction, conveniently in the presence of a base as defined hereinbefore, of a compound of the formula VI:

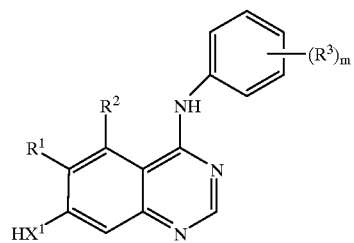

(VI)

(wherein m, X¹, R¹, R² and R³ are as hereinbefore defined) with a compound of formula VII:

R⁴—L¹ (VII)

(wherein R⁴ and L¹ are as hereinbefore defined); L¹ is a displaceable moiety for example a halogeno or sulphonyloxy group such as a bromo or methanesulphonyloxy group. Conveniently L¹ is a group O—⁺P(R⁵²)₃ (wherein R⁵² is butyl or phenyl) and in such cases the compound of formula VII is conveniently formed in situ. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(d) Compounds of the formula I and salts thereof may be prepared by the reaction of a compound of the formula VIII:

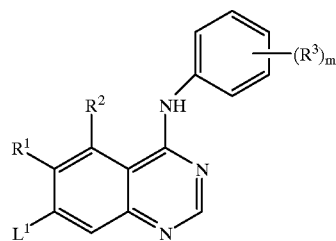

(VIII)

with a compound of the formula IX:

R⁴—X¹—H (IX)

(wherein L¹, R¹, R², R³, R⁴, m and X¹ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(e) Compounds of the formula I and salts thereof wherein $R^4$ is $C_{1-5}$alkyl$R^{53}$, [wherein $R^{53}$ is selected from one of the following three groups:
1) $X^7R^{27}$ (wherein $X^7$ represents —O—, —S—, —SO$_2$—, —NR$^{54}$CO—, —NR$^{55}$SO$_2$— or —NR$^{56}$— (wherein $R^{54}$, $R^{55}$ and $R^{56}$ each independently represents hydrogen, $C_{1-3}$alkyl or $C_{1-3}$alkoxy$C_{2-3}$alkyl) and $R^{27}$ is as defined hereinbefore); and
2) $X^8C_{1-5}$alkyl$X^3R^{16}$ (wherein $X^8$ represents —O—, —S—, —SO$_2$—, —NR$^{57}$CO—, —NR$^{58}$SO$_2$— or NR$^{59}$— (wherein $R^{57}$, $R^{58}$ and $R^{59}$ each independently represents hydrogen, $C_{1-3}$alkyl or $C_{1-3}$alkoxy$C_{2-3}$alkyl) and $X^3$ and $R^{16}$ are as defined hereinbefore); and
3) $X^9C_{1-5}$alkyl$R^{33}$ (wherein $X^9$ represents —O—, —S—, —SO$_2$—, —NR$^{60}$CO—, —NR$^{61}$SO$_2$— or NR$^{62}$— (wherein $R^{60}$, $R^{61}$ and $R^{62}$ each independently represents hydrogen, $C_{1-3}$alkyl or $C_{1-3}$alkoxy$C_{2-3}$alkyl) and $R^{33}$ is as defined hereinbefore);] may be prepared by reacting a compound of the formula X:

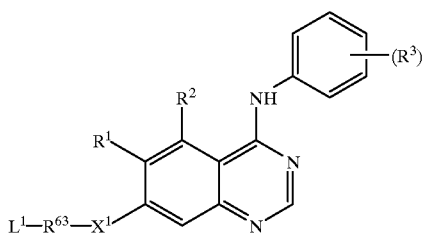

(X)

(wherein $L^1$, $X^1$, $R^1$, $R^2$, $R^3$ and m are as hereinbefore defined and $R^{63}$ is $C_{1-5}$alkyl) with a compound of the formula XI:

(XI)

(wherein $R^{53}$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Compounds of the formula I wherein $R^4$ is $C_{2-5}$alkyl$R^{45}$, (wherein $R^{45}$ is as defined hereinbefore), may be prepared by reacting a compound of formula X (wherein $R^{63}$ is $C_{2-5}$alkyl) with a compound of the formula XIa:

(XIa)

(wherein $R^{45}$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

(f) The production of those compounds of the formula I and salts thereof wherein the substituent $R^1$ is represented by —NR$^5$R$^6$, where one or both of $R^5$ and $R^6$ are $C_{1-3}$alkyl, may be effected by the reaction of compounds of formula I wherein the substituent $R^1$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature.

(g) The production of compounds of formula I and salts thereof wherein one or more of the substituents $R^1$, $R^2$ or $R^3$ is an amino group may be effected by the reduction of a corresponding compound of formula I wherein the substituent(s) at the corresponding position(s) of the quinazoline and/or aniline ring is tare a nitro group(s). The reduction may conveniently be effected as described in process (i) hereinafter. The production of a compound of formula I and salts thereof wherein the substituent(s) at the corresponding position(s) of the quinazoline and/or aniline ring is/are a nitro group(s) may be effected by the processes described hereinbefore and hereinafter in processes (a–e) and (i–v) using a quinazoline compound selected from the compounds of the formulae (I–XXVII) in which the substituent(s) at the corresponding position(s) of the quinazoline and/or aniline ring is/are a nitro group(s).

Synthesis of Intermediates (i) The compounds of formula III and salts thereof, constitute a further feature of the present invention. Such compounds in which $L^1$ is halogeno may for example be prepared by halogenating a compound of the formula XII:

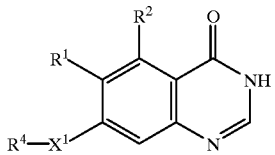

(XII)

(wherein $R^1$, $R^2$, $R^3$ and $X^1$ are as hereinbefore defined).

Convenient halogenating agents include inorganic acid halides, for example thionyl chloride, phosphorus(III) chloride, phosphorus(V)oxychloride and phosphorus(V) chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula XII and salts thereof which constitute a further feature of the present invention may for example be prepared by reacting a compound of the formula XIII:

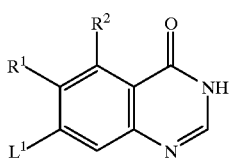

(XIII)

(wherein $R^1$, $R^2$ and $L^1$ are as hereinbefore defined) with a compound of the formula IX as hereinbefore defined.

The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

The compounds of formula XII and salts thereof may also be prepared by cyclising a compound of the formula XIV:

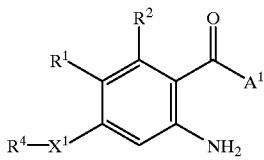

(XIV)

(wherein $R^1$, $R^2$, $R^4$ and $X^1$, are as hereinbefore defined, and $A^1$ is an hydroxy, alkoxy (preferably $C_{1-4}$alkoxy) or amino group) whereby to form a compound of formula XII or salt thereof. The cyclisation may be effected by reacting a compound of the formula XIV, where $A^1$ is an hydroxy or alkoxy group, with formamide or an equivalent thereof effective to cause cyclisation whereby a compound of formula XII or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XII may also be prepared by cyclising a compound of the formula XIV, where $A^1$ is an amino group, with formic acid or an equivalent thereof effective to cause cyclisation whereby a compound of formula XII or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethylether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof, which constitute a further feature of the present invention, may for example be prepared by the reduction of the nitro group in a compound of the formula XV:

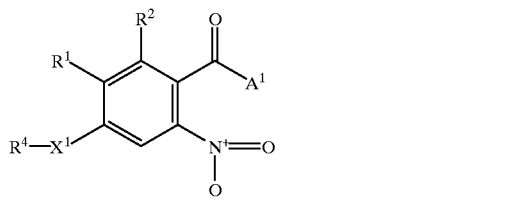

(XV)

(wherein $R^1$, $R^2$, $R^4$, $X^1$ and $A^1$ are as hereinbefore defined) to yield a compound of formula XIV as hereinbefore defined. The reduction of the nitro group may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C.

Compounds of the formula XV and salts thereof which constitute a further feature of the present invention, may for example be prepared by the reaction of a compound of the formula XVI:

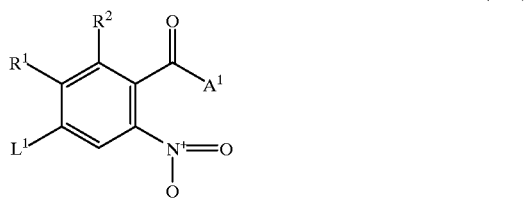

(XVI)

(wherein $R^1$, $R^2$, $L^1$ and $A^1$ are as hereinbefore defined) with a compound of the formula IX as hereinbefore defined to give a compound of the formula XV. The reaction of the compounds of formulae XVI and IX is conveniently effected under conditions as described for process (d) hereinbefore.

Compounds of formula XV and salts thereof, may for example also be prepared by the reaction of a compound of the formula XVII:

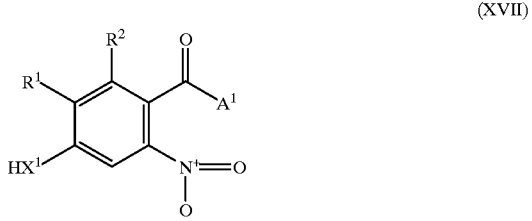

(XVII)

(wherein $R^1$, $R^2$, $X^1$ and $A^1$ are as hereinbefore defined with the proviso that $X^1$ is not —$CH_2$—) with a compound of the formula VII as hereinbefore defined to yield a compound of formula XV as hereinbefore defined. The reaction of the compounds of formulae XVII and VII is conveniently effected under conditions as described for process (c) hereinbefore.

The compounds of formula III and salts thereof may also be prepared for example by reacting a compound of the formula XVIII:

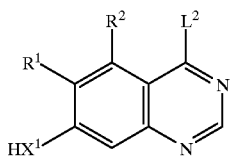

(XVIII)

(wherein $R^1$, $R^2$ and $X^1$ are as hereinbefore defined with the proviso that $X^1$ is not —$CH_2$— and $L^2$ represents a displaceable protecting moiety) with a compound of the formula VII as hereinbefore defined, whereby to obtain a compound of formula III in which $L^1$ is represented by $L^2$.

A compound of formula XVIII is conveniently used in which $L^2$ represents a phenoxy group which may if desired carry up to 5 substituents, preferably up to 2 substituents, selected from halogeno, nitro and cyano. The reaction may be conveniently effected under conditions as described for process (c) hereinbefore.

The compounds of formula XVIII and salts thereof as hereinbefore defined may for example be prepared by deprotecting a compound of the formula XIX:

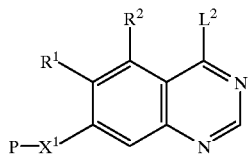

(XIX)

(wherein $R^1$, $R^2$, P, $X^1$ and $L^2$ are as hereinbefore defined with the proviso that $X^1$ is not —$CH_2$—). Deprotection may be effected by techniques well known in the literature, for example where P represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XII as hereinbefore defined, followed by introduction of halide to the compound of formula XII, thus obtained as hereinbefore defined, to yield a compound of formula III in which $L^1$ represents halogen.

(ii) The compounds of formula V and salts thereof, constitute a further feature of the present invention, and may for example be prepared by the reaction of a compound of formula III as hereinbefore defined with a compound of the formula XX:

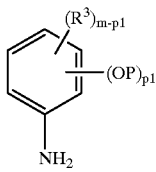

(XX)

(wherein $R^3$, m, p1 and P are as hereinbefore defined). The reaction may for example be effected as described for process (a) hereinbefore.

The compounds of formula V and salts thereof may also be prepared by reacting a compound of formula XXI:

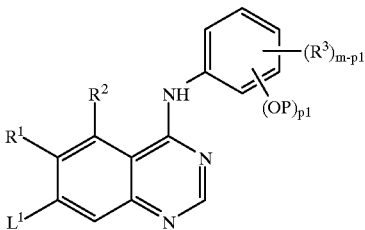

(XXI)

(wherein $R^1$, $R^2$, $L^1$, $R^3$, m, p1 and P are as hereinbefore defined) with a compound of formula IX as hereinbefore defined. The reaction may for example be effected as described for process (d) above.

The compounds of formula V and salts thereof may also be prepared by reacting a compound of formula XXII:

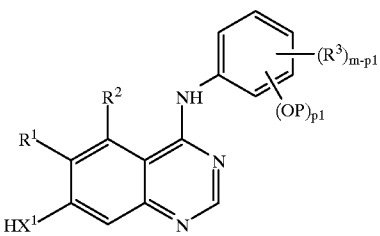

(XXII)

(wherein $R^1$, $R^2$, $R^3$, $X^1$, P, p1 and m are as hereinbefore defined with the proviso that $X^1$ is not —$CH_2$—) with a compound of the formula VII as hereinbefore defined. The reaction may for example be effected as described for process (c) hereinbefore.

The compounds of formula XXI and salts thereof may for example be prepared by reaction of a compound of formula XXIII:

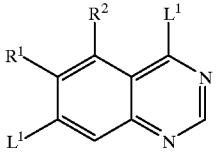

(XXIII)

(wherein $R^1$, $R^2$, and $L^1$ are as hereinbefore defined, and $L^1$ in the 4 and 7-positions may be the same or different) with a compound of the formula XX as hereinbefore defined. The reaction may be effected for example by a process as described in (a) above.

Compounds of the formula XXII and salts thereof may be made by reacting compounds of the formulae XIX and XX as hereinbefore defined, under conditions described in (a) hereinbefore, to give a compound of formula XXIV:

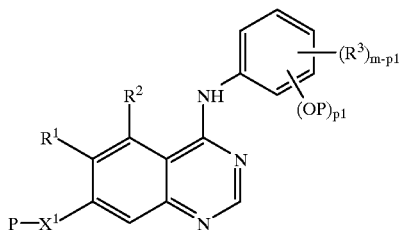

(XXIV)

(wherein $R^1$, $R^2$, $R^3$, P, $X^1$, p1 and m are as hereinbefore defined with the proviso that $X^1$ is not —CH$_2$—) and tie-in deprotecting the compound of formula XXIV for example as described in (i) above.

(iii) Compounds of the formula VI as hereinbefore defined and salts thereof may be made by deprotecting the compound of formula XXV:

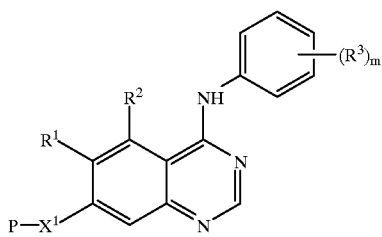

(XXV)

(wherein $R^1$, $R^2$, $R^3$, P, $X^1$ and m are as hereinbefore defined) by a process for example as described in (i) above.

Compounds of the formula XXV and salts thereof may be made by reacting compounds of the formulae XIX and IV as hereinbefore defined, under the conditions described in (a) hereinbefore, to give a compound of the formula XXV or salt thereof.

(iv) Compounds of the formula VIII and salts thereof as hereinbefore defined may be made by reacting compounds of the formulae XXIII and IV as hereinbefore defined, the reaction for example being effected by a process as described in (a) above.

(v) Compounds of the formula X as defined hereinbefore and salts thereof may for example be made by the reaction of a compound of formula VI as defined hereinbefore with a compound of the formula XXVI:

$L^1$—$R^{63}$—$L^1$     (XXVI)

(wherein $L^1$ and $R^{63}$ are as hereinbefore defined) to give a compound of the formula X. The reaction may be effected for example by a process as described in (c) above.

Compounds of the formula X and salts thereof may also be made for example by deprotecting a compound of the formula XXVII:

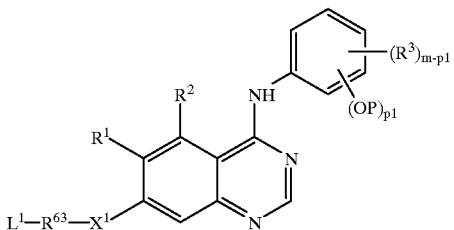

(XXVII)

(wherein $L^1$, $R^{63}$, $X^1$, $R^1$, $R^2$, $R^3$, P, m and p1 are as defined hereinbefore) by a process for example as described in (b) above.

Compounds of the formula XXVII and salts thereof may be made for example by reacting compounds of the formulae XXII and XXVI as defined hereinbefore, under the conditions described in (c) above.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel, for example, those of the formulae III, V, XII, XIV and XV, and these are provided as a further feature of the invention.

Intermediates of the formulae VIII, X, XXI, XXII, XXIV, XXV and XXVII are also provided as a further feature of the invention.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7A, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis($\beta$aminoethyl ether) N,N,N', N'tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 $\mu$l of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 $\mu$l of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 $\mu$l of diluted compound was transferred to wells in the washed assay plates. "Total" control wells contained 10% DMSO instead of compound. Twenty five microlitres of 40 mM manganese(II)chloride containing 8 $\mu$M adenosine-5'-triphosphate (ATP) was added to all test wells except "blank" control wells which contained manganese(II)chloride without ATP. To start the reactions 50 $\mu$l of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05–321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microlitres of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microlitres of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 $\mu$g/ml heparin+1 $\mu$g/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% carbon dioxide. On day 4 the cultures were pulsed with 1 $\mu$Ci/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5 $\mu$g/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square metre body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid artritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF especially those tumours which are significantly dependent on VEGF for their growth and spread, including for example, certain tumours of the colon, breast, prostate, lung, vulva and skin.

In addition to their use in therapeutic medicine the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, muitiplet; br, broad; q, quartet;

(vii) intermediates were not generally fully characterised and purity was assessed by thin layer chromatography (TLC), high-performance liquid chromatography (HPLC), infra-red (IR) or NMR analysis;

(viii) the following abbreviations have been used:
DMF N,N-dimethylformamide
DMSO dimethylsulphoxide
THF tetrahydrofuran
TFA trifluoroacetic acid
NMP 1-methyl-2-pyrrolidinone.]

EXAMPLE 1

Potassium carbonate (2.2 g, 16 mmol) was added to a solution of 4-3-acetoxy-4-methylanilino)-7-hydroxy-6-methoxyquinazoline (1.51 g, 4 mmol) in DMF (30 ml) and the mixture stirred for 15 minutes. 2-Bromoethyl methyl ether (667 mg, 4.8 mmol) was then added dropwise. The mixture was stirred for 1 hour at ambient temperature, then heated at 60° C. for 17 hours and finally allowed to cool. The insoluble material was removed by filtration and the filter pad washed with DMF. The filtrate was partitioned between ethyl acetate and water, the organic layer was separated, washed with brine, dried (MgSO$_4$) and the solvent removed by evaporation. The residue was purified by column chromatography eluting with methylene chloride/methanol (95/5 followed by 93/7). The purified product was triturated with ether to give 4-(3acetoxy-4-methylanilino)-6-methoxy-7-(2-methoxyethoxy)quinazoline (1.34 g, 84%) as a white powder.

m.p. 180–183° C.; $^1$H NMR Spectrum: (CDCl$_3$) 2.16(s, 3H); 2.34(s, 3H); 3.47(s, 3H); 3.87(t, 2H); 3.99(s, 3H); 4.31(t, 2H); 6.98(s, 1H); 7.21(d, 1H); 7.24(d, 1H); 7.42(d, 1H); 7.50(s, 1H); 8.64(s, 1H); MS-ESI: 420 [MNa]$^+$; Elemental analysis: Found C, 63.1; H, 6.1; N, 10.4; C$_{21}$H$_{23}$N$_3$O$_5$ Requires C, 63.5; H, 5.8; N, 10.6%.

The starting material was prepared as follows:

A mixture of 2-amino-4-benzyloxy-5-methoxybenzamide (J. Med. Chem. 1977, vol 20, 146–149, 10 g, 0.04 mol) and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The mixture was evaporated, water was added to the residue, the solid was filtered off, washed with water and dried (MgSO$_4$). Recrystallisation from acetic acid gave 7-benzyloxy-6-methoxy-3,4-dihydroquinazolin-4-one (8.7 g, 84%).

A mixture of 7-benzyloxy-6-methoxy-3,4-dihydroquinazolin4-one (2.82 g, 0.01 mol), thionyl chloride (40 ml) and DMF (0.28 ml) was stirred and heated to reflux for 1 hour. The mixture was evaporated, the residue was taken up in toluene and evaporated to dryness to give 7-benzyloxy-4-chloro-6-methoxyquinazoline (3.45 g).

Acetic anhydride (1.9 ml, 20.3 mmol) was added to a mixture of 2-methyl-5-nitrophenol (2.5 g, 16.3 mmol) and 1M aqueous sodium hydroxide (24.5 ml) at ambient temperature. The mixture was stirred for 40 minutes, the solid was removed by filtration and the filtrate extracted with ethyl acetate. The organic layers were combined, washed with an aqueous saturated sodium chloride solution, dried (MgSO$_4$) and evaporated to yield 2-acetoxy-4-nitrotoluene (3.1 g, 100%). A mixture of this material (3.1 g, 15.9 mmol) and 10% palladium-on-charcoal catalyst (0.12 g) in ethyl acetate (50 ml) was stirred at ambient temperature under an atmosphere of hydrogen for 2 hours. The catalyst was removed by filtration and the filtrate evaporated to give 3-acetoxy-4-methylaniline (2.45 g, 94%).

A mixture of 7-benzyloxy-4-chloro-6-methoxyquinazoline (2.18 g, 7.25 mmol), 3-acetoxy-4-methylaniline (1.32 g, 8 mmol) and 2-propanol (50 ml) was stirred and heated to reflux for 1 hour. The mixture was cooled to ambient temperature. The precipitate was collected by filtration, washed with 2-propanol and ether to give 4-(3-acetoxy-4-methylanilino)-7-benzyloxy-6-methoxyquinazoline. A mixture of 4-(3-acetoxy-4-methylanilino)-7-benzyloxy-6-methoxyquinazoline (2.68 g, 5.75 mmol), 10% palladium-on-charcoal catalyst (0.27 g) in methanol (50 ml), DMF (12 ml) and trichloromethane (50 ml) was stirred at ambient temperature under 1.5 atmospheres of hydrogen for 30 minutes. The catalyst was removed by filtration and the filtrate evaporated. The residual solid was triturated in ether, collected by filtration and dried under vacuum at 50° C. to give 4-(3-acetoxy-4-methylanilino)-7-hydroxy-6-methoxyquinazoline (2.1 g, 100%).

EXAMPLE 2

A solution of 2-(2-bromoethyl)-1,3-dioxolane (258 mg, 1.4 mmol) in DMF (0.5 ml) was added to a mixture of 4-(4-chloro-2-fluoroanilino)-7-hydroxy-6-methoxyquinazoline (329 mg, 1.02 mmol) and potassium carbonate (264 mg, 2 mmol) in DMF (2 ml). The mixture was heated at 100° C. for 3 hours and allowed to cool. The volatiles were removed by evaporation, and the residue partitioned between aqueous sodium hydrogen carbonate solution and methylene chloride. The organic phase was separated and passed through phase separating paper. The solvent was removed by evaporation, and the residue was purified by column chromatography eluting with methylene chloride/methanol (95/5) to give 4-(4-chloro-2-fluoroanilino)-7-(2-(1,3-dioxolan-2-yl)ethoxy)methoxyquinazoline (71 mg, 17%).

¹H NMR Spectrum: (DMSOd₆) 2.1(m, 2H); 3.8(m, 2H); 3.95(m, 5H); 4.25(t, 2H); 5.05(t, 1H); 7.18(s, 1H); 7.3(m, 1H); 7.55(m, 2H); 7.8(s, 1H); 8.35(s, 1H); 9.5(s, 1H); MS-ESI: 420 [MH]⁺; Elemental analysis: Found C, 57.4; H, 4.7; N, 9.1; $C_{20}H_{19}N_3O_4ClF$ Requires C, 57.2; H, 5.6; N, 10.0%.

The starting material was prepared as follows:

A solution of 7-benzyloxy-4chloro-6-methoxyquinazoline (1.2 g, 4 mmol), (prepared as described for the starting material in Example 1), and 4-chloro-2-fluoroaniline (4441 μl, 4 mmol) in 2-propanol (40 ml) was refluxed for 1.5 hours. After cooling, the precipitate was collected by filtration, washed with 2-propanol then ether and dried under vacuum to give 7-benzyloxy-4-(4-chloro-2-fluoroanilino)-6-methoxyquinazoline hydrochloride (1.13 g, 64%). m.p. 239–242° C.

¹H NMR Spectrum: (DMSOd₆) 4.0(s, 3H); 5.36(s, 2H); 7.39–7.52(m, 9H); 8.1(s, 1H); 8.75(s, 1H); MS-ESI: 410 [MH]⁺; Elemental analysis: Found C, 59.2; H, 4.3; N, 9.4; $C_{22}H_{17}N_3O_2ClF$ 1 HCl Requires C, 59.2; H, 4.1; N, 9.41%.

A solution of 7-benzyloxy-4-(4-chloro-2-fluoroanilino)-6-methoxyquinazoline hydrochloride (892 mg, 2 mmol) in TFA (10 ml) was refluxed for 50 minutes. After cooling, the mixture was poured onto ice. The precipitate was collected by filtration, dissolved in methanol (10 ml) and basified to pH11 with aqueous ammonia. After concentration by evaporation, the solid product was collected by filtration, washed with water then ether and dried under vacuum to give 4-(4-chloro-2-fluoroanilino)-7-hydroxy-6-methoxyquinazoline as a yellow solid (460 mg, 72%). m.p. 141–143° C.

¹H NMR Spectrum: (DMSOd₆) 3.95(s, 3H); 7.05(s, 1H); 7.35(d, 1H); 7.54–7.59(m, 2H); 7.78(s, 1H); 8.29(s, 1H); MS-ESI: 320–322 [MH]⁺.

EXAMPLE 3

1-2-Chloroethyl)pyrrolidine hydrochloride (200 mg, 1.2 mmol) was added to a mixture of 4-(4-chloro-2-fluoroanilino)-7-hydroxy-6-methoxyquinazoline (403 mg, 1.26 mmol), (prepared as described for the starting material in Example 2), and potassium carbonate (650 mg, 4.7 mmol) in DMF (4 ml). The mixture was heated to 100° C. and further portions of 1-(2-chloroethyl)pyrrolidine hydrochloride (800 mg in total) were added periodically over 4 hours while the reaction mixture was maintained at 100° C. The reaction was then allowed to cool and volatiles were removed by evaporation. The residue was partitioned between methylene chloride and water, separated and the organic phase passed through phase separating paper. Column chromatography eluting with methylene chloride/methanol (95/5) gave 4-(4-chloro-2-fluoroanilino)-6-methoxy-7-(2-(pyrrolidin-1-yl)ethoxy)quinazoline (50 mg, 10%).

¹H NMR Spectrum: (DMSOd₆) 1.8–2.1(m, 4H); 3.1(m, 2H); 3.55–3.7(m, 4H); 4.05(s, 3H); 4.6(t, 2H); 7.4(m, 2H); 7.58(d, 1H); 7.65(dt, 1H); 8.5(s, 1H); 8.8(s, 1H); MS-ESI: 417 [MH]⁻. Elemental analysis: Found C, 60.2; H, 5.4; N, 12.3; $C_{21}H_{22}N_4O_2ClF$ Requires C, 60.5; H, 5.3; N, 13.4%.

EXAMPLE 4

A solution of 1-(3-chloropropyl)pyrrolidine (230 mg, 0.96 mmol) was added to 4-(4-chloro-2-fluoroanilino)-7-hydroxy-6-methoxyquinazoline (295 mg, 0.92 mmol), (prepared as described for the starting material in Example 2), and potassium carbonate (130 mg, 0.94 mmol) in DMF (8 ml). The mixture was heated at 100° C. for 90 minutes and allowed to cool. The volatiles were removed by evaporation and the residues were partitioned between water and methylene chloride. The organic phase was separated and passed through phase separating paper, and the solvent was removed under reduced pressure. The residue was dissolved in acetone and hydrogen chloride in ether (2 ml of a 1M solution, 2 mmol) was added. The mixture was stirred at ambient temperature for 30 minutes and the resulting precipitate was collected by filtration and dried to give 4-(4-chloro-2-fluoroanilino)-6-methoxy-7-(3-(pyrrolidin-1-yl)propoxy)quinazoline hydrochloride hydrate (320 mg, 67%).

¹H NMR Spectrum: (DMSOd₆) 1.8–2.0(m, 6H); 3–3.6(m, 6H); 4.05(s, 3H); 4.3(t, 2H); 7.4(m, 2H); 7.55(d, 1H); 7.6(m, 1H); 8.4(s, 1H); 8.8(s, 1H); MS-ESI: 431 [MH]⁺; Elemental analysis: Found C, 51.0; H, 5.9; N, 10.6; $C_{22}H_{24}N_4O_2ClF$ 1.8 H₂O 1.5 HCl Requires C, 51.0; H, 5.7; N, 10.8%.

The starting material was prepared as follows:

Pyrrolidine (3 g, 42 mmol) was added to a solution of 1-bromo-3-chloropropane (3.2 g, 20 mmol) in toluene (20 ml). The mixture was stirred at ambient temperature overnight and then heated at 60° C. for 4 hours. The mixture was allowed to cool and the precipitate removed by filtration. The bulk of toluene was removed by evaporation to give an oil. ¹H NMR indicated the oil was a 1:1 mol:mol mixture of toluene and 1-(3-chloropropyl)pyrrolidine. This material was used without further purification.

¹H NMR Spectrum: (CDCl₃) 1.75(m, 4H); 2.0(q, 2H); 2.35(s, 3H, toluene): 2.45–2.6(m, 6H); 3.6(t, 2H); 7.15–7.3 (m, 5H, toluene).

EXAMPLE 5

A solution of 2-(2-methoxyethoxy)ethanol (90 mg, 0.75 mmol) in methylene chloride (1 ml) was added to tributylphosphine (320 mg, 1.58 mmol) and 4-(4-chloro-2-fluoroanilino)-7-hydroxy-6-methoxyquinazoline (200 mg, 0.63 mmol), (prepared as described for the starting material in Example 2), in methylene chloride (6 ml) at 0° C. under argon. To the resulting mixture 1,1'-(azodicarbonyl) dipiperidine (400 mg, 1.6 mmol) was added in portions. The mixture was allowed to warm to ambient temperature and stirred under argon for 2 hours. Ether (5 ml) was added, and the precipitated solids were removed by filtration. The volatiles were removed from the filtrate by evaporation, and the residue was purified by column chromatography eluting with methylene chloride/methanol (90/10). The resulting partially purified product was dissolved in acetone, and ethereal hydrogen chloride (0.6 ml of a 1M solution, 0.6 mmol) added. The resulting precipitated product was collected by filtration and dried to give 4-(4-chloro-2-fluoroanilino)-6-methoxy-7-(2-(2-methoxyethoxy)ethoxy) quinazoline hydrochloride (128 mg, 44%).

¹H NMR Spectrum: (DMSOd₆) 3.25(s, 3H); 3.45(dd, 2H); 3.6(dd, 2H); 3.8(t, 2H); 4.0(s, 3H); 4.3(t, 2H); 7.4(s, 1H); 7.45(dd, 1H); 7.55–7.7(m, 2H); 8.3(s, 1H); 8.75(s, 1H); 11.5(br s, 1H); MS-ESI: 422 [MH]⁺; Elemental analysis: Found C, 52.3; H, 4.7; N, 9.1; $C_{20}H_{21}N_3O_4ClF$ 1 HCl Requires C, 524; H, 4.8; N, 9.2%.

EXAMPLE 6

A solution of 2-(bromomethyl)-1,3-dioxolane (190 mg, 1.1 mmol) in DMF (1 ml) was added to 4-(4-chloro-2-fluoroanilino)-7-hydroxy-6-methoxyquinazoline (258 mg, 0.81 mmol), (prepared as described for the starting material in Example 2), and potassium carbonate (200 mg, 1.5 mmol)

in DMF (2 ml). The mixture was heated at 100° C. for 4 hours and then allowed to cool. The volatiles were removed by evaporation and the residue partitioned between water and methylene chloride. The organic phase was separated, passed through phase separating paper and purified by column chromatography eluting with methylene chloride/methanol (95/5) to give 4-(4-chloro-2-fluoroanilino)-7-(1,3-dioxolan-2-ylmethoxy)-6-methoxyquinazoline (130 mg, 38%).

$^1$H NMR Spectrum: (DMSOd$_6$) 3.8–4.1(m, 7H); 4.15(d, 2H); 5.30(t, 1H); 7.22(s, 1H); 7.30(m, 1H); 7.55(m, 2H); 7.80(s, 1H); 8.35(s, 1H); 9.55(s, 1H). Also contained 0.3 methanol. MS-ESI: 406 [MH]$^+$; Elemental analysis: Found C, 55.1; H, 4.5; N, 9.5; $C_{19}H_{17}N_3O_4ClF$ 0.3 $H_2O$ Requires C, 55.1; H, 4.5; N, 10.0%. 0.3 Methanol.

EXAMPLE 7

A mixture of 6,7-dimethoxy-5-nitro-3,4-dihydroquinazolin-4-one (1.75 g, 7.0 mmol) and thionyl chloride (25 ml) and DMF (3 drops) was heated at reflux for 2 hours. Excess thionyl chloride was removed by evaporation and the residue azeotroped with toluene. 3-Hydroxy-4-methylaniline (0.94 g, 7.6 mmol) in 2-propanol (40 ml) was added to the residue and the mixture heated at reflux for 2 hours. The mixture was allowed to cool, the precipitate collected by filtration, washed with 2-propanol and dried to give 6,7-dimethoxy-4-(3-hydroxy-4-methylanilino)-5-nitroquinazoline hydrochloride (2.02 g, 81%).

m.p. 206–208° C.; $^1$H NMR Spectrum: (DMSOd$_6$) 3.90(s, 3H); 4.05(s, 1H); 6.50(d,1H); 6.65(s,1H); 6.97(d, 1H); 7.57 (s, 1H); 8.15(s, 1H); MS-ESI: 357 [MH]$^+$; Elemental analysis: Found C, 52.0; H, 4.3; N, 13.9; $C_{17}H_{16}N_4O_5$ 1 HCl Requires C, 52.0; H, 4.3; N, 14.3%.

The starting material was prepared as follows:

A mixture of 4,5-dimethoxyanthranilic acid (19.7 g) and formamide (10 ml) was stirred and heated at 190° C. for 5 hours. The mixture was allowed to cool to approximately 80° C. and water (50 ml) was added. The mixture was stored at ambient temperature for 3 hours. The precipitate was isolated, washed with water and dried to give 6,7-dimethoxy-3,4-dihydroquinazolin-4-one (3.65 g).

Fuming nitric acid (47 ml) was added to 6,7-dimethoxy-3,4-dihydroquinazolin-4-one (10 g, 48 mmol), in water (40 ml). The reaction mixture was heated at 120° C. for 1 hour, then allowed to cool and diluted with water. The resulting precipitate was collected by filtration, washed with water and dried to give 6,7-dimethoxy-5-nitro-3,4-dihydroquinazolin-4-one (3.9 g, 32%).

$^1$H NMR Spectrum: (DMSOd$_6$) 3.87(s, 3H); 4.05(s, 1H); 7.42(s, 1H); 8.13(s, 1H); MS-ESI: 251 [MH]$^+$.

EXAMPLE 8

Sodium (148 mg, 6.4 mmol) was added to 2-methoxyethanol (10 ml), the mixture stirred for 15 minutes to give a complete solution and the volatiles removed by evaporation. The residue was dissolved in DMSO (5 ml) and 7-chloro-4-(4-chloro-2-fluoroanilino)-6-nitroquinazoline hydrochloride (500 mg, 1.3 mmol) was added. The mixture was stirred at ambient temperature for 18 hours then diluted with a solution of acetic acid (1 ml) in water (20 ml). The resulting precipitate was collected by filtration, washed with water, dried and purified by column chromatography eluting with methylene chloride/methanol (96/4). The purified product was recrystallised from methylene chloride/isohexane to give 4-chloro-2-fluoroanilino)-7-(2-methoxyethoxy)-6-nitroquinazoline (304 mg, 60%) as a yellow solid.

$^1$H NMR Spectrum: (DMSOd$_6$) 3.15(s, 3H); 3.60(m, 2H); 4.31(m, 2H); 7.24(m, 1H); 7.4–7.5(m, 3H); 8.42(s, 1H); 9.03(s, 1H); MS-ESI: 393 [MH]$^+$; Elemental analysis: Found C, 51.8; H, 3.7; N, 14.1; $C_{17}H_{14}N_4O_4ClF$ Requires C, 52.0; H, 3.6; N, 14.3%.

The starting material was prepared as follows:

A mixture of 7-chloro-6-nitro-3,4-hydroquinazolin-4-one (40 g, 0.18 mol), (J. Org. Chem. 1975,40, 356), phosphorus oxychloride (50 ml) and DMF (1 ml) in thionyl chloride (300 ml) was heated at reflux for 4 hours. The reaction mixture was allowed to cool and the volatiles removed by evaporation and by azeotroping with toluene. The residue was basified with aqueous sodium hydrogen carbonate solution and extracted with methylene chloride (4×100 ml). The extracts were combined, washed with brine and filtered through phase separating paper. The solvent was removed by evaporation and the residue triturated with ether/isohexane to give 4,7-dichloro-6-nitroquinazoline (35.2 g, 81%) as a pale yellow solid.

A mixture of 4,7-dichloro-6-nitroquinazoline (24.4 g, 0.1 mol), 4-chloro-2-fluoroaniline and ethereal hydrogen chloride (100 ml of a 1M solution) in 2-propanol (600 ml) was heated at reflux for 1.5 hours. The mixture was allowed to cool and diluted with acetone. The solid product was collected by filtration, washed with acetone and dried to give 7-chloro-4-(4-chloro-2-fluoroanilino)-6nitroquinazoline hydrochloride (35.0 g, 90%) as a yellow powder.

MS-ESI: 353 [MH]$^+$.

EXAMPLE 9

Triphenylphosphine (410 mg, 1.5 mmol) and 1-methyl-3-pyrrolidinol (0.128 ml, 1.5 mmol) were added to a solution of 4-(chloro-2-fluoroanilino)-7-hydroxy-6-methoxyquinazoline (250 mg, 0.78 mmol), (prepared as described for the starting material in Example 2), in methylene chloride (4 ml). Diethyl azodicarboxylate (0.246 ml, 1.5 mmol) was added dropwise and the reaction mixture was stirred for 1 hour at ambient temperature. Additional triphenylphosphine (61 mg, 0.23 mmol) followed by diethyl azodicarboxylate (37 µl, 0.23 mmol) was added and the mixture was stirred for 15 minutes at ambient temperature. The solvent was removed by evaporation and the residue was purified by column chromatography eluting with methylene chloride/methanol (80/20) followed by methylene chloride/methanol/triethylamine (80/20/0.5). The purified product was dissolved in methylene chloride/methanol and the insolubles were removed by filtration. A solution of hydrogen chloride in 2-propanol (0.5 ml of a 5M solution) was added to the filtrate and the volatiles were removed by evaporation. The residue was triturated with 2-propanol and ether, collected by filtration and dried to give 4-(4-chloro-2-fluoranilino)-6-methoxy-7-(1-methylpyrrolidin-3-yloxy) quinazoline hydrochloride hydrate (149 mg, 40%).

$^1$H NMR Spectrum: (DMSOd$_6$; CF$_3$COOD) 2.13–2.83 (m, 2H); 2.92(s, 3H); 2.99(s, 3H); 3.20–3.32(m, 1H); 3.44–3.59(m, 1H); 3.72–3.81(m, 1H); 3.96–4.14(m, 2H); 4.01 (s, 3H); 5.35–5.43(m, 1H); 7.42–7.47(m, 2H); 7.58–7.63(m, 2H); 8.21(s, 1H); 8.88(s, 1H); MS-ESI: 403 [MH]$^+$; Elemental analysis: Found C, 48.8; H, 5.2; N, 11.0; $C_{20}H_{20}N_4O_2ClF$ 1 $H_2O$ 2 HCl Requires C, 48.7; H, 4.9; N, 11.4%.

EXAMPLE 10

4-(Chloro-2-fluoroanilino)-7-hydroxy-6-methoxyquinazoline (250 mg, 0.78 mmol), (prepared as described for the starting material in Example 2), and triphenylphosphine (512 mg, 1.9 mmol) were added to a stirred solution of 4-morpholino-2-butyn-1-ol (182 mg, 1.1 mmol), (J. Am. Chem. Soc. 1957, 79, 6184), in methylene chloride (4 ml) under argon. Diethyl azodicarboxylate (0.307 ml, 1.9 mmol) was added dropwise and the reaction mixture was stirred for 30 minutes at ambient temperature. Additional 4-morpholino-2-butyn-1-ol (60 mg, 0.39 mmol), triphenylphosphine (102 mg, 0.39 mmol) and followed by diethyl azodicarboxylate (61 μl, 0.39 mmol) were added and the mixture was stirred for a further 15 minutes at ambient temperature. The solvent was removed by evaporation and the residue was purified by column chromatography eluting with methylene chloride/acetonitrile/methanol (60/37/3 followed by 60/35/5 and 55/37/8). The resulting purified oil was dissolved in a mixture of methylene chloride and methanol and ethereal hydrogen chloride (1 ml of a 2.9M solution) was added. The volatiles were removed by evaporation, the solid residue suspended in ether and collected by filtration. The product was recrystallised from 2-propanol/methanol/ether, collected by filtration, washed with 2-propanol and ether and dried to give 4-(4-chloro-2-fluoroanilino)-6-methoxy-7-(4-morpholinobut-2-yn-1-yloxy)quinazoline hydrochloride hydrate (75 mg, 18%).

m.p. 175–178° C.; $^1$H NMR Spectrum: (DMSOd$_6$; CF$_3$COOD) 3.10(m, 2H); 3.46(m, 2H); 3.72(m, 2H); 3.99 (m, 2H); 4.03(s, 3H); 4.29(s, 2H); 5.28(s, 2H); 7.47(dd, 2H); 7.62(s, 1H); 7.69(dd, 1H); 8.29(s, 1H); 8.89(s, 1H); MS-ESI: 457 [MH]$^+$; Elemental analysis: Found C, 50.8; H, 4.9; N, 10.3; C$_{23}$H$_{22}$N$_4$O$_3$ClF 1 H$_2$O 2 HCl Requires C, 50.4; H, 4.7; N, 10.2%.

EXAMPLE 11

Tetrakis(triphenylphosphine)palladium(0) (23 mg, 0.02 mmol) followed by a solution of sodium triisopropylsilylthiolate (102 mg, 0.48 mmol), (Tetrahedron.Lett. 1994, 35, 3221), in THF (2 ml) was added to a stirred solution of 4-(4-chloro-2-fluoroanilino)-6-methoxy-7-(trifluoromethylsulphonyloxy)quinazoline (180 mg, 0.4 mmol) in THF (2 ml) and benzene (2 ml) under argon. The reaction mixture was heated at reflux for 2 hours and then allowed to cool. 2-Bromoethyl methyl ether (83 mg, 0.6 mmol) in DMF (1 ml) and then a solution of tetrabutylammonium fluoride in THF (0.5 ml of a 1M solution, 0.5 mmol) were added dropwise and the reaction mixture was stirred at ambient temperature for 30 minutes. The mixture was diluted with ethyl acetate, washed with water and brine, dried (MgSO$_4$) and the volatiles removed by evaporation. The residue was purified by column chromatography on neutral alumina eluting with methylene chloride/acetone (95/5). The purified product was triturated with ether, collected by filtration and dissolved in methylene chloride (4 ml). Ethereal hydrogen chloride (0.4 ml of 3M solution) was added, the solution was diluted with ether and the resulting precipitate was collected by filtration and dried to give 4-(4-chloro-2-fluoroanilino)-4-methoxy-7-(2-methoxyethylthio)quinazoline hydrochloride (80 mg, 46%).

$^1$H NMR Spectrum: (DMSOd$_6$; CF$_3$COOD) 3.33(t, 2H); 3.34(s, 3H); 3.71 (t, 2H); 4.07(s, 3H); 7.48(dd, 1H); 7.64(t, 1H); 7.69(dd, 1H); 7.73(s, 1H); 8.10(s, 1H); 8.89(s, 1H). MS-ESI: 394 [MH]$^+$; Elemental analysis: Found C, 50.1; H, 4.3; N, 9.8; S, 7.3; C$_{18}$H$_{17}$N$_3$O$_2$ClFS 1 HCl Requires C, 50.2; H, 4.2; N, 9.8; S, 7.4%.

The starting material was prepared as follows:

Trifluoromethanesulphonic anhydride (0.55 ml, 3.3 mmol) was added to a stirred suspension of 4-(chloro-2-fluoroanilino)-7-hydroxy-6methoxyquinazoline (959 mg, 3 mmol), (prepared as described for the starting material in Example 2), in methylene chloride (2.2 ml) and pyridine (2.2 ml) under argon at 0° C. The reaction mixture was stirred for 1 hour at 0° C., allowed to warm to ambient temperature and stirred for a further 1.5 hours. The volatiles were removed by evaporation, the residue was dissolved in ethyl acetate, washed with dilute hydrochloric acid and brine, dried (MgSO$_4$) and the solvent removed by evaporation. The residue was triturated with ether/petroleum ether to give 4-(4-chloro-2-fluoroanilino)-6-methoxy-7-(trifluoromethylsulphonyloxyquinazoline (270 mg, 60%) as a beige solid.

$^1$H NMR Spectrum: (DMSOd$_6$) 4.07(s, 3H); 7.39(dd, 1H); 7.57–7.62(m, 2H); 7.92(s, 1H); 8.21(s, 1H); 8.49(s, 1H); MS-ESI: 452 [MH]$^+$.

EXAMPLE 12

4-(2-Hydroxyethyl)thiomorpholine (114 mg, 0.78 mmol), (J. Am. Chem. Soc. 1934. 56, 1720), in methylene chloride (1 ml) followed by 1,1'-(azodicarbonyl)dipiperidine (525 mg, 2.08 mmol) were added to a stirred solution of 4-(4-chloro-2-fluoroanilino)-7-hydroxy-6-methoxyquinazoline (225 mg, 0.70 mmol), (prepared as described for the starting material in Example 2), and tributylphosphine (0.51 ml, 2.08 mmol) in methylene chloride (10 ml) under nitrogen. The mixture was stirred for 3.5 hours and allowed to stand for a further 18 hours. Ether (8 ml) was added, the precipitate removed by filtration and the solvent removed from the filtrate by evaporation. The residue was dissolved in acetone and ethereal hydrogen chloride (2.5 ml of a 1 M solution) added. The precipitated product was collected by filtration and purified by column chromatography eluting with methylene chloride/methanol/aqueous ammonia (150/8/1). The purified product was triturated with ether to give 4-(4-chloro- 2-fluoroanilino)-6-methoxy-7-(2-thiomorpholinoethoxy)quinazoline (70 mg, 22%) as a pale yellow solid.

m.p. 181–182° C.; $^1$H NMR Spectrum: (DMSOd$_6$) 3.56(t, 2H); 3.92(s, 3H); 4.59(t, 2H); 7.31(dd, 1H); 7.35(s, 1H); 7.46(d, 1H); 7.53(dd, 1H); 8.33(s, 1H); 8.68(s, 1H); 11.7(br s, 1H); MS-ESI: 449 [MH]$^+$; Elemental analysis: Found C, 56.4; H, 5.1; N, 12.3; C$_{21}$H$_{22}$N$_4$O$_2$ClFS Requires C, 56.2; H, 4.9; N, 12.5%.

EXAMPLE 13

A solution of (R)-(1-methylpiperidin-3-yl)methanol (2.29 g, 18 mmol) in methylene chloride (10 ml) was added to a stirred mixture of 4-(chloro-2-fluoroanilino)-7-hydroxy-6-methoxyquinazoline (4.0 g, 12.5 mmol), (prepared as described for the starting material in Example 2), and triphenylphosphine (9.81 g, 37.5 mmol) in methylene chloride (200 ml). Diethyl azodicarboxylate (5.87 ml, 37 mmol) was added dropwise and the reaction mixture was stirred for 18 hours at ambient temperature. The volatiles were removed by evaporation and the residue was purified by column chromatography eluting with methylene chloride/ methanol/aqueous ammonia (a gradient from 100/0/0 to 85/15/0.1). The purified product was triturated with ethyl acetate, collected by filtration, washed with ethyl acetate and dried to give (R)-4-(4-chloro-2-fluoroanilino)-6-methoxy-7-(1-methylpiperidin-3-yl)methoxyquinazoline (2.78 g, 52%).

[α]$_D$ +11.7°; $^1$H NMR Spectrum: (DMSOd$_6$) 1.08(m, 1H); 1.50(m, 1H); 1.64(m, 1H); 1.80(m, 3H); 2.07(m, 1H); 2.16(s, 3H); 2.62(d, 1H); 2.81(d, 1H); 3.92(s, 3H); 4.02(d, 2H); 7.18(s, 1H); 7.32(d, 1H); 7.55(m, 2H); 7.79(s, 1H);

8.34(s, 1H); 9.50(s, 1H); MS-ESI: 431 [MH]⁻; Elemental analysis: Found C, 60.7; H, 5.4; N, 13.3; $C_{22}H_{24}N_4O_2ClF$ Requires C, 61.3; H, 5.6; N, 13.0%.

The starting material was prepared as follows:

(R)-Ethyl nipecotate (5.7 g 365 mmol), (prepared by resolution of ethyl nipecotate by treatment with L(+)-tartaric acid as described in J. Org. Chem. 1991, (56), 1168), was dissolved in 38.5% aqueous formaldehyde solution (45 ml) and formic acid (90 ml) and the mixture heated at reflux for 18 hours. The mixture was allowed to cool and added dropwise to cooled saturated aqueous sodium hydrogen carbonate solution. The mixture was adjusted to pH12 by addition of sodium hydroxide and the mixture was extracted with methylene chloride. The organic extract was washed with brine, dried ($MgSO_4$) and the solvent removed by evaporation to give (R)-ethyl 1-methylpiperidine-3-carboxylate (4.51 g, 73%) as a colourless oil.

MS-ESI: 172 [MH]⁺.

A solution of (R)-ethyl 1-methylpiperidine-3-carboxylate (5.69 g, 33 mmol) in ether (20 ml) was added dropwise to a stirred solution of lithium aluminum hydride (36.6 ml of a 1M solution in THF, 36.6 mmol) in ether (85 ml) cooled to maintain a reaction temperature of 20° C. The mixture was stirred for 1.5 hours at ambient temperature and then water (1.4 ml), 15% aqueous sodium hydroxide solution (1.4 ml) and then water (4.3 ml) were added. The insolubles were removed by filtration and the volatiles removed from the filtrate by evaporation to give (R)-(1-methylpiperidin-3-yl)methanol (4.02 g, 94%) as a colourless oil.

¹H NMR Spectrum: (DMSOd₆) 1.06(q, 1H); 1.51–1.94 (m, 5H); 2.04(s, 3H); 2.34(br s. 1H); 2.62(m, 1H); 2.78(d, 1H); 3.49(m, 1H); 3.59(m. 1H); MS-ESI: 130 [MH]⁺.

EXAMPLE 14

Using a method analogous to that in Example 13, (S)-(1-methylpiperidin-3-yl)methanol (185 g, 1.1 mmol), (prepared as described for the starting material in Example 13 but resolving with D(−)-tartaric acid), was treated with 4-(chloro-2-fluoroanilino)-7-hydroxy-6-methoxyquinazoline (319 mg, 1 mmol), (prepared as described for the starting material in Example 2), triphenylphosphine (785 mg, 3 mmol) and diethyl azodicarboxylate (0.475 ml, 3 mmol) to give, after work-up and purification, (S)-4-(4-chloro-2-fluoroanilino)-6-methoxy-7-(1-methylpiperidin-3-yl)methoxyquinazoline (187 mg, 44%).

EXAMPLE 15

The final compounds in Examples 13 and 14 may be mixed, in any relative proportions, for example to give a racemic mixture.

Alternatively the racemate may be made as follows:

1,1'-(Azodicarbonyl)dipiperidine (560 mg, 2.2 mmol) was added in portions to a mixture of 4-(4-chloro-2-fluoroanilino)-7-hydroxy-6-methoxyquinazoline (240 mg, 0.75 mmol), (prepared as described for the starting material in Example 2), 1-methyl-3-piperidinemethanol (115 mg, 0.89 mmol) and tributylphosphine (440 mg, 2.2 mmol) in methylene chloride (10 ml). The mixture was stirred for 18 hours, diluted with ether and the resulting precipitate was removed by filtration. The volatiles were removed from the filtrate by evaporation, and the residue was dissolved in acetone and ethereal hydrogen chloride (1.5 ml of a 1M solution, 1.5 mmol) was added. The precipitated product was collected by filtration and purified by column chromatography eluting with methylene chloride/methanol/aqueous ammonia (75/8/1). The purified solid product was triturated with ether collected by filtration and dried to give 4-(4chloro-2-fluoroanilino)-6-methoxy-7-(1-methylpiperidin-3-ylmethoxy)quinazoline (105 mg, 33%).

m.p. 211–212° C.; ¹H NMR Spectrum: (DMSOd₆) 1.08 (m, 1H); 1.50(m, 1H); 1.78(m, 4H); 2.08(m, 1H); 2.16(m, 3H); 2.62(m, 1H); 2.82(m, 1H); 3.95(s, 3H); 4.00(d, 2H); 7.18(s, 1H); 7.32(m, 1H); 7.52(dd, 1H); 7.58(t, 1H); 7.79(s, 1H); 8.35(s, 1H); 9.52(s, 1H); MS-ESI: 431 [MH]⁺; Elemental analysis: Found C, 59.9; H, 5.5; N, 12.9; $C_{22}H_{24}N_4O_2ClF$ $0.5H_2O$ Requires C, 60.0; H, 5.7; N, 12.7%.

EXAMPLE 16

3-(Methylsulphonyl)propan-1-ol (0.6 g, 4.3 mmol) followed by 1,1'-(azodicarbonyl)dipiperidine (4.2 g, 16 mmol) in portions were added to a stirred solution of 4-(4-chloro-2-fluoroanilino)-7-hydroxy-6-methoxyquinazoline (1.5 g, 4.7 mmol), (prepared as described for the starting material in Example 2), and tributylphosphine (4.0 ml, 16 mmol) in methylene chloride (50 ml) under nitrogen. The mixture was stirred for 18 hours, the resulting precipitate was collected by filtration and dried to give crude product (1.36g). The solvent was removed from the filtrate by evaporation and the residue was purified by column chromatography eluting with methylene chloride/methanol (a gradient from 100/0 to 90/10). The semi-purified product was triturated with acetone and the solid product collected by filtration and dried to give further crude product (0.53 g). The filtrate from the trituration was repurified by column chromatography as before to give freer crude product (0.23 g). The crude products were combined and dissolved in acetone/methanol/methylene chloride and ethereal hydrogen chloride (6 ml of a 1M solution) added. The precipitated product was collected by filtration and recrystalilsed from methanol/methylene chloride/hexane to give 4-(4-chloro-2-fluoroanilino)-6-methoxy-7-(3(methylsulphonyl)propoxy) quinazoline hydrochloride (640 mg, 29%).

m.p.>250° C.; ¹H NMR Spectrum: (DMSOd₆) 2.25(q, 2H); 3.02(s, 3H); 3.36(t, 2H); 4.00(s, 3H); 4.30(t, 2H); 7.35(s, 1H); 7.42(d, 1H); 7.60(t, 1H); 7.65(d, 1H); 8.25(s, 1H); 8.78(s, 1H); 11.5(br s, 1H); MS-ESI: 440 [MH]⁺; Elemental analysis: Found C, 47.8; H, 4.2; N, 8.8; S, 6.7; $C_{19}H_{19}N_3O_4ClFS$ 1HCl Requires C, 47.4; H, 4.2; N, 9.0; S, 6.8%.

The starting material was prepared as follows:

A solution of 3-(methylthio)propan-1-ol (5.3 g, 50 mmol) in methanol (500 ml) was added to a solution of OXONE, (trade mark of E.I. du Pont de Nemours & Co., Inc), (30 g) in water (150 ml) and the mixture stirred at ambient temperature for 24 hours. The precipitated solid was removed by filtration and the methanol removed from the filtrate by evaporation. The aqueous residue was saturated with sodium chloride and extracted with methylene chloride (4×25 ml). The aqueous residue was then saturated with ammonium chloride and extracted with ethyl acetate (4×25 ml). The extracts were combined, dried ($MgSO_4$) and the solvent removed by evaporation to give 3-(methylsulphonyl) propan-1-ol (610 mg, 9%) as an oil.

¹H NMR Spectrum: (CDCl₃) 2.10(m, 2H); 2.96(s, 3H); 3.20(t, 2H); 3.80(t, 2H); MS-ESI: 139 [MH]⁺.

EXAMPLE 17

Diethyl azodicarboxylate (5.91 ml, 37 mmol) was added dropwise to a stirred mixture of (E)-4-pyrrolidin-1-yl)but-2-en-1-ol (3.97 g, 28 mmol), 4-(chloro-2-fluoroanilino)-7- hydroxy-6-methoxyquinazoline (3.0 g, 9 mmol), (prepared as described for the starting material in Example 2), and triphenylphosphine (9.84 g, 38 mmol) in methylene chloride (300 ml). The reaction mixture was stirred for 18 hours at ambient temperature. The volatiles were removed by evaporation and the residue was purified by column chromatography eluting with methylene chloride/methanol (a gradient from 80/20 to 70/30). The purified product was dissolved in methylene chloride/methanol and 1M ethereal hydrogen chloride (25 ml) was added. The precipitated product was collected by filtration, washed with ether and dried to give (E)-4-(4-chloro-2-fluoroanilino)-6-methoxy-7-(4-(pyrrolidin-1-yl)but-2-en-1-yloxy)quinazoline hydrochloride (1.62 g, 33%).

$^1$H NMR Spectrum: (DMSOd$_6$; CF$_3$COOD) 1.85–1.95 (m, 2H); 2.0–2.15(m, 2H); 3.0–3.1(m, 2H); 3.5–3.6(m, 2H); 3.95(d, 2H); 4.1(s, 3H); 4.95(d, 2H); 6.1(td, 1H); 6.35(td, 1H); 7.4(s, 1H); 7.45(dd, 1H); 7.6–7.7(m, 2H); 8.15(s, 1H); 8.90(s, 1H); MS-EI: 443 [MH]$^+$; Elemental analysis: Found C, 52.7; H, 5.3; N, 10.8; C$_{21}$H$_{24}$N$_4$O$_2$ClF 0.6H$_2$O 1.85HCl Requires C, 53.0; H, 5.2; N, 10.7%.

The starting material was prepared as follows:

Thionyl chloride (9.3 ml, 128 mmol) was added dropwise to a stirred solution of 2-butyne-1,4-diol (10 g, 116 mmol) in toluene (15 ml) and pyridine (10.3 ml) cooled at 0° C. The mixture was stirred for 3.5 hours at ambient temperature and then poured onto ice water. The mixture was extracted with ether, the organic layer was washed with saturated aqueous sodium hydrogen carbonate solution and then brine, dried (MgSO$_4$) and the volatiles removed by evaporation. The residue was purified by column chromatography eluting with petroleum ether/ether (7/3) to give 4-chlorobut-2-yn-1-ol (4.74 g, 39%).

$^1$H NMR Spectrum: (CDCl$_3$) 1.68(t, 1H); 4.18(d, 2H); 4.33(d, 2H).

Pyrrolidine (7.8 ml, 94 mmol) was added dropwise to a solution of 4-chlorobut-2-yn-1-ol (4.74 g, 45 mmol) in toluene (40 ml) and the mixture stirred and heated at 60° C. for 1 hour. The volatiles were removed by evaporation and the residue was purified by chromatography eluting with methylene chloride/methanol (96/4) to give 4-(pyrrolidin-1-yl)but-2-yn-1-ol (4.3 g, 69%).

$^1$H NMR Spectrum: (CDCl$_3$) 1.82(t, 4H); 2.63(t, 4H); 3.44(t, 2H), 4.29(t, 2H).

A solution of 4-(pyrrolidin-1-yl)but-2-yn-1-ol (4.3 g, 31 mmol) in THF (20 ml) was added dropwise to a suspension of lithium aluminum hydride (2.35 g, 62 mmol) in anhydrous THF (8 ml) and the mixture stirred and heated at 60° C. for 2 hours. The mixture was cooled to 5° C. and 2M aqueous sodium hydroxide solution (28 ml) was added dropwise. The resulting suspension was filtered and the volatiles removed from the filtrate by evaporation. The residue was dissolved in a mixture of methylene chloride/ethyl acetate, dried (MgSO$_4$) and the solvent removed by evaporation. The residue was purified by column chromatography on aluminum oxide eluting with methylene chloride/methanol (97/3) to give (E)-4-(pyrrolidin-1-yl)but-2-en-1-ol (3.09 g, 70%).

$^1$H NMR Spectrum: (CDCl$_3$) 1.82(m, 4H); 2.61 (m, 4H); 3.17(m, 2H); 4.13(s, 2H); 5.84(m, 2H).

EXAMPLE 18

A solution of 4-(4-bromo-2-fluoroanilino)-7-(3-chloropropoxy)-6-methoxyquinazoline (150 mg, 0.34 mmol) in 1-(2-hydroxyethyl)piperazine (5 ml) was heated at 100° C. for 30 minutes. The reaction mixture was allowed to cool and made basic with aqueous sodium hydrogen carbonate solution and extracted with ethyl acetate (3×50 ml). The extracts were combined, washed twice with water, then brine and dried (MgSO$_4$). The volatiles were removed by evaporation and the residue dissolved in acetone/methanol (10/1) (50 ml) and ethereal hydrogen chloride added. The resulting precipitate was collected by filtration, washed with ether and hexane and dried under vacuum to give 4-(bromo-2-fluoroanilino)-7-(3-[4-(2-hydroxyethyl)piperazinyl]propoxy)-6-methoxyquinazoline hydrochloride (180 mg, 80%).

$^1$H NMR Spectrum: (DMSOd$_6$) 2.35(br t, 2H); 3.2–3.8(br m, 12H); 3.80(t, 2H); 4.02(s, 3H); 4.35(t, 2H); 7.45(s, 1H); 7.30(s, 1H); 7.50–7.58(m, 2H); 7.76(dd, 1H); 8.42(s, 1H); 8.80(s, 1H); 11.82(brs, 1H); MS-ESI: 534 [MH]$^+$.

The starting material was prepared as follows:

A mixture of 4-(4-bromo-2-fluoroanilino)-7-hydroxy-6-methoxyquinazoline (1.2 g, 3.3 mmol), (prepared as described for the starting material in Example 48), 1-bromo-3-chloropropane (1.6 ml, 16 mmol) and potassium carbonate (2.1 g, 15 mmol) in DMF (25 ml) was heated at 45° C. for 3 hours. The mixture was allowed to cool, was diluted with water and extracted with ethyl acetate (3×70 ml). The organic extracts were combined, washed with water and brine, dried (MgSO$_4$) and the volatiles were removed by evaporation. The residue was triturated with hexantlethyl acetate, collected by filtration and dried under vacuum to give 4-(4-bromo-2-fluoroanihno)-7-(3-chloropropoxy)-6-methoxyquinazoline (492 mg, 34%).

$^1$H NMR Spectrum: (DMSOd$_6$) 2.24(m, 2H); 3.80(t, 2H); 3.95(s, 3H); 4.26(t, 2H); 7.20(s, 1H); 7.42–7.55(m, 2H); 7.63(dd, 1H); 7.80(s, 1H); 8.35(s, 1H); 9.52(s, 1H); MS-ESI: 440 [MH]$^+$.

EXAMPLE 19

A solution of OXONE, (trade mark of E.I. du Pont de Nemours & Co., Inc), (390 mg) in water (2 ml) was added to a solution of 4-(chloro-2-fluoroanilino)-7-(3-(ethylthio)propoxy)-6-methoxyquinazoline (75 mg, 0.18 mmol) in methanol (10 ml) and the mixture stirred for 18 hours at ambient temperature. The reaction mixture was basified with aqueous sodium hydrogen carbonate solution and extracted with ethyl acetate (3×25 ml). The extracts were combined, washed twice with water and then with brine, dried (MgSO$_4$) and the solvent removed by evaporation. The solid residue was recrystallised from ethyl acetate/hexane to give 4-(chloro-2-fluoroanilino)-7-(3-(ethylsulphonyl)propoxy)-6-methoxyquinazoline (35 mg, 43%).

$^1$H NMR Spectrum: (DMSOd$_6$) 1.24 (t, 3H); 2.22(m, 2H); 3.15(q, 2H); 3.95(s, 3H); 4.25(t, 2H); 7.20(s, 1H); 7.35(dd, 1H); 7.5–7.6(m, 2H); 7.80(s, 1H); 8.35(s, 1H); 9.54(s, 1H); MS-ESI: 454 [MH]$^+$; Elemental analysis: Found C, 51.7; H, 4.6; N, 9.2; C$_{20}$H$_{21}$N$_3$O$_4$ClFS 0.5H$_2$O Requires C, 51.9; H, 4.8; N, 9.1%.

The starting material was prepared as follows:

A mixture of 4-(4-chloro-2-fluoroanilino)-7-hydroxy-6-methoxyquinazoline (957 mg, 3 mmol), (prepared as described for the starting material in Example 2), 1-bromo-3-chloropropane (2.36 g, 15 mmol) and potassium carbonate (2.1 g, 15 mmol) in DMF (20 ml) was heated at 40° C. for 1.5 hours. The mixture was allowed to cool, was diluted with water and extracted with ethyl acetate (3×50 ml). The organic extracts were combined, washed with water and brine, dried (MgSO$_4$) and the volatiles were removed by evaporation. The residue was triturated with hexanelethyl acetate, collected by filtration and dried under vacuum to give 4-(4-chloro-2-fluoroaniiino)-7-(3-chloropropoxy)-6-methoxyquinazoline (650 mg, 55%).

$^1$H NMR Spectrum: (DMSOd$_6$) 2.26(m, 2H); 3.82(t, 2H); 3.95(s, 3H); 4.26(t, 2H); 7.20(s, 1H); 7.32(dd, 1H); 7.48–7.60(m, 2H); 7.80(s, 1H); 8.35(s, 1H); 9.52(s, 1H); MS-EI: 396 [MH]$^+$.

A mixture of sodium efhanethiolate (120 mg, 1.5 mmol) and 4-(4-chloro-2-fluoroanilino)-7-(3-chloropropoxy)-6-methoxyquinazline (227 mg, 0.57 mmol) in DMF (10 ml) was stirred and heated at 70° C. for 3 hours. The reaction mixture was allowed to cool, was diluted with water and extracted with ethyl acetate (3×75 ml). The extracts were combined, washed with water (×2), and then brine, and dried (MgSO$_4$). The solvent was removed by evaporation and the residue was recrystallised from ethyl acetate/hexane to give 4-(chloro-2-fluoroanilino)-7-(3-(ethylthio)propoxy)-6-methoxyquinazoline (86 mg, 400%).

$^1$H NMR Spectrum: (DMSOd$_6$) 1.20(t, 3H); 2.03(m, 2H); 2.66(t, 2H); 3.95(s, 3H); 4.20(t, 2H); 7.18(s, 1H); 7.33(dd, 1H); 7.5–7.6(m, 2H); 7.78(s, 1H); 8.35(s, 1H); 9.52(s, 1H); MS-ESI: 422 [MH]$^+$.

EXAMPLE 20

A mixture of 4-(chloro-2-fluoroanilino)-7-hydroxy-6-methoxyquinazoline (3.28 g, 10 mmol), (prepared as described for the starting material in Example 2), 1-bromo-3-tetrahydropyranyloxypropane (2.5 g, 11 mmol) and potassium carbonate (5.0 g, 36 mmol) in DMF (50 ml) was stirred and heated at 90° C. for 3 hours. The reaction mixture was allowed to cool, was diluted with water (500 ml) and extracted with ethyl acetate (3×100 ml). The extracts were combined, washed with water (×3), and then brine, and dried (MgSO$_4$). The solvent was removed by evaporation and the residue was purified by column chromatography eluting with ethyl acetate. The purified product was recrystallized from ethyl acetatehexane to give 4-(chloro-2-fluoroanilino)-6-methoxy-7-tetrshydropyran-2-yloxypropoxy)quinazoline (2.25 g, 49%).

m.p. 18–185° C.; $^1$H NMR Spectrum: (DMSOd$_6$) 1.35–1.54(m, 4H); 1.55–1.75(m, 2H); 2.05(m, 2H); 3.35–3.45(m, 1H); 3.66–3.84(m, 2H); 3.95(s, 3H); 4.23(t, 2H); 4.60(s, 1H); 7.18(s, 1H); 7.32(dd, 1H); 7.5–7.6(m, 2H); 7.78(s, 1H); 8.35(s, 1H); 9.53(s, 1H); MS-ESI: 462 [MH]$^+$; Elemental analysis: Found C, 59.6; H, 5.3; N, 9.1; C$_{23}$H$_{25}$N$_3$O$_4$ClF Requires C, 59.9; H, 5,4; N, 9.4%.

EXAMPLE 21

A mixture of sodium methanethiolate (70 mg, 1 mmol) and 4(4-chloro-2-fluoroanilino)-7-(3-chloropropoxy)-6-methoxyquinazoline (200 mg, 0.5 mmol), (prepared as described for the starting material in Example 19), in DMF (10 ml) was stirred and heated at 70° C. for 1 hour. The reaction mixture was allowed to cool, was diluted with water and extracted with ethiyl acetate (3×25 ml). The extracts were combined, washed with water (×2), and then brine, and dried (MgSO$_4$). The solvent was removed by evaporation and the residue was recrystallised from ethyl acetate/hexane to give 4-(chloro-2-fluoroanilino)-6-methoxy-7-(3-methylthiopropoxy)quinazoline (143 mg, 35%).

m.p. 169–170° C. $^1$H NMR Spectrum: (DMSOd$_6$) 2.0–2.12(m, 2H); 2.08(s, 3H); 2.64(t, 2H);.3.93(s, 3H); 4.21(t, 2H); 7.18(s, 1H); 7.33(d, 1H); 7.50–7.61(m, 2H); 7.78(s, 1H); 8.34(s, 1H); 9.53(s, 1H); MS-ESI: 408 [MH]$^+$.

EXAMPLE 22

A mixture of 4-(bromo-2-fluoroanilino)-7-hydroxy-6-methoxyquinazoline (250 mg, 0.7 mmol), (prepared as described for the starting material in Example 48), 2-chloroethyl methyl sulphide (0.1 ml, 1 mmol) and potassium carbonate (1.0 g, 7 mmol) in DMF (10 ml) was stirred and heated at 50° C. for 4 hours. The reaction mixture was allowed to cool, was diluted with water and extracted with ethyl acetate (3×25 ml). The extracts were combined, washed with water (×2), and then brine, and dried (MgSO$_4$). The solvent was removed by evaporation and the residue was purified by column chromatography eluting with ethyl acetate. The purified product was recrystallised from ethyl acetate/hexane to give 4-(4-bromo-2-fluoroanilino)-6-methoy-7-(2-methylthioethoxy)quinazoline (100 mg, 34%).

$^1$H NMR Spectrum: (DMSOd$_6$) 2.20(s, 3H); 2.90(t, 2H); 3.92(s, 3H); 4.30(t, 2H); 7.20(s,1H); 7.42–7.54(m, 2H); 7.62(dd, 1H); 7.80(s, 1H); 8.36(s, 1H); 9.54(s, 1H); MS-ESI: 438 [MH]$^+$; Elemental analysis: Found C, 48.8; H, 3.9; N, 9.8; S, 7.3; C$_{18}$H$_{17}$N$_3$O$_2$BrFS Requires C, 49.3; H, 3.9; N, 9.6; S, 7.3%.

EXAMPLE 23

A solution of 7-(2-bromoethoxy)-4-(4-chloro-2-fluoroanilino)-6-methoxyquinazoline (130 mg, 0.36mmnol), (prepared as described for the starting material in Example 62), in 1-ethoxycarbonylpipeiazine (1.5 ml) was stirred and heated at 100° C. for 2 hours. The mixture was allowed to cool, diluted with water and extracted with ethyl acetate (3×25 ml). The extracts were combined, washed with water (×2) and then brine, and dried (MgSO$_4$). The solvent was removed by evaporation and the residue was dissolved in acetone and 1M ethereal hydrogen chloride (2 ml) was added. The resulting precipitate was collected by filtration and then purified by column chromatography eluting with methylene chloride/methanol/aqueous ammonia (94/5/1). The purified product was dissolved in acetone and 1M ethereal hydrogen chloride (2 ml) was added. The resulting precipitate was collected by filtration, washed with ether and dried to give 4-(4-chloro-2-fluoroanilino)-7-(2-(4-ethoxycarbonylpiperazin-1-yl)ethoxy)-6-methoxyquinazoline hydrochloride (85 mg. 46%).

$^1$H NMR Spectrum: (DMSOd$_6$) 1.20(t, 3H); 3.1–3.6(m, 8H); 3.66(br s, 2H); 4.00(s, 3H); 4.08(q, 2H); 4.65(br s, 2H); 7.40(m, 2H); 7.90(t, 1H); 7.65(dd, 1H); 8.40(s, 1H); 8.80(s, 1H); 11.66(brs, 1H); MS-ESI: 504 [MH]$^+$; Elemental analysis: Found C, 48.6; H, 5.0; N, 12.2; C$_{24}$H$_{27}$N$_5$O$_4$ClF 1H$_2$O 2HCl Requires C, 48.5; H, 5.2; N, 11.8%.

EXAMPLE 24

A mixture of 4-(bromo-2-fluoroanilino)-7-hydroxy-6-methoxyquinazoline (306 mg, 0.84 mmol), (prepared as described for the starting material in Example 48). 2-chloroethyl ethyl sulphide (0.15 ml, 1.3 mmol) and potassium carbonate (0.5 g, 3.6 mmol) in DMF (10 ml) was stirred and heated at 50° C. for 1 hour. The reaction mixture was allowed to cool, was diluted with water and extracted with ethyl acetate (3×25 ml). The extracts were combined, washed with water (×2), and then brine, and dried (MgSO$_4$). The solvent was removed by evaporation and the residue was purified by column chromatography eluting with ethyl acetate. The purified product was recrystallised from ethyl acetate/hexane to give 4-(4-bromo-2-fluoroanilino)-7-(2-ethylthioethoxy)-6-methoxyquinazoline (221 mg, 58%).

$^1$H NMR Spectrum: (DMSOd$_6$) 1.24(t, 3H); 2.66(q, 2H); 2.94(t, 2H); 3.95(s, 3H); 4.30(t, 2H); 7.20(s, 1H); 7.45(t, 1H); 7.52(d, 1H); 7.65(dd, 1H); 7.80(s, 1H); 9.55(s, 1H); MS-ESI: 452 [MH]$^+$.

EXAMPLE 25

A solution of OXONE, (trade mark of E.I. duPont de Nemours & Co., Inc), (150 mg) in water (2 ml) was added to a solution of 4-(4-bromo-2-fluoroanilino)-7-(2-ethylthioethoxy)-6-methoxyquinazoline (125 mg, 0.28 mmol), (prepared as described in Example 24), in methanol (10 ml). The reaction mixture was stirred for 16 hours at ambient temperature, the methanol was removed by evaporation, the aqueous residue was basified with sodium hydrogen carbonate solution and then extracted with ethyl acetate (3×30 ml). The extracts were combined, washed with water (×2), and then brine, and dried (MgSO$_4$). The solvent was removed by evaporation and the residue was purified by column chromatography eluting with ethyl acetate and then with methylene chloridetmethanol (9/1) to give 4-(4-bromo-2-fluoroanilino)-7-(2-ethylsulphinylethoxy)-6-methoxyquinazoline (32 mg, 31%).

$^1$H NMR Spectrum: (DMSOd$_6$) 1.21(t, 3H); 2.72–2.84(m, 1H); 2.86–2.96(m, 1H); 3.04–3.12(m, 1H); 3.94(s, 3H); 4.42–4.58(m, 2H); 7.26(s, 1H); 7.42–7.55(m, 2H); 7.64(dd, 1H); 7.82(s, 1H); 8.35(s, 1H); 9.55(s, 1H); MS-ESI: 468 [MH]$^+$.

EXAMPLE 26

Using a method analogous to that in Example 25, 4-(4-chloro-2-fluoroanilino)-6-methoxy-7-(3-methylthiopropoxy)quinazoline (250 mg, 0.6 mmol), (prepared as described in Example 21), was treated with OXONE, (trade mark of E.I. du Pont de Nemours & Co., Inc), (84 mg) and the product was pied and isolated to give 4-(4-chloro-2-fluoroanilino)-6-methoxy-7-(3-methylsulphinylpropoxy)quinazoline (75 mg, 29%).

$^1$H NMR Spectum: (DMSOd$_6$) 2.18(t, 2H); 2.60(s, 3H); 2.78–2.98(m, 2H); 3.95(s, 3H); 4.25(t, 2H); 7.20(s, 1H); 7.35(dd, 1H); 7.50–7.61(m, 2H); 7.80(s, 1H); 8.53(s, 1H); 9.55(s, 1H); MS-ESI: 424 [MH]$^+$; Elemental analysis: Found C, 53.4; H, 4.5; N, 9.8; C$_{19}$H$_{19}$N$_3$O$_4$ClFS Requires C, 53.9; H, 4.5; N, 9.8%.

EXAMPLE 27

A solution of OXONE, (trade mark of E.I. du Pont de Nemours & Co., Inc), (800 mg) in water (3 ml) was added to a solution of 4-(4-bromo-2-fluoroanilino)-7-(2-ethylthioethoxy)-6-methoxyquinazoline (320 mg, 0.7mmol), (prepared as described in Example 24), in methanol (10 ml). The reaction mixture was stirred for 20 hours at ambient temperature, the methanol was removed by evaporation, the aqueous residue was basified with sodium hydrogen carbonate solution, saturated with sodium chloride and then extracted with ethyl acetate (3×5oml). The extracts were combined, dried (MgSO$_4$) and the solvent was removed by evaporation. The residue was dissolved in acetone/methanol and 1M ethereal hydrogen chloride (2 ml) was added. The volatiles were removed by evaporation, the residue was triturated with 2-propanol/hexane, collected by filtration and dried to give 4-(4-bromo-2-fluoroanilino)-7-(2-ethylsulphonylethoxy)-6-methoxyquinazoline hydrochloride (200 mg, 55%).

$^1$H NMR Spectrum: (DMSOd$_6$) 1.28(t, 3H); 3.25(q, 2H); 3.74(t, 2H); 4.00(s, 3H); 4.54(t, 2H); 7.43(s, 1H); 7.54(m, 1H); 7.56(s, 1H); 7.75(d, 1H); 8.36(s, 1H); 8.78(s, 1H); 11.61(br s, 1H); MS-ESI: 484 [MH]$^+$.

EXAMPLE 28

A solution of OXONE, (trade mark of E.I. du Pont de Nemours & Co., Inc), (800 mg) in water (3 ml) was added to a solution of 4-(4chloro-2-fluoroanilino)-7-(2-ethylthioethoxy)-6-methoxyquinazoline (220 mg, 0.56 mmol) in methanol (10 ml). The reaction mixture was stirred for 20 hours at ambient temperature, the methanol was removed by evaporation, the aqueous residue was basified with sodium hydrogen carbonate solution, saturated with sodium chloride and then extracted with ethyl acetate (3×50 ml). The extracts were combined, dried (MgSO$_4$) and the solvent was removed by evaporation. The residue was dissolved in acetone/methanol and 1M ethereal hydrogen chloride (1.2 ml) was added. The volatiles were removed by evaporation, the residue was triturated with 2-propanol, collected by filtration and dried to give 4-(4-chloro-2-fluoroanilino)-7-(2-ethylsulphonylethoxy)-6-methoxyquinazoline hydrochloride (24 mg, 90%).

$^1$H NMR Spectrun: (DMSOd$_6$) 1.25(t, 3H); 3.30(q, 2H); 3.75(t, 2H); 4.00(s, 3H); 4.55(t, 2H); 7.36(s, 1H); 7.41(dd, 1H); 7.58(t, 1H); 7.64(dd, 1H); 8.22(s, 1H); 8.78(s, 1H); MS-ESI: 440 [MH]$^+$.

The starting material was prepared as follows:

A mixture of 4-(chloro-2-fluoroanilino)-7-hydroxy-6-methoxyquinazoline (450 mg, 1.4 mmol), (prepared as described for the starting material in Example 2), 2-chloroethyl ethyl sulphide (0.2 ml, 1.7 mmol) and potassium carbonate (1.5 g, 11 mmol) in DMF (10 ml) was stirred and heated at 50° C. for 2 hours. The reaction mixture was allowed to cool, was diluted with water and extracted with ethyl acetate (3×50 ml). The extracts were combined, washed with 0.1M sodium hydroxide solution (×2), water and then brine, and dried (MgSO$_4$). The solvent was removed by evaporation to give crude 4-(4-chloro-2-fluoroanilino)-7-(2-ethylthioethoxy)-6-methoxyquinazoline (230 mg, 57%) which was used directly.

EXAMPLE 29

A mixture of 4-(chloro-2-fluoroanilino)-7-hydroxy-6-methoxyquiazoline (400 mg, 1.3 mmol), (prepared as described for the starting material in Example 2), 2-chloroethyl methyl sulphide (0.168 ml, 1.7 mmol) and potassium carbonate (347 mg, 2.5 mmol) in NMP (10 ml) was stirred and heated at 90° C. for 1 hour, then allowed to cool and stirred for 16 hours at ambient temperature. The reaction mixture was diluted with water and extracted with ethyl acetate. The extracts were combined, washed with water, and then brine, and dried (MgSO$_4$). The solvent was removed by evaporation, the residue was triturated with ethyl acetate/hexane and collected by filtration to give 4-(4-chloro-2-fluoroanilino)-6-methoxy-7-(2-methylthioethoxy)quinazoline (220 mg, 440/%).

m.p. 174–176° C.; $^1$H NMR Spectrum: (DMSOd$_6$) 2.20(s, 3H); 2.92(t, 2H); 3.94(s, 3H); 4.32(t, 2H); 7.20(s, 1H); 7.32(d, 1H); 7.49–7.6(m, 2H); 7.80(s, 1H); 8.36(s, 1H); 9.55(s, 1H); MS-ESI: 452 [MH]$^+$.

EXAMPLE 30

A solution of OXONE, (trade mark of E.I. du Pont de Nemours & Co., Inc), (652 mg) in water (1.6 ml) was added to a solution of 4-(4-chloro-2-fluoroanilino)-6-methoxy-7-(2-methylthioethoxy)quinaaoline (200 mg, 0.5 mmol), (prepared as described in Example 29), in metanol (10 ml) and the mixture was stredfor 18 hours at ambient temperature. The mixture was diluted with methylene chloride, was washed with aqueous sodium hydrogen carbonate solution, dried (MgSO$_4$) and the solvent was removed by evaporation. The residue was triturated with ethyl acetate/hexane, collected by filtration and dried to give 4-(4-chloro-2-fluoroanilino)-6-methoxy-7-(2-methylsulphonylethoxy) quinazoline (172 mg, 80%).

m.p. 227–230° C. $^1$H NMR Spectrum: (DMSOd$_6$) 3.18(s, 3H); 3.70(t, 2H); 3.92(s, 3H); 4.50(t, 2H); 7.22–7.38(m, 2H); 7.42(s, 1H); 7.48–7.60(m, 2H); 8.37(s, 1H); 9.55(s, 1H); MS-ESI: 426 [MH]$^+$; Elemental analysis: Found C, 46.0; H, 3.6; N, 8.7; C$_{18}$H$_{17}$N$_3$O$_4$ClFS 2.2H$_2$O Requires C, 46.4; H, 4.1; N, 9.0%.

EXAMPLE 31

1,1'-(Azodicarbony)dipiperidine (1.56 g, 6.2 mmol) followed by 3-(methylthio)-1-propanol (0.32 ml, 3 mmol) was added to a mixture of 4-(4-bromo-2-fluoroanilino)-7-hydroxy-6-methoxyquinazoline (225 mg, 7.0 mmol), (prepared as described for the starting material in Example 48), and tributylphosphine (1.42 mL 6.1 mmol) in methylene chloride (20 ml) at 5° C. The mixture was stirred at 5° C. for 1 hour and then for 18 hours at ambient temperature. The insolubles were removed by filtration and the volatiles were removed from the filtrate by evaporation. The residue was purified by column chromatography eluting with ethyl acetate/methanol (100/0 increasing to 95/5) to give 4-(4-bromo-2-fluoroanilino)-6-methoxy-7-(3-methylthiopropoxy)quinazoline (400 mg, 50%).

m.p. 250–252° C.; $^1$H NMR Spectrum: (DMSOd$_6$) 2.08(t, 2H); 2.64(t, 2H); 4.00(s, 3H); 4.28(t, 2H); 7.40(s, 1H); 7.48–7.58(m, 2H); 7.78(d, 1H); 8.30(s, 1H); 8.80(s, 1H); MS-ESI: 452 [MH]$^+$.

EXAMPLE 32

A solution of OXONE, (trade mark of E.I du Pont de Nemours & Co., Inc), (800 mg) in water (4.5 ml) was added to a solution of 4-(4-bromo-2-fluoroanilino)-6-methoxy-7-(3-methylthiopropoxy)quinazoline (300 mg, 0.66 mmol), (prepared as described in Example 31), in methanol (15 ml) and the mixture was stirred for 4 hours at ambient temperature. The mixture was diluted with methylene chloride, was washed with aqueous sodium hydrogen carbonate solution, dried (MgSO$_4$) and the solvent was removed by evaporation. The residue was triturated with ethyl acetate/hexane, collected by filtration and dried to give 4-(4-bromo-2-fluoroanilino)-6-methoxy-7-(3-methylsulphonylpropoxy)quinazoline (235 mg, 73%).

m.p.>250° C. $^1$H NMR Spectrum: (DMSOd$_6$) 2.30(t, 2H); 3.20(s, 3H); 3.30(t, 2H); 4.10(s, 3H); 4.30(t, 2H); 7.38(s, 1H); 7.5–7.6(m, 2H); 7.78(d, 1H); 8.30(s, 1H); 8.80(s, 1H); MS-ESI: 484 [MH]$^+$; Elemental analysis: Found C, 42.8; H, 3.8; N, 7.8; C$_{19}$H$_{19}$N$_3$O$_4$BrFS 0.5H$_2$O Requires C, 43.1; H, 3.9; N, 7.9%.

EXAMPLE 33

1,1'-(Azodicarbonyl)dipiperidine (355 mg, 1.4 mmol) was added in portions to a mixture of 4-(4-chloro-2-fluoroanilino)-7-hydroxy-6-methoxyquinazoline (150 mg, 0.47 mmol), (prepared as described for the starting material in Example 2), 2-(cyclopentyloxy)ethanol (91 mg, 0.7 mmol), (U.S. Pat. No. 4,515,814), and tributylphosphine (284 mg, 1.4 mmol) in methylene chloride (6 ml) at 0° C. The mixture was then allowed to warm to ambient temperature and stirred for 3.5 hours. Ether (3 ml) was added and the insolubles were removed by filtration and the volatiles were removed from the filtrate by evaporation. The residue was dissolved in acetone and 1M ethereal hydrogen chloride (0.6 ml) was added. The mixture was left to stand for 60 hours and the precipitate was collected by filtration, washed with acetone and dried to give 4-(4-chloro-2-fluoroanilino)-7-(2-cyclopentyloxyethoxy)-6-methoyxquinazoiline hydrochloride (130 mg, 60%).

$^1$H NMR Spectrun: (DMSOd$_6$) 1.4–1.8(m, 8H); 3.75(t, 2H); 4.00(s, 4H); 4.30(t, 2H); 737(s, 1H); 7.42(dd, 1H); 7.60(t, 1H); 7.64(dd, 1H); 8.25(s, 1H); 8.78(s, 1H); MS-ESI: 432 [MH]$^+$; Elemnental analysis: Found C, 55.8; H, 5.0; N, 8.8; C$_{22}$H$_{23}$N$_3$O$_3$ClF 1H$_2$O 1HCl Requires C, 56.0; H, 5.2; N, 8.9%.

EXAMPLE 34

Diethyl azodicarboxylate (0.94 ml, 6 mmol) was added dropwise to a mixture of triphenylphosphine (1.57 g, 6 mmol), 4-(4-chloro-2-fluoroanilino)-7-hydroxy-6-methoxyquinzline (640 mg, 2 mmol), (prepared as described for the starting material in Example 2), and N-(tert-butoxycarbnyl)ethanolamine (0.354 g, 2.2 mmol) in methylene chloride (20 ml) at 0° C. The reaction mixture was allowed to warm to ambient temperature and stirred for 4 hours. The reaction mixture was diluted with methylene chloride, washed with aqueous sodium hydrogen carbonate solution, water and then brine, dried (MgSO$_4$) and the solvent removed by evaporation. The residue was purified by column chromatography eluting with methylene chloride/methanol/aqueous ammonia (100/8/1). The product was recystallised from acetonitrile, collected by filtration, washed with ethyl acetate and dried to give 7-(2-[N-tert-butoxycarbonylamino]ethoxy)-4-(4-chloro-2-fluoroanilino)-6-methoxyquinazoline (235 mg, 25%).

m.p. 190–191° C.; $^1$H NMR Spectrum: (DMSOd$_6$) 1.36(s, 9H); 3.34(q, 2H); 3.91(s, 3H); 4.15(t, 2H); 6.98(t, 1H); 7.19(s, 1H); 7.33(dd, 1H); 7.56(m, 2H); 7.78(s, 1H); 8.34(s, 1H); 9.51(s, 1H); 9.51(s, 1H); MS-ESI: 463 [MH]$^+$; Elemental analysis: Found C, 57.0; H, 5.1; N, 12.5; C$_{22}$H$_{24}$N$_4$O$_4$ClF Requires C, 57.1; H, 5.1; N, 12.1%.

EXAMPLE 35

Sodium hydride (55 mg of a 60% dispersion in mineral oil, 1.1 mmol) was added to a solution of glutarimide (120 mg, 1.06 mmol) in DMF (5 ml) at ambient temperature under argon and the mixture stirred for 30 minutes. 7-(2-Bromoethoxy)-4-(4-chloro-2-fluoroanilino)-6-methoxyquinazoline (428 mg, 1 mmol), (prepared as described for the starting material in Example 62), in DMF (2 ml) was added and the resulting pale green solution was stirred for 18 hours and then quenched with water. The volatiles were removed by evaporation, and the residue was partitioned between water and ethyl acetate. The organic phase was separated and washed with water and then dried (MgSO$_4$). The solvent was removed by evaporation, and the residue was purified by column chromatography eluting with ethyl acetate then ethyl acetatemtal (9/1). The purified product was recrystallised from ethyl acetate and hexane, collected by filtration and washed with ether to give 4-(4-chloro-2-fluoroanilino)-7-(2-(2,6-dioxopiperidino)ethoxy)-6-methoxyquinizoline (252 mg, 55%).

m.p. 202–203° C.; $^1$H NMR Spectrum: (DMSOd$_6$) 1.84 (m, 2H); 2.63(t, 4H); 3.91(s, 3H); 4.08(t, 2H); 4.17(t, 2H); 7.10(s, 1H); 7.34(dd, 1H); 7.55(m, 2H); 7.79(s, 1H); 8.34(s, 1H); 9.52(s, 1H); MS-ESI: 459 [MH]$^+$; Elemental analysis: Found C, 57.2; H, 4.2; N, 11.9; C$_{22}$H$_{20}$N$_4$O$_4$ClF Requires C, 57.6; H, 4.3; N, 12.2%.

EXAMPLE 36

Isobutyl chloroformate (88 mg, 5.9 mmol) was added to a stirred solution of 7-(3-aminopropoxy)-4-(4-chloro-2-fluoroanilino)-6-methoxyquinazoline trifluoroacetate (151 mg, 0.4 mmol) and triethylamine (0.2 ml, 1.4 mmol) in THF (15 ml). The reaction mixture was stirred at ambient temperature for 30 minutes and the volatiles were removed by evaporation. The residue was dissolved in methylene chloride, the solution was washed with aqueous sodium hydrogen carbonate solution and then brine, dried (MgSO$_4$) and the solvent was removed by evaporation. The residue was recrystallised from acetonitrile to give 4-(4-chloro-2-fluoroanilino)-7-(3-[N-isobutoxycarbonylamino]propoxy)-6-methoxyquinazoline (41.2 mg, 20%) as a white solid.

m.p. 136–137° C.; $^1$H NMR Spectrum: (DMSOd$_6$) 0.87 (d, 6H); 1.80(m, 1H); 1.93(t, 2H); 3.16(q, 2H); 3.71(d, 2H); 3.94(s, 3H); 4.15(t, 2H); 7.16(s, 2H); 7.32(dd, 1H); 7.55(m, 2H); 7.79(s, 1H); 8.34(s, 1H); 9.50(s, 1H); MS-ESI: 477 [MH]$^+$; Elemental analysis: Found C, 57.1; H, 4.9; N, 11.6; $C_{23}H_{26}N_4O_4ClF$ Requires C, 57.1; H, 5.5; N, 11.6%.

The starting material was prepared as follows:

A solution of di-tert-butyl dicarbonate (32 g, 148 mmol) in methylene chloride (70 ml) was added dropwise to a stid solution of 3-amino-1-propanol (10.1 g, 134 mmol) in methylene chloride (100 ml). The reaction mixture was stirred overnight and was then washed with saturated aqueous sodium hydrogen carbonate solution, water and then brine. The organic layer was dried (MgSO$_4$) and the volatiles were removed by evaporation to give 3-(N-tert-butoxycarbonylamino)-1-propanol (23.3 g, 100%) as a colourless oil.

$^1$H NMR Spectrum: (CDCl$_3$) 1.48(s, 9H); 1.68(m, 2H); 2.90(br s, 1H); 3.30(m, 2H); 3.65(m, 2H); 4.78(br s, 1H); MS-ESI: 176 [MH]$^+$.

Triphenylphosphine (2.46 g, 9.3 mmol) was added to a suspension of 4-(4-chloro-2-fluoroanilino)-7-hydroxy-6-methoxyquinazoline (1.0 g, 3.1 mmol), (prepared as described for the starting material in Example 2), in methylene chloride (25 ml) and the suspension stirred at 0° C. for 30 minutes. A solution of 3-(N-tert-butoxycarbonylamino)-1-propanol (0.65 g, 3.7 mmol) in methylene chloride (3 ml) was added and then diethyl azodicarboxylate (1.47 ml, 7.6 mmol) was added dropwise. The reaction mixture was allowed to warm to ambient temperature and stirred for 18 hours. The reaction mixture was diluted with methylene chloride and washed with aqueous sodium hydrogen carbonate solution, water and then brine. The resultant solution was dried (MgSO$_4$) and the solvent removed by evaporation. The residue was purified by column chromatography eluting with methylene chloride/methanol/triethylamine (100/0/0 and then 95/4/1) to give 7-(3-(N-tert-butoxycarbonylamino)propoxy)-4-(4-chloro-2-fluororanilino)-6-methoxyquinazoline (620 mg, 42%).

$^1$H NMR Spectrum: (DMSOd$_6$) 1.36(s, 9H); 1.89(t, 2H); 3.11 (q, 2H); 3.91(s, 3H); 4.14(t, 2H); 6.89(m, 1H); 7.16(s, 1H); 7.31(dd, 1H); 7.56(m, 2H); 7.77(s. 1H); 8.32(s, 1H); 9.51(s, 1H); MS-ESI: 477 [MH]$^+$.

7-(3-(N-tert-butoxycarbonylamino)propoxy)-4-(4-chloro-2-fluoroanlno)-6-methoxyquinazoline (610 mg, 1.28 mmol) was added slowly to TFA (10 ml). The reaction was stirred at ambient temperature for 2 hours and the volatiles were removed by evaporation and by azeotroping with toluene to give 7-(3-aminopropoxy)-4-(4-chloro-2-fluoroanilino)-6-methoxyquinoline trifluoroacetate (455 mg, 94%) as an oil.

EXAMPLE 37

A mixture of 7-(2-bromoethoxy)-4-(4-chloro-2-fluoroanilino)-6-methoxyquinazoline (425 mg, 1 mmol), (repared as described for the starting material in Example 62), and 1-methyl-4-(methylamino)piperidine (128 mg, 1 mmol) in N,N-dimethylacetamide (2 ml) was stirred at 65° C. for 3 hours. The volatiles were removed by evaporation and the residue was purified by column chromatography eluting with methylene chloride/methanol/aqueous ammonia (75/8/1). The purified product was triturated with ether, collected by filtration, washed with ether and dried to give 4-(4-chloro-2-fluoroanilino)-6-methoxy-7-(2-([N-methyl-N-(1-methylpiperidin-4-yl)]amino)ethoxy)quinazoline (180 mg, 38%) as a pale yellow powder.

m.p. 191–192° C.; $^1$H NMR Spectrum: (DMSOd$_6$) 1.44 (m, 2H); 1.70(m, 2H); 1.86(m, 2H); 2.15(s, 3H); 2.30(s, 3H); 2.78(m, 2H); 2.88(t, 2H); 3.94(s, 3H); 4.18(t, 2H); 7.19(s, 1H); 7.33(m, 1H); 7.52(m, 1H); 7.58(t, 1H); 7.78(s, 1H); 8.34(s, 1H); 9.48(s, 1H); MS-ESI: 474 [MH]$^+$; Elemental analysis: Found C, 60.9; H, 6.3; N, 14.7; $C_{24}H_{29}N_5O_2ClF$ Requires C, 60.8; H, 6.2; N, 14.8%.

EXAMPLE 38

1,1'-(Azodicarbonyl)dipiperidine (560 mg, 2.2 mmol) was added in portions to a mixture of 4-(4-chloro-2-fluoroanilino)-7-hydroxy-6-methoxyquinazoline (240 mg, 0.75 mmol), (prepared as described for the starting material in Example 2), tetrahydro-3-furanmethanol (90 mg, 0.88 mmol) and tributylphosphine (440 mg, 2.2 mmol) in methylene chloride (12 ml) and the mixture stirred for 18 hours. The mixture was diluted with ether, and the resulting precipitate was removed by filtration. The solvent was removed from the filtrate by evaporation, and the residue was dissolved in acetone and ethereal hydrogen chloride (0.75 ml of a 1M solution, 0.75 mmol) was added. The mixture was diluted with ether and the resulting precipitate was collected by filtration. The solid was purified by column chromatography eluting with methylene chloride/acetonitrile/methanol (a gradient firm 50/50/1 to 50/50/2). The purified product was triturated with ether, collected by filtration and dried to give 4-(4-chloro-2-fluoroanino)-6-methoxy-7 (tetrahydrofuran-3-ylmethoxy)quinazoline (93mg, 31%).

m.p. 201–202° C.; $^1$H NMR Spectrum: (DMSOd$_6$) 1.70 (m, 1H); 2.05(m, 1H); 2.72(m, 1H); 3.56(m, 1H); 3.66(q, 1H); 3.79(m, 2H); 3.94(s, 3H); 4.08(m, 2H); 7.20(s, 1H); 7.32(m, 1H); 7.52(dd, 1H); 7.58(t, 1H); 7.78(t, 1H); 8.35(s, 1H); 9.52(s, 1H); MS-ESI: 404 [MH]$^+$; Elemental analysis: Found C, 59.2; H, 4.6; N, 10.6; $C_{20}H_{19}N_3O_3ClF$ Requires C, 59.5; H, 4.7; N, 10.4%.

EXAMPLE 39

1,1'-(Azodicarbonyl)dipiperidine (5.6 g, 22 mmol) was added in portions to a mixture of 4-(4chloro-2-fluoroanilino)-7-hydroxy-6-methoxyquinazoline (2.4 g, 7.5 mmol), (prepared as described for the starting material in Example 2), tributylphosphine (4.4 g, 22 mmol) and 1-(2-hydroxyethyl)-2-pyrrolidinone (1.1 g, 8.5 mmol) in methylene chloride (105 ml). The mixture was stirred for 18 hours, diluted with ether (100 ml) and the resulting precipitate was removed by filtration. The volatiles were removed from the filtrate by evaporation, and the residue was dissolved in acetone and ethereal hydrogen chloride (15 ml of a 1M solution, 15 mmol) was added. The solid was collected by filtration and was purified by column chromatography eluting with methylene chloride/methanol/aqueous ammonia (150/8/1). The purified product was dissolved in acetone and ethereal hydrogen chloride (15 ml of a 1M solution, 15 mmol) was added. The resulting precipitate was collected by filtration, washed with ether and dried to give 4-(4-chloro-2-flooroanilino)-6-methoxy-7-(2-(2-oxopyrrolidin-1-yl) ethoxy)quinazoline hydrochloride (2.1 g, 60%).

m.p. 250–252° C.; $^1$H NMR Spectrum: (DMSOd$_6$) 1.92 (m, 2H); 2.22(t, 2H); 3.52(t, 2H); 3.68(t, 2H); 4.02(s, 3H);

4.30(t, 2H); 7.38(s, 1H); 7.42(m, 1H); 7.58(t, 1H); 7.66(dd, 1H); 8.35(s, 1H); 8.79(s, 1H); 11.69(br s, 1H); MS-ESI: 431 [MH]$^+$; Elemental analysis: Found C, 53.5; H, 4.4; N, 12.2; $C_{21}H_{20}N_4O_3ClF$ 0.1H$_2$O 1HCl Requires C, 53.8; H, 4.6; N, 11.9%.

EXAMPLE 40

1,1'-(Azodicarbonyl)dipiperidine (525 mg, 2.1 mmol) was added in portions to a mixture of 4-(4-chloro-2-fluroanilino)-7-hydroxy-6-methoxyquinazoline (225 mg, 7.0 mmol), (prepared as described for the starting material in Example 2), tributylphosphine (420 mg, 2.1 mmol) and 1-(2-hydroxyethyl)-2-imidazolidinone (100 mg, 7.7 mmol) in methylene chloride (10 ml). The mixture was stirred for 18 hours, diluted with ether and the resulting precipitate was removed by filtration. The volatiles were removed from the filtrate by evaporation and the residue was purified by column chromatography eluting with methylene chloride/methanol/aqueous ammonia (150/81). The purified product was triturated with ether collected by filtration, washed with ether and dried to give 4-(4-chloro-2-fluoroanilino)-6-methoxy-7-(2-(2-oxoimidazolidin-1-yl)ethoxy)quinazoline (19 mg, 6%).

m.p. >250° C. $^1$H NMR Spectrum: (DMSOd$_6$) 3.27(t, 2H); 3.53(m, 4H); 3.97(s, 3H); 4.27(t, 2H); 6.39(s, 1H); 7.26(s, 1H); 7.35(m, 1H); 7.57(dd, 1H); 7.61(t, 1H); 7.82(s, 1H); 8.38(s, 1H); 9.55(s, 1H); MS-ESI: 432 [MH]$^+$; Elemental analysis: Found C, 53.7; H, 4.4; N, 15.4; $C_{20}H_{19}N_5O_3ClF$ 1H$_2$O Requires C, 53.4; H, 4.7; N, 15.6%.

EXAMPLE 41

1,1'-(Azodicarbonyl)dipiperidine (525 mg, 2.1 mmol) was added in portions to a mixture of 4-(4-chloro-2-fluoroanilino)-7-hydroxy-6-methoxyquinazoline (225 mg, 7.0 mmol), (prepared as described for the starting material in Example 2), tributylphosphine (420 mg, 2.1 mmol) and 4-(2-hydroxyethyl)-1,1-dioxothiomorpholine (140 mg, 7.8 mmol) in methylene chloride (10 ml). The mixture was stirred for 18 hours, diluted with ether and the resulting precipitate was removed by filtration. The volatiles were removed from the filtrate by evaporation, and the residue was dissolved in acetone and ethereal hydrogen chloride (14 ml of a 1M solution, 14 mmol) and the precipitate was collected by filtration. The residue was purified by column chromatography eluting with methylene chloride/methanol/aqueous ammonia (150/8/1). The purified product was triturated with ether/methylene chloride collected by filtration and dried to give 4-(4-chloro-2-fluoroanilino)-7-(2-(1,1-dioxothiomorpholino)ethoxy)-6-methoxyquinazoline (120 mg, 36%).

m.p. 246–249° C.; $^1$H NMR Spectrum: (DMSOd$_6$) 3.03(t, 2H); 3.10(br s, 8H); 3.95(s, 3H); 4.27(t, 2H); 7.24(s, 1H); 7.38(m, 1H); 7.53(dd, 1H); 7.58(t, 1H); 7.80(s, 1H); 8.35(s, 1H); 9.52(s, 1H); MS-ESI: 481 [MH]$^+$; Elemental analysis: Found C, 52.0; H, 4.6; N, 11.9; S 6.6; $C_{21}H_{22}N_4O_4ClFS$ Requires C, 52.4; H, 4.6; N, 11.6; S 6.7%.

EXAMPLE 42

1-(3-Dimethylaminopropyl)-3-ethylcarbodiimide hydrochloride (94 mg, 4.9 mmol) was added to a mixture of 7-(3carboxypropoxy)4-(4-chloro-2-fluoroanilino)-6-methoxyquinazoline (164 mg, 0.4 mmol), morpholine (0.11 g; 1.26 mmol) and 4-dimethylaminopyridine (200 mg, 1.64 mmol) in DMF (5 ml). The reaction mixture was stirred at ambient temperature for 24 hours and the volatiles were removed by evaporation. Water was added to the residue and the aqueous mixture was extracted with methylene chloride (3×30 ml). The extracts were combined and the solvent removed by evaporation. The residue was triturated with ether and the precipitate was collected by filtration. The solid was purified by column chromatography eluting with methylene chloride/methanol/aqueous ammonia (100/8/1). The purified product was triturated with acetone, collected by filtration and dried to give 4-(4-chloro-2-fluoroanilino)-6-methoxy-7-(3-morpholinocarbonylpropoxy)quinazoline (88 mg, 46%).

m.p. 216–217° C.; $^1$H NMR Spectrum: (DMSOd$_6$) 2.02 (m, 2H); 2.5(m, 2H); 3.45(m, 4H); 3.55(m, 4H); 3.92(s, 3H); 4.15(t, 2H); 7.18(s, 1H); 7.32(d, 1H); 7.55(m, 2H); 7.78(s, 1H); 8.34(s, 1H); 9.52(s, 1H); MS-ESI: 475 [MH]$^+$; Elemental analysis: Found C, 58.2; H, 5.2; N, 12.2; $C_{23}H_{24}N_4O_4ClF$ Requires C, 58.2; H, 5.1; N, 11.8%.

The starting material was prepared as follows:

Ethyl 4chlorobutyrate (0.154 ml, 1.1 mmol) was added to a mixture of 4-(4-chloro-2-fluoroanilino)-7-hydroxy-6-methoxyquinazoline (319.5 mg, 1 mmol), (prepared as described for the starting material in Example 2), and anhydrous potassium carbonate (690 mg, 5 mmol) in DMF (10 ml). The mixture was stirred and heated at 105° C. for 4 hours then allowed to cool. The mixture was diluted with methylene chloride and the insolubles were removed by filtration. The solvent was removed from the filtrate by evaporation and the residue was purified by column chromatography eluting with methylene chloride/methanol/aqueous ammonia (1008/1). The purified product was triturated with ether collected by filtration and dried to give 4-(4-chloro-2-fluoroanilino)-7-(3-ethoxycarbonylpropoxy)-6-methoxyquinazoline (230 mg, 53%).

$^1$H NMR Spectrum: (DMSOd$_6$) 1.18(t, 3H); 2.02(m, 2H); 2.48(m, 2H); 3.94(s, 3H); 4.06(q, 2H); 4.15(t, 2H); 7.18(s, 1H); 7.32(m, 1H); 7.54(m, 2H); 7.78(s, 1H); 8.34(s, 1H); 9.52(s, 1H); MS-ESI: 434 [MH]$^+$; Elemental analysis: Found C, 58.0; H, 4.8; N, 9.8; $C_{21}H_{21}N_3O_4ClF$ Requires C, 58.1; H, 4.9; N, 9.7%.

A mixture of 4-(4-chloro2-fluoroanilino)-7-(3-ethoxycarbonylpropoxy)6-methoxyquinazoline (220 mg, 0.5 mmol) in aqueous sodium hydroxide solution (4 ml of a 2M solution, 8 mmol), water (2 ml) and methanol (0.5 ml) was stirred and heated at 40° C. for 3 hours. The mixture was allowed to cool and was then acidified with 2M hydrochloric acid. The resulting white precipitate was collected by filtration and washed with acetone and water to give 7-(3carboxypropoxy)-4-(4-chloro-2-fluoroanilino)-6-methoxyquinazoline (170 mg, 83%).

EXAMPLE 43

1-(3-Dimethylaminopropyl)-3-ethylcarbodiimide hydrochloride (145 mg, 0.75 mmol) was added to a mixture of 7-(3-carboxypropoxy)-4-(4-chloro-2-fluoroanilino)-6-methoxyquinazoline (250 mg, 0.62 mmol), (prepared as described for the starting material in Example 42), 1-methylpiperazine (0.21 ml, 2.32 mmol) and 4-dimethylaminopyridine (300 mg, 2.46 mol) in DMF (7.5 ml). The reaction mixture was stirred at ambient temperature for 24 hours and the volatiles were removed by evaporation. Water was added to the residue and the aqueous mixture was extracted with methylene chloride (3×30 ml). The combined organic extracts were washed with brine and the solvent was removed by evaporation. The residue was triturated with ether and the precipitate was collected by filtration. The solid was purified by column chromatography eluting with methylene chloride/methanol/aqueous ammonia (100/8/1).

The purified product was triturated with ether collected by filtration and dried to give 4-(4-chloro-2-fluoroanilino)-6-methoxy-7-(3-(4-methylpiperazin-1-ylcarbonyl)propoxy)quinazoline (133 mg, 44%).

m.p. 248–250° C. $^1$H NMR Spectrum: (DMSOd$_6$) 2.00(t, 2H); 2.15(s, 3H); 2.25(m, 4H); 2.45(m, 2H); 3.45(m, 4H); 3.92(s, 3H); 4.15(t, 2H); 7.18(s, 1H); 7.30(d, 1H); 7.55(m, 2H); 7.78(s, 1H); 8.34(s, 1H); 9.52(s, 1H); MS-ESI: 488 [MH]$^+$; Elemental analysis: Found C, 58.6; H, 5.5; N, 13.9; C$_{24}$H$_{27}$N$_5$O$_3$ClF 0.2H$_2$O Requires C, 58.6; H, 5.6; N, 14.3%.

EXAMPLE 44

Oxalyl chloride (0.4 ml, 2.2 mmol) was added to a suspension of 7-(3-carboxypropoxy)-4-(4-chloro-2-fluoroanilino)-6-methoxyquinazoline (260 mg, 0.64 mmol), (prepared as described for the starting material in Example 42), in methylene chloride (25 ml) followed by 1 drop of DMF. The mixture was stirred at ambient temperature for 2.5 hours and the volatiles were removed by evaporation. A solution of pyrrolidine (0.13 ml, 2.1 mmol) in N,N-dimethylacetamide (8 ml) was added to the solid residue and the mixture was stirred at ambient temperature for 2 hours. The volatiles were removed by evaporation and the residue was purified by column chromatography eluting with methylene chloride/methanol/aqueous ammonia (100/8/1). The purified product was triturated with acetone, collected by filtration and dried to give 4-(4-chloro-2-fluoroanilino)-6-methoxy-7-(3-pyrrolidin-1-ylcarbonylpropoxy)quinazoline (206 mg, 70%).

m.p. 254–256° C.; $^1$H NMR Spectrum: (DMSOd$_6$) 1.76 (m, 2H); 1.85(m, 2H); 2.02(m, 2H); 2.41(t, 2H); 3.26(t, 2H); 3.38(t, 2H); 3.95(s, 3H); 4.15(t, 2H); 7.18(s, 1H); 7.32(d, 1H); 7.55(m, 2H); 7.78(s, 1H); 8.34(s, 1H); 9.52(s, 1H); MS-ESI: 459 [ME]$^+$; Elemental analysis: Found C, 59.9; H, 5.3; N, 12.0; C$_{23}$H$_{24}$N$_4$O$_3$ClF Requires C, 60.2; H, 5.3; N, 12.2%.

EXAMPLE 45

A mixture of 4-(4-chloro-2-fluoroanilino)-7-(2,2-dimethoxyethoxy)-6-methoxyquinazoline (210 mg, 0.52 mmol), water (5 ml) and TFA (5 ml) was stirred at ambient temperature for 3 hours then heated at 60° C. for 1 hour. The solution was allowed to cool, then diluted with water and the resulting precipitate was collected by filtration and dried. The solid was dissolved in methanol (10 ml) and cyclopentylamine (0.057 ml, 0.57 mmol) and dried 3 Å molecular sieves (2.5g) were added. The mixture was stirred for 30 minutes, glacial acetic acid (0.20 ml, 3.2 mmol) and sodium cyanoborohydride (150 mg, 2.4 mmol) were added and the reaction stirred for 4 hours then left to stand for 18 homs. The insolubles were removed by filtration and the solvent was removed from the filtrate by evaporation. The residue was purified by column chromatography eluting with methylene chloride/methanol/aqueous ammonia (1008/1). The purified product was triturated with ether/hexane, collected by filtration and dried to give 4-(4-chloro-2-fluoroanilino)-7-(2-cyclopentylaminoethoxy)-6-methoxyquinazoline (80 mg, 36%).

m.p. 171–173° C.; $^1$H NMR Spectrum: (DMSOd$_6$) 1.55 (m, 8H); 2.94(t, 2H); 3.08(m, 1H); 3.94(s, 3H); 4.19(t, 2H); 7.19(s, 1H); 7.33(m, 1H); 7.52(dd, 1H); 7.59(t, 1H); 7.78(s, 1H); 8.34(s, 1H); 950(s, 1H); MS-ESI: 431 [MH]$^+$ The starting material was prepared as follows:

Bromoacetaldehyde dimethyl acetal (0.74 ml, 3.1 mmol) was added to a mixture of 4-(4-chloro-2-fluoroanilino)-7-hydroxy-6-methoxyquinazoline (10 g, 3.13 mmol), (prepared as described for the starting material in Example 2), and anhydrous potassium carbonate (2.16 g, 15.6 mmol) in DMF (30 ml). The mixture was stirred and heated at 110° C. for 4 hours, then allowed t6 cool and the volatiles were removed by evaporation. Water was added to the residue and the aqueous mixture was extracted with methylene chloride (×4). The extracts were combined, washed with brine and dried by filtration through phase separating paper. The volatiles were removed by evaporation, the residue was triturated with ether, collected by filtration and dried to give 4-(4-chloro-2-fluoroanilino)-7-(2,2-dimethoxyethoxy)-6-methoxyquinazoline (440 mg, 35%).

$^1$H NMR Spectrum: (DMSOd$_6$) 3.36(s, 6H); 3.94(s, 3H); 4.05(d, 2H); 4.75(t, 1H); 7.22(s, 1H); 7.32(m, 1H); 7.52(m, 1H); 7.58(t, 1H); 7.80(s, 1H); 8.35(s, 1H); 9.52(s, 1H); MS-ESI: 408 [MH]$^+$

EXAMPLE 46

Diethyl azodicarboxylate (1.55 ml, 9.89 mmol), 4-(4-bromo-2-fluoroanilino)-7-hydroxy-6-methoxyquinazoline (1.2g, 3.3 mmol), (prepared as described for the starting material in Example 48), and a solution of (E)-4-(pyrrolidin-1-yl)but-2-en-1-ol (697 mg, 4.9 mmol), (prepared as described for the starting material in Example 17), in methylene chloride (5 ml) were added successively to a solution of triphenylphosphine (2.59 g, 9.89 mmol) in methylene chloride (150 ml) cooled at 5° C. The mixture was stirred at ambient temperature for 10 minutes then methylene chloride (100 ml) was added followed successively by triphenylphosphine (432 mg, 1.6 mmol), (E)-4-(pyrrolidin-1-yl)but-2-en-1-ol (232 mg, 1.6 mmol) and diethyl azodicarboxylate (246 µl, 1.6 mmol). The mixture was stirred at ambient temperature for 30 minutes and then the solvent was removed by evaporation. The residue was purified by column chromatography eluting with methylene chloride/methanol (8/2 followed by 7/3 and 6/4). The semi-purified product was repurified by column chromatography eluting with methylene chloride/methanol (8/2 followed by 7.5/2.5). The purified product was dissolved in methylene chloride, 3.7M ethereal hydrogen chloride (3 ml) was added and the volatiles were removed by evaporation. The residue was triturated with ether, collected by filtration and dried under vacuum to give (E)-4-(4-bromo-2-fluoroanilino)-6-methoxy-7-(4-pyrrolidin-1-ylbut-2-en-1-yloxy)quinazoline hydrochloride (600 mg, 32%).

$^1$H NMR Spectrum: (DMSOd$_6$; CF$_3$COOD) 1.8–1.9(m, 2H); 2.0–2.1(m, 2H); 3.0–3.1(m, 2H); 3.45–3.55(m, 2H); 3.88(d, 2H); 4.01(s, 3H); 4.9(d, 2H); 6.0(td, 1H); 6.3(td, 1H); 7.41(s, 1H); 7.5–7.65(m, 2H); 7.82(d, 1H); 8.13(s, 1H); 8.88(s, 1H); MS-(EI): 487 [M.]$^+$; Elemental analysis: Found C, 48.2; H, 4.9; N, 9.6; C$_{23}$H$_{24}$N$_4$O$_2$BrF 0.5H$_2$O 2HCl Requires C, 48.5; H, 4.8; N, 9.8%.

EXAMPLE 47

Diethyl azodicarboxylate (261 mg, 1.5 mmol) was added dropwise to a mixture of 4-(4-chloro-2-fluoroanilino)-7hydroxy-6-methoxyquinazoline (160 mg, 0.5 mmol), (prepared as described for the starting material in Example 2), triphenylphosphine (393 mg, 1.5 mmol) and 1-(3-hydroxypropyl)-2-pyrrolidinone (107 mg, 0.75 mmol) in methylene chloride (5 ml) under nitrogen. The mixture was stirred for 20 minutes at ambient temperature and then purified by pouring directly onto a column of silica eluting with methylene chloride/ethyl acetate/methanol (60/35/5 followed by 60/30/10). The purified product was triturated with ether and collected by filtration. The solid was dissolved in ethyl acetate and treated with 3M hydrogen chloride in ethyl acetate (0.4 ml). The precipitate was collected by filtration, washed with ethyl acetate and dried under vacuum to give 4-(4-chloro-2-fluoroanilino)-6-methoxy-7-(3-(2-oxopyrrolidin-1-yl)propoxy)quinazoline hydrochloride (170 mg, 70%).

$^1$H NMR Spectrum: (DMSOd$_6$; CF$_3$COOD) 1.9–2.0(m, 2H); 2.0–2.1(m, 2H); 2.21(t, 2H); 3.4–3.5(m, 4H); 4.02(s, 3H); 4.20(s, 3H); 4.20(t, 2H); 7.32(s, 1H); 7.46(dd, 1H); 7,63(t, 1H); 7.71(dd, 1H); 8.17(s, 1H); 8.87(s, 1H); MS-ESI: 445 [MH]$^+$; Elemental analysis: Found C, 54.9; H, 4.7; N, 11.6; C$_{22}$H$_{22}$N$_4$O$_3$ClF0.3H$_2$O 0.85HCl Requires C, 54.9; H, 4.9; N, 11.6%.

The starting material was prepared as follows:

A solution of γ-butyrolactone (8.6g, 0.1 mol) and 3-amino-1-propanol (9 g, 0.12 mol) was heated at reflux for 18 hours. The crude product mixture was distilled under reduced pressure to give 1-(3-hydroxypropyl)-2-pyrrolidinone (2.5 g. 17%).

b.p. ~130° C. under ~0.05 mmHg; $^1$H NMR Spectrum: (CDCl$_3$) 1.7–1.8(m, 3H); 2.0–2.15(m, 2H); 2.44(t, 2H); 3.4–3.5(m, 4H); 3.54(t, 2H); MS-(EI): 143[M.]$^+$.

EXAMPLE 48

Using a method analogous to that in Example 47, 4-(4-bromo-2-fluoroanilino)-7-hydroxy-6-methoxyquinazoline (146 mg, 0. mmol) in methylene chloride (5 ml) was treated with 1-(3-hydroxypropyl)-2-pyrrolidinone (86 mg, 0.6 mmol), triphenylphosphine (314 mg, 1.2 mmol) and diethyl azodicarboxylate (209 mg, 1.2 mmol) and was purified and isolated to give 4-(4-bromo-2-fluoroanilino)-6-methoxy-7-(3-(2-oxypyrrolidin-1-yl)propoxy)quinazoline hydrochloride (140 mg, 67%).

$^1$H NMR Spectrum: (DMSOd$_6$; CF$_3$COOD) 1.9–2.0(m, 2H); 2.0–2.1(m, 2H); 2.21(t, 2H); 3.4–3.5(m, 4H); 4.02(s, 3H); 4.20(t, 2H); 7.32(s, 1H); 7.5–7.65(m, 2H); 7.82(d, 1H); 8.15(s, 1H); 8.87(s, 1H); MS-ESI: 490 [MH]$^-$; Elemental analysis: Found C, 49.9; H, 4.4; N, 10.5; CH$_{22}$H$_{22}$N$_4$O$_3$BrF 0.2H$_2$O 0.95HCl Requires C, 50.1; H, 4.5; N, 10.6%.

The starting material was prepared as follows:

A solution of 7-benzyloxy-4-chloro-6-methoxyquinazoline (8.35 g, 27.8 mmol), (prepared as described for the starting material in Example 1), and 4-bromo-2-fluoroaniline (5.65 g, 29.7 mmol) in 2-propanol (200 ml) was heated at reflux for 4 hours. The resulting precipitate was collected by filtration, washed with 2-propanol and then ether and dried under vacuum to give 7-benzyloxy-4-(4-bromo-2-fluoroanilino)-6-methoxyquinazoline hydrochloride (9.46 g, 78%).

$^1$H NMR Spectrum: (DMSOd$_6$; CD$_3$COOD) 4.0(s, 3H); 5.37(s, 2H); 7.35–7.5(m, 4H); 7.52–7.62(m, 4H); 7.8(d, 1H); 8.14(9s, 1H); 8.79(s, 1H); MS-ESI: 456 [MH]$^+$; Elemental analysis: Found C, 54.0; H, 3.7; N, 8.7; C$_{22}$H$_{17}$N$_3$O$_2$BrF 0.9HCl Requires C, 54.2; H, 3.7; N, 8.6%.

A solution of 7-benzyloxy-4-(bromo-2-fluoroanilino)-6-methoxyquinazoline hydrochloride (9.4 g, 19.1 mmol) in TFA (90 ml) was heated at reflux for 50 minutes. The mixture was allowed to cool and was poured on to ice. The resulting precipitate was collected by filtration and dissolved in methanol (70 ml). The solution was adjusted to pH9–10 with concentrated aqueous ammonia solution. The mixture was concentrated to half initial volume by evaporation. The resulting precipitate was collected by filtration, washed with water and then ether, and dried under vacuum to give 4-(4-bromo-2-fluoroanilino)-7-hydroxy-6-methoxyquinazoline (5.66 g, 82%).

$^1$H NMR Spectrum: (DMSOd$_6$; CD$_3$COOD) 3.95(s, 3H); 7.09(s, 1H); 7.48(s, 1H); 7.54(t, 1H); 7.64(d, 1H); 7.79(s, 1H); 8.31(s, 1H); MS-ESI: 366 [MH]$^+$; Elemental analysis: Found C, 49.5; H, 3.1; N, 11.3; C$_{15}$H$_{11}$N$_3$O$_2$BrF Requires C, 49.5; H, 3.0; N, 11.5%.

EXAMPLE 49

Methanesulphonyl chloride (32 mg, 0.275 mmol) was added dropwise to a mixture of 4-4-bromo-2-fluoroanilino)-6-methoxy-7-(3-metlylaminopropoxy)quinazoline (109 mg, 0.25 mmol) and triethylamine (30 mg, 0.3 mmol) in methylene chloride (3 ml) cooled at 0° C. The solution was stirred for 2 hours at 0° C. and the volatiles were removed by evaporation. The residue was partitioned between ethyl acetate and water, the organic layer was separated, washed with brine, dried (MgSO$_4$ and the solvent removed by evaporation. The solid was triturated with ether and collected by filtration. The solid was dissolved in methylene chloride containing methanol (0.5 ml) and 3M hydrogen chloride in ethyl acetate (0.3 ml) was added. The suspension was diluted with ethyl acetate and concentrated by evaporation. The resulting solid product was collected by filtration,-washed with ether and dried under vacuum to give 4-(4-bromo-2-fluoroanilino)-6-methoxy-(3([N-methyl-N-methylsulphonyl]amino)propoxy)quinazoline hydrochloride (85 mg, 61%).

$^1$H NMR Spectrum: (DMSOd$_6$; CF$_3$COOD) 2.1–2.2(m, 2H); 2.82(s, 3H); 2.89(s, 3H); 3.29(t, 2H); 4.02(s, 3H); 4.27(t, 2H); 7.35(s, 1H); 7.55–7.65(m, 2H); 7.79(d, 1H); 8.12(s, 1H); 8.88(s, 1H); MS-(EI): 512 [M.]$^+$; Elemental analysis: Found C, 43.5; H, 4.2; N, 10.0; C$_{20}$H$_{22}$N$_4$O$_4$BrFS0.6H$_2$O 0.75HCl Requires C, 43.5; H, 4.4; N, 10.2%.

The starting material was prepared as follows:

Diethyl azodicarboxylate (522 mg, 3 mmol) was added dropwise to a suspension of 4-(4-bromo-2-fluoroanilino)-7-hydroxy-6-methoxyquinazoline (364 mg, 1 mmol), (prepared as described for the starting material in Example 48), triphenylphosphine (786 mg, 3 mmol) and 3-methylamino-1-propanol (178 mg, 2 mmol), (J.Am.Chem.Soc., 1954, 76, 2789), in methylene chloride (4 ml) under nitrogen. The mixture was stirred for 1 hour at ambient temperature, neutral alumina (~20 g) was added to the reaction mixture and the solvent was removed by evaporation. The powder was poured onto a column of neutral alumina and was eluted with a mixture of methylene chloride/methanol (95/5 followed by 90/10 and 80/20). The purified product was triturated with ether, collected by filtration, washed with ether and dried under vacuum to give 4-(4-bromo-2-fluoroanilino)-6-methoxy-7-(3-methylaminopropoxy)quinazoline (220 mg, 50%).

EXAMPLE 50

A solution of diethyl azodicarboxylate (209 mg, 1.2 mmol) in methylene chloride (1 ml) and then (S)-1-3-hydroxypropyl)-pyrrolidine-2-carboxamide (97 mg, 0.56 mmol) was added dropwise to a suspension of 4-(4-bromo-2-fluoroanilino)-7-hydroxy-6-methoxyquinazoline (146 mg, 0.4 mmol), (prepared as described for the starting material in Example 48), and triphenylphosphine (314 mg, 1.2 mmol) in methylene chloride (4 ml) under nitrogen. The mixture was stirred for 1 hour at ambient temperature and further triphenylphosphine (109 mg, 0.4 mmol) and (S)-1-(3-hydroxypropyl)-pyrrolidine-2-carboxamide (40 mg, 0.23 mmol) were added followed by the dropwise addition of diethyl azodicarboxylate (70 mg, 0.4 mmol). The mixture was stirred for 30 minutes at ambient temperature and further (S)-1-(3-hydroxypropyl)-pyrrolidine-2-carboxamide (34 mg, 0.2 mmol) was added. The mixture was then stirred for 2 hours at ambient temperature and the mixture was purified by pouring directly onto a column of silica and eluting with methylene chloride/ethyl acetate/methanol (60/35/5). The purified product was triturated with ether, collected by filtration, washed with ether and dried under vacuum. The solid was dissolved in methylene chloride and 3M hydrogen chloride in ethyl acetate (0.4 ml) was added. The resulting precipitate was collected by filtration, washed with ethyl acetate and dried under vacuum to give (S)-4-(4-bromo-2-fluoroanilino)-7-(3-(2-carbamoylpyrrolidin-1-yl) propoxy)-6-methoxyquinazoline hydrochloride (110 mg, 47%).

$^1$H NMR Spectrum: (DMSOd$_6$; CF$_3$COOD; 60° C.) 1.9–2.0(m, 2H); 2.0–2.1(m, 2H); 2.15–2.25(m, 2H); 3.2–3.3 (m, 1H); 3.3–3.5(m, 2H); 3.7–3.8(m, 1H); 4.02(s, 3H); 4.15–4.2(m, 1H); 4.3–4.4(m, 2H); 7.4(s, 1H); 7.5–7.6(m, 2H); 7.75(d, 1H); 8.2(s, 1H); 8.83(s, 1H); MS-(EI): 518 [M.]$^+$; Elemental analysis: Found C, 46.0; H, 4.9; N, 11.2; C$_{23}$H$_{25}$N$_5$O$_3$BrF 0.8H$_2$O 1.9HCl Requires C, 45.9; H, 4.8; N, 11.6%.

The starting material was prepared as follows:

3-Bromo-1-propanol (584 mg, 4.2mmol) was added to a mixture of (S)-pyrrolidine-2-carboxamide (399 mg, 3.5 mmol) and potassium carbonate (966 mg, 7 mmol) in acetonitrile (10 ml). The mixture was heated at reflux for 5 hours and the mixture was stirred for 18 hours at ambient temperature. The insolubles were removed by filtration and the solvent was removed from the filtrate by evaporation The residue was purified by column chromatography on silica eluting with methylene chloride/methanol (9/1 followed by 8/2) to give (S)-1-(3-hydroxypropyl)-pyrrolidine-2-carboxamide (365 mg, 60%).

MS-(EI): 173 [M.]$^+$.

EXAMPLE 51

Methoxyacetyl chloride (34 mg, 0.31 mmol) was added to a solution of 4-(4-chloro-2-fluoroanilino)-6-methoxy-7-(2-methylaminoethoxy)quinazoline (113 mg, 0.3 mmol), (prepared as described for the starting material in Example 60), and triethylamine (33 mg, 0.33 mmol) in methylene chloride (3 ml). The mixture was stirred for 18 hours at ambient temperature and was then partitioned between ethyl acetate and brine. The organic layer was separated, dried (MgSO$_4$) and the solvent removed by evaporation. The residue was purified by chromatography on silica eluting with methylene chloride/acetonitrile/methanol (6/3/1). The purified solid product was triturated with methylene chloride and ether, collected by filtration, washed with ether and dried under vacuum. The solid was dissolved in a mixture of methylene chloride/methanol (1/1) and 2M hydrogen chloride in ethyl acetate (0.5 ml) was added. The mixture was diluted with ether and and the resulting precipitate was collected by filtration, washed with ether and dried under vacuum to give 4-(4-chloro-2-fluoroanilino)-6-methoxy-7-(2-([methyl-N-methoxyacetyl]amino)ethoxy)quinazoline hydrochloride (62 mg, 42%).

$^1$H NMR Spectrum: (DMSOd$_6$; CF$_3$COOD; 80° C.) 2.9–3.2(br s, 3H); 3.35(s, 3H); 3.8–3.9(br s, 2H); 4.05(s, 3H); 4.0–4.3(m, 2H); 4.4(t, 2H); 7.4(s, 1H); 7.45(d, 1H); 7.6–7.7(m, 2H); 8.1(s, 1H); 8.8(s, 1H); MS-ESI: 449 [MH]$^+$; Elemental analysis: Found C, 48.8; H, 4.6; N, 10.7; C$_{21}$H$_{22}$N$_4$O$_4$ClF 0.9H2O 1.35HCl Requires C, 49.0; H, 4.9; N, 10.9%.

EXAMPLE 52

Diethyl azodicarboxylate (400 mg, 2.3 mmol) was added dropwise to a mixture of 4-(4-chloro-2-fluoroanilino)-7-hydroxy-6-methoxyquinazoline (250 mg, 0.78 mmol), (prepared as described for the starting material in Example 2), triphenylphosphine (615 mg, 2.3 mmol) and 4-(2-hydroxyethyl)-3-morpholinone (170 mg, 1.17 mmol), (EP 580402A2), in methylene chloride (5 ml) under nitrogen. The mixture was stirred for 4 hours at ambient temperature, methylene chloride (5 ml) was added and stirring was continued for a further 18 hours at ambient temperature. THF (5 ml). 4-(2-hydroxyethyl)-3-morpholinone (113 mg, 0.78 mmol). triphenylphosphine (204 mg, 0.78 mmol) were added and diethyl azodicarboxylate (136 mg, 0.78 mmol) was then added dropwise. The mixture was stirred for 5 minutes at ambient temperature, and was purified by pouring directly onto a silica column, eluting with methylene chloride/ethyl acetate/methanol (5/4/1). The purified solid was dissolved in methylene chloride and 2M methanolic hydrogen chloride (0.5 ml) was added. The mixture was concentrated by evaporation and then diluted with ether. The resulting precipitate was collected by filtration, washed with ether and dried under vacuum to give 4-(4-chloro-2-fluoroanilino)-6-methoxy-7-(2-(3-oxomorpholino)ethoxy) quinazoline hydrochloride (150 mg, 39%).

$^1$H NMR Spectrum: (DMSOd$_6$; CF$_3$COOD) 3.6(t, 2H); 3.8–3.9(m, 4H); 4.05(s, 3H); 4.1(s, 3H); 4.4(t, 2H); 7.3(s, 1H); 7.45(d. 1H); 7.65(t, 1H); 7.7(d, 1H); 8.1(s, 1H); 8.9(s, 1H); MS-ESI: 469 [MNa]$^+$; Elemental analysis: Found C, 51.6; H, 4.4; N, 11.8; C$_{21}$H$_{20}$N$_4$O$_4$ClF 0.35H$_2$O 0.95HCl Requires C, 51.7; H, 4.5; N, 11.5%.

EXAMPLE 53

Diethyl azodicarboxylate (209 mg, 1.2 mmol) was added dropwise to a mixture of 4-(4-chloro-2-fluoroanilino)-7-hydroxy-6 methoxyquinazoline (128 mg, 0.4 mmol), (prepared as described for the starting material in Example 2), triphenylphosphine (314 mg, 1.2 mmol) and 2-(2-morpholinoethoxy)ethanol (97 mg, 0.56 mmol) in methylene chloride (4 ml) under nitrogen. The mixture was stirs for 1 hour at ambient temperature, triphenylphosphine (105 mg, 0.4 mmol), 2-(2-morpholinoethoxy)ethanol (49 mg, 0.28 mmol) and diethyl azodicarboxylate (70 mg, 0.4 mmol) were added. The mixture was stirred for 1 hour at ambient temperature and was purified by pouring directly onto a silica column eluting with methylene chloride/acetonitrile/methanol (6/3/1). The purified product was triturated with ether, collected by filtration and dissolved in methylene chloride. 2M Ethereal hydrogen chloride (0.5 ml) was added and the resulting precipitate was collected by filtration, washed with ether and dried under vacuum to give 4-(4-chloro-2-fluoroanilino)-6-methoxy-7-(2-(2-morpholinoethoxy)ethoxy)quinazoline hydrochloride (100 mg, 45%).

$^1$H NMR Spectrum: (DMSOd$_6$; CF$_3$COOD) 3.1–3.2(m, 2H); 3.3–3.5(m, 5H); 3.7–3.8(m, 2H); 3.9–4.0(m, 5H); 4.02(s, 3H); 4.4(br s, 2H); 7.46(s, 1H); 7.48(d, 1H); 7.6(t, 1H); 7.7(d, 1H); 8.25(s, 1H); 8.89(s, 1H); MS-ESI: 477 [MH]$^+$; Elemental analysis: Found C, 48.8; H, 5.6; N, 9.9; C$_{23}$H$_{26}$N$_4$O$_4$ClF 1H$_2$O 1.95HCl Requires C, 48.8; H, 5.3; N, 9.9%.

The starting material was prepared as follows:

2-(2-Chloroethoxy)ethanol (1.25 g, 10 mmol) was added to a mixture of morpholine (2.58 g, 30 mmol) and potassium carbonate (5.5 g, 40 mmol) in acetonitrile (50 ml). The mixture was heated at reflux for 6 hours and then stirred for 18 hours at ambient temperature. The insolubles were removed by filtration and the volatiles were removed from the filtrate by evaporation. The residue was purified by column chromatography eluting with methylene chloride/methanol (95/5 followed by 90/10 and then 80/20) to give 2-(2-morpholinoethoxy)ethanol (600 mg, 34%).

$^1$H NMR Spectrum: (CDCl$_3$) 2.5(br s, 4H); 2.59(t, 2H); 3.6–3.85(m, 10H); MS-(EI): 175 [M.]$^+$.

EXAMPLE 54

Diethyl azodicarboxylate (209 mg, 1.2 mmol) was added dropwise to a mixture of 4-(4-chloro-2-fluoroanilino)-7-hydroxy-methoxyquinazoline (128 mg, 0.4 mmol), (prepared as described for the starting material in Example 2), triphenylphosphine (314 mg, 1.2 mmol) and (S)-1-(3-hydroxypropyl)-pyrrolidine-2-carboxamide (97 mg, 0.56 mmol), (prepared as described for the starting material in Example 50), in methylene chloride (4 ml). The mixture was stirred for 2 hours at ambient temperature, and further triphenylphosphine (105 mg, 0.4 mmol) and (S-1-(3-hydroxypropyl)pyrrolidine-2-carboxamide (49 mg, 0.28 mmol) were added followed by the dropwise addition of diethyl azodicarboxylate (70 mg, 0.4 mmol). The mixture was stirred for 1 hour at ambient temperature, and was purified by pouring directly onto a silica column eluting with methylene chloride/acetonitrile/methanol (6/3/1 followed by 60/25/15). The purified oil was triturated with ether, collected by filtration, washed with ether and dried under vacuum. The solid was dissolved in methylene chloride and 2M ethereal hydrogen chloride (0.5 ml) was added. The mixture was diluted with ether and the resulting precipitate was collected by filtration, washed with ether and dried under vacuum to give (S)-7-(3-(2-carbamoylpyrrolidin-1-yl)propoxy)-4-(4-chloro-2-fluoroanilino)-6-methoxyquinazoline hydrochloride (70 mg, 32%).

$^1$H NMR Spectrum: (DMSOd$_6$; CF$_3$COOD) 1.8–2.0(m, 2H); 2.05–2.15(m, 2H); 2.2–2.3(m, 2H); 3.1–3.5(m, 2H); 3.7–3.8(m, 1H); 4.02(s, 3H); 4.0–54.2(m, 2H); 4.3(m, 2H); 7.04(s, 1H); 7.45(d, 1H); 7.65(t, 1H); 7.7(d, 1H); 8.22(s, 1H); 8.88(s, 1H); MS-ESI: 474 [MH]$^+$; Elemental analysis: Found C, 49.4; H, 12.4; N, 5.3; C$_{23}$H$_{25}$N$_5$O$_3$ClF 1.5H$_2$O 1.55HCl Requires C, 49.5; H, 12.6; N, 5.3%.

EXAMPLE 55

Diethyl azodicarboxylate (209 mg, 1 mmol) was added dropwise to a mixture of 4-(4-chloro-2-fluoroanilino)-7-hydroxy-6-methoxyquinazoline (128 mg, 0.4 mmol), (prepared as described for the starting material in Example 2), cis-3-(2,6-dimethylmorpholino)-1-propanol (97 mg, 0.56 mmol) and triphenylphosphine (314 mg, 1.2 mmol) in methylene chloride (4 ml) under nitrogen. The mixture was stirred for 1 hour at ambient temperature and the solvent was removed by evaporation. The residue was purified by column chromatography eluting with methylene chloride/methanol (95/5 followed by 90/10). The purified product was dissolved in methylene chloride and 2M ethereal hydrogen chloride (1 ml) was added. The solution was diluted with ether and left to stand. The resulting precipitate was collected by filtration, washed with ether and dried under vacuum to give 4-(4-chloro-2-fluoroanilino)-7-(3-(2,6dimethylmorpholino)propoxy)-6-methoxyquinazoline hydrochloride (130 mg, 590%).

$^1$H NMR Spectrum: (DMSOd$_6$; CF$_3$COOD) 1.17(d, 6H); 2.3–2.4(m, 2H); 2.7(t, 2H); 3.25–3.35(m, 2H); 3.55(d, 2H); 3.9–4.0(m, 2H); 4.03(s, 3H); 4.35(t, 2H); 7.43(s, 1H); 7.45 (d, 1H); 7.63(t, 1H); 7.70(d, 1H); 8.25(s, 1H); 8.88(s, 1H); MS-ESI: 475 [MH]$^+$; Elemental analysis: Found C, 51.7; H, 6.0; N, 9.7; C$_{24}$H$_{26}$N$_4$O$_3$ClF 0.6H$_2$O 1.95HCl Requires C, 51.8; H, 5.6; N, 10.0%.

The starting material was prepared as follows:

3-Chloro-1-propanol (1.04 g, 11 mmol) followed by potassium carbonate (2.07 g, 15 mmol) was added to a solution of 2,6-dimethylmorpholino (1.15 g, 10 mmol), (supplied by Aldrich Chemical Company Limited as a mixture of isomers), in acetonitrile (15 ml). The mixture was heated at reflux overnight and allowed to cool, the insolubles were removed by filtration and the volatiles were removed from the filtrate by evaporation. The residue was purified by column chromatography on silica eluting with methylene chloride/acetonitrile/methanol (60/35/5 followed by 60/30/10) to give cis-3-(2,6-dimethylmorpholino)-1-propanol (500 mg).

$^1$H NMR Spectrum: (CDCl$_3$) 1.16(d, 6H); 1.7–1.8(m, 4H); 2.61(t, 2H); 2.91(d, 2H); 3.6–37 (m, 2H); 3.81(t, 2H); MS-ESI: 173 [M.]$^+$.

EXAMPLE 56

A solution of 4-(4-chloro-2-fluoroanilino)-6-methoxy-7-(trifluoromethylsulphonyloxy)quinazoline (180 mg, 0.4 mmol), (prepared as described for the starting material in Example 11), in anhydrous THF (2 ml) and benzene (2 ml) was purged of oxygen and placed under nitrogen. Tetrakis (triphenylphosphine)palladium(0) (23 mg, 0.02 mmol) followed by a solution of sodium triisopropylsilylthiolate (102 mg, 0.48 mmol), (Tetrahedron Lett. 1994, 35, 3221), in THF (2 ml) was added and the mixture was heated at reflux for 2 hours The mixture was allowed to cool to ambient temperature and 4-(3-chloropropyl)morpholine (98 mg, 0.6 mmol), (J. Am. Chem. Soc. 1945,67,736), DMF (2 ml) and tetrabutylammonium fluoride,(0.5 ml of a 1M solution in THF, 0.5 mmol) were added sequentially. The mixture was stirred for 1 hour at ambient temperature, the volatiles were removed by evaporation and the residue was partitioned between ethyl acetate and water. The organic layer was ed, washed with brine, dried (MgSO$_4$) and the solvent removed by evaporation. The residue was purified on neutral alumina eluting with methylene chloride/acetone (90/10 followed by 80/20). The purified product was triturated in a mixture of ether and hexane, collected by filtration, washed with ether and dried under vacuum to give 4-(4-chloro-2-fluoroanilino)-6-methoxy-7-(3-morpholinopropylthio) quinazoline hydrochloride (65 mg, 30%).

$^1$H NMR Spectrum: (DMSOd$_6$; CF$_3$COOD) 2.1–2.2(m, 2H); 3.1–3.2(m, 2H); 3.22(t, 2H); 3.3–3.4(m, 2H); 3.47(d, 2H); 3.74(t, 2H); 4.0(d, 2H); 4.08(s, 3H); 7.48(d, 1H); 7.64(t, 2H; 7.68(d, 1H); 7.86(s, 1H); 8.19(s, 1H); 8.91(s, 1H); MS-ESI: 463 [MH]$^+$; Elemental analysis: Found C, 47.6; H, 5.16; N, 47.6; C$_{22}$H$_{24}$N$_4$O$_2$ClFS 1.2H$_2$O 1.85HCl Requires C, 47.8; H, 5.16; N, 47.8%.

EXAMPLE 57

3-Chloroperbenzoic acid (188 mg, 1.05 mmol) was added in portions to a solution of 4-(4-chloro-2-fluoroanilino)-6-methoxy-7-(2-methoxyethylthio)quinazoline (275 mg, 0.7 mmol), (prepared as described in Example 11), in methylene chloride (6 ml). The mixture was stirred for 30 minutes at ambient temperature, diluted with methylene chloride (20 ml), washed with aqueous sodium hydrogen carbonate solution and then brine, dried (MgSO$_4$) and the solvent removed by evaporation. The residue was purified by column chromatography eluting with methylene chloride/acetone (8/2 followed by 7/3 and 6/4). The purified product was dissolved in methylene chloride and 3M ethereal hydrogen chloride (0.5 ml) was added. The mixture was diluted with ether and the resulting precipitate was collected by filtration, washed with ether and dried under vacuum to give 4-(4-chloro-2-fluoroanilino)-6-methoxy-7-(2-methoyethylsulphinyl)quinazoline hydrochloride (110 mg 38%).

$^1$H NMR Spectrum: (DMSOd$_6$; CF$_3$COOD) 3.05(td, 1H); 3.24(s, 3H); 3.5–3.6(m, 1H); 3.7–3.8(m, 2H); 4.1(s, 3H); 7.5(d, 1H); 7.65(t, 1H); 7.75(d, 1H); 8.2(s, 1H); 8.4(s,1H); 9.0(s, 1H); MS-ESI: 410 [MH]$^+$; Elemental analysis: Found C, 47.9; H, 4.2; N, 9.3; C$_{18}$H$_{17}$N$_3$O$_3$ClFS 0.5H$_2$O 0.85HCl Requires C, 48.0; H, 4.2; N, 9.3%.

EXAMPLE 58

Diethyl azodicarboxylate (218 mg, 1.25 mmol) was added dropwise to a solution of 4-(4-chloro-2-fluoroanilino)-7-hydroxy-6-methoxyquinazoline (159 mg, 0.5 mmol), (prepared as described for the starting material in Example 2), 4-hydroxy-1-methylpiperidine (115 mg, 1 mmol) and triphenylphosphine (328 mg, 1.25mmol) in methylene chloride (5 ml) cooled at 5° C. under nitrogen. The mixture was stirred for 1 hour at ambient temperature, the solvent was removed by evaporation and the residue was partitioned between 2M hydrochloric acid and ether. The aqueous layer was separated, adjusted to pH9 with aqueous sodium hydrogen carbonate solution and extracted with methylene chloride. The methylene chloride layer was washed with brine, dried (MgSO$_4$) and the solvent removed by evaporation. The residue was purified on neutral alumina eluting with methylene chloride/methanol (97/3). The purified product was triturated with ether, collected by filtration and dried to give 4-(4-chloro-2-fluoroanilino)-6-methoxy-7-(1-methylpiperidine-4-yloxy)quinazoline (180 mg, 79%).

$^1$H NMR Spectrum: (DMSOd$_6$; CF$_3$COOD) 1.9–2.0(m, 1H); 2.05–2.15(m, 2H); 2.35–2.45(m, 1H); 2.85 and 2.90 (2s, 3H); 3.05–3.25(m, 2H); 3.45(m, 1H); 3.6(d, 1H); 4.1 and 4.12(2s, 3H); 4.8–4.9(m, 0.5 H); 5–5.05(m, 0.5H); 7.4–7.7(m, 4H); 8.2(d, 1H); 8.9(s, 1H); MS-ESI: 417 [MH]$^+$.

EXAMPLE 59

Methanesulphonyl chloride (35 μl, 0.46 mmol) was added dropwise to a solution of 4-(4-chloro-2-fluoro)-6-methoxy-7-(3-methyl aminopropoxy)quinazoline (170 mg, 043 mmol) and triethylamine (67 μl, 0.48 mmol) in methylene chloride (3 ml). The mixture was stirred for 5 hours at ambient temperature, the volatiles was removed by evaporation and the residue was partitioned between ethyl acetate and water. The organic layer was separated, washed with water and then brine, dried (MgSO$_4$) and the solvent removed by evaporation. The residue was purified by column chromatography on silica eluting with methylene chloride/acetonitrile/methanol (70/28/2). The purified product was dissolved in a mixture of methylene chloride/methanol (1/1) and 2M ethereal hydrogen chloride (1 ml) was added. The volatiles were removed by evaporation and the residue was triturated with ether, collected by filtration, washed with ether and dried under vacuum to give 4-(4-chloro-2-fluoroanilino)-6-methoxy-7-(3-([N-methyl-N-methylsulphonyl]amino)propoxy)quinazoline hydrochloride (133 mg, 61%/).

$^1$H NMR Spectrum: (DMSOd$_6$; CF$_3$COOD) 2.1–2.2(m, 2H); 2.82(s, 3H); 2.89(s, 3H); 3.3(t, 2H); 4.02(s, 3H); 4.27(t, 2H); 736(s, 1H); 7.46(d, 1H); 7.6–7.7(m, 2H); 8.14(s, 1H); 8.88(s, 1H); MS-ESI: 469 [MH]$^+$; Elemental analysis: Found C, 48.1; H, 4.7; N, 10.8; C$_{20}$H$_{22}$N$_4$O$_4$ClFS 0.9HCl Requires C, 47.9; H, 4.6; N, 11.2%.

The staring material was prepared as follows:

A solution of di-tert-butyl dicarbonate (4.9 g, 22 mmol) in THF (12 ml) was added dropwise to a solution of 3-methylamino-1-propanol (2 g, 22 mmol), (J.Am.Chem.Soc., 1954, 76,2789), in a mixture of THF (12 ml) and water (12 ml). The mixture was stirred for 18 hours at ambient temperature, the THF was removed by evaporation. The aqueous residue was extracted with ether. The extracts were combined, washed with 0.1M hydrochloric acid, and then brine, dried (MgSO$_4$ and the solvent removed by evaporation to give 3-([N-(tert-butylcarbonyl)-N-methyl]amino)-1-propanol (3.95 g, 95%).

$^1$H NMR Spectrum: (CDCl$_3$) 1.46(s, 9H); 1.6–1.8(m, 2H); 2.83(s, 3H); 3.3–3.4(br s, 2H); 3.5–3.6(br s, 2H); MS-(EI): 190 [MH]$^+$.

Diethyl azodicarboxylate (2.4 ml, 15 mmol) was added dropwise to a solution of 3-([N-(tert-butylcarbonyl)-N-methyl]amino)-1-propanol (1.77 g, 9.4 mmol), 4-(4-chloro-2-fluoroanilino)-7-hydroxy-6-methoxyquinazoline (2 g, 6.26 mmol), (prepared as described for the starting material in Example 2), and triphenylphosphine (4.1 g, 15 mmol) in methylene chloride (50 ml) under nitrogen. The mixture was stirred for 1 hour at ambient temperature, and further 3-([N-(tert-butylcarbonyl)-N-methyl]amino)-1-propanol (236 mg, 1.2 mmol), triphenylphosphine (820 mg, 3.1 mmol) and diethyl azodicarboxylate (492 μl, 3.1 mmol) were added. The solution was stirred for 1 hour at ambient temperature and concentrated by evaporation. The residue was purified on column chromatography eluting with acetonitrile. The purified product was triturated with ether, collected by filtration and repurified by column chromatography eluting with methylene chloride/methanol (97/3) to give 7-3-([N-(tert-butylcarbonyl)-N-methyl]amino)propoxy)-4-(4-chloro-2-fluoroanilino)-6-methoxyquinazoline (2.2 g, 72%).

$^1$H NMR Spectrum: (DMSOd$_6$; CF$_3$COOD) 1.3(s, 9H); 2.0–2.1(m, 2H); 2.8–2.9(br s, 3H); 3.4–3.5(m, 2H); 4.0(s, 3H); 4.25(t, 2H); 7.3(s, 1H); 7.45(d, 1H); 7.6–7.7(m, 2H); 8.08(s, 1H); 8.88(s, 1H); MS-(EI): 491 [MH]$^+$; Elemental analysis: Found C, 58.6; H, 5.8; N, 11.3; C$_{24}$H$_{28}$N$_4$O$_4$ClF Requires C, 58.7; H, 5.7; N, 11.4%.

A solution of 7-(3-([N-(tert-butylcarbonyl)-N-methyl]amino)propoxy)-4-(4-chloro-2-fluoroanilino)-6-methoxyquinazoline (2.1 g, 4.3 mmol) in a mixture of methylene chloride (6 ml) and TFA (5 ml) was stirred at ambient temperature for 1 hour. Toluene was added and the volatiles were removed by evaporation. The residue was dissolved in water and the solution was adjusted to pH7–8 with saturated aqueous sodium hydrogen carbonate solution. The resulting precipitate was separated by centrifugation and decanting the filtrate and the solid product was thoroughly washed with water. The solid was recrystallised from methylene chloride/methanol, the product collected by filtration, washed with water, and then ether and dried under vacuum over phosphorus pentoxide to give 4-(4-chloro-2-fluoroanilino)methoxy-7-(3-methylaminopropoxy)quinazoline (1,4 g, 83%).

$^1$H NMR Spectrum: (DMSOd$_6$; CF$_3$COOD) 2.2–2.3(m, 2H); 2.65(s, 3H); 3.1–3.2(m, 2H); 4.05(s, 3H); 4.32(t, 2H); 7.37(s, 1H); 7.48(d, 1H); 7.64(t, 1H); 7.67(d, 1H); 8.11(s, 1H); 8.9(s, 1H); MS-(EI): 391 [MH]$^+$.

EXAMPLE 60

Triethylamine (44 μl, 0.32 mmol) and then a solution of 2-bromoethyl methyl ether (40 mg, 0.29 mmol) in acetone (0.5 ml) was added dropwise to a solution of 4-(4-chloro-2-fluoroanilino)-6-methoxy-7-(2-methylaminoethoxy)

quinazoline (100 mg, 0.26 mmol) in acetone (2.5 ml) heated at 50° C. under nitrogen. The mixture was stirred for 7 hours at 50° C., the mixture was allowed to cool and partitioned between ethyl acetate and water. The organic layer was separated, washed with brine, dried ($MgSO_4$) and the volatiles removed by evaporation. The residue was purified by column chromatography eluting with methylene chloride/methanol (92/8). The purified product was dissolved in methylene chloride, insolubles were removed by filtration and 2.2M ethereal hydrogen chloride (0.5 ml) was added to the filtrate. The volatiles were removed by evaporation and the residue was triturated with ether, collected by filtration and dried under vacuum to give 4-(4-chloro-2-fluoroanilino)-6-methoxy-7-(2-([N-(2-methoxyethyl)-N-methyl]amino)ethoxy)quinazoline hydrochloride (22 mg, 16%).

$^1$H NMR Spectrum: ($DMSOd_6$; $CF_3COOD$) 3.0(s, 3H); 3.35(s, 3H); 3.4–3.6(m, 2H); 3.65–3.85(m, 4H); 4.03(s, 3H); 4.64(t, 2H); 7.45(s, 1H); 7.47(d, 1H); 7.63(t, 1H); 7.69(d, 1H); 8.23(s, 1H); 8.9(s, 1H); MS-ESI: 435 [MH]$^+$; Elemental analysis: Found C, 48.9; H, 5.3; N, 10.4; $C_{21}H_{24}N_4O_3ClF$ 0.8$H_2O$ 1.85HCl Requires C, 48.8; H, 5.3; N, 10.8%.

The starting material was prepared as follows:

Diethyl azodicarboxylate (3.13 g, 24 mmol) was added dropwise to a suspension of 4-(4-chloro-2-fluoroanilino)-7-hydroxy-6-methoxyquinazoline (2.56 mg, 8 mmol), (prepared as described for the starting material in Example 2), 2-[(N-(tert-butylcarbonyl)-N-methyl]amino)ethanol (2.1 g, 1.2 mmol), (Synth. Commun. 1993, 23, 2443), and triphenylphosphine (63 g, 24 mmol) in methylene chloride (50 ml) under nitrogen. The mixture was stirred for 1.5 hours at ambient temperature and further 2-[(N-(tert-butylcarbonyl)-N-methyl]amino)ethanol (0.21 g, 1.2 mmol), triphenylphosphine (630 mg, 2.4 mmol) and diethyl azodicarboxylate (0.31 g, 2.4 mmol) were added. The mixture was stirred for 1 hour, the mixture was purified by pouring it directly onto a silica column and eluting with methylene chloride/ether/methanol (60/30/10) to give 7-(2-([N-(tert-butylcarbonyl)-N-methyl]amino)ethoxy)-4-(4-chloro-2-fluoroanilino)-6-methoxyquinazoline (3.8 g, 99%).

A solution of 7-(2-([N-(tert-butylcarbonyl)-N-methyl]amino)ethoxy)-4-(4-chloro-2-fluoroanilino)-6-methoxyquinazoline (2.38 g, 5 mmol) in methylene chloride (5 ml) and TFA (10 ml) was stirred at ambient temperature for 1 hour. Toluene was added and the volatiles were removed by evaporation. The residue was partitioned between 2M hydrochloric acid and ethyl acetate. The aqueous layer was adjusted to pH8 with sodium hydrogen carbonate and extracted with ethyl acetate. The organic extracts were combined, washed with brine, dried ($MgSO_4$) and the solvent removed by evaporation to give 4-(4-chloro-2-fluoroanilino)-6-methoxy-7-(2-methylaminoethoxy)quinazoline (700 mg, 37%).

$^1$H NMR Spectrum: ($DMSOd_6$; $CF_3COOD$) 2.75(s, 3H); 3.5–3.6(m, 2H); 4.05(s, 3H); 4.5(t, 2H); 7.4(s, 1H); 7.4–7.5 (m, 1H); 7.65(t, 1H); 7.7(d, 1H); 8.15(s, 1H); 8.8(s, 1H).

EXAMPLE 61

Dimethylcarbamyl chloride (38 μl, 0.42 mmol) was added to a solution of 4-(4-chloro-2-fluoroanilino)-6-methoxy-7-(2-methylaminoethoxy)quinazoline (150 mg, 0.4 mmol), (prepared as described for the starting material in Example 60), and triethylamine (61 μl, 0.44 mmol) in methylene chloride (4 ml). The mixture was stirred for 2.5 hours at ambient temperature, the resulting precipitate was collected by filtration and washed with ether. The solid was purified by column chromatography, eluting with methylene chloride/methanol (92/8). The purified product was dissolved in methylene chloride/methanol (1/1), 2.9M ethereal hydrogen chloride (1 ml) was added and the volatiles were removed by evaporation. The residue was triturated with ether and the solid product collected by filtration, washed with ether and dried under vacuum to give 4-(4-chloro-2-fluoroanilino)-6-methoxy-7-(2-N',N',N'-trimethylureido)ethoxy)quinazoline hydrochloride (80 mg, 41%).

$^1$H NMR Spectrum: ($DMSOd_6$; $CF_3COOD$) 2.73(s, 6H); 2.91(s, 3H); 3.59(t, 2H); 4.0(s, 3H); 4.34(t, 2H); 7.36(s, 1H); 7.5(d, 1H); 7.63(t, 1H); 7.68(d, 1H); 8.1(s, 1H); 8.9(s, 1H); MS-(EI): 447 [M.]$^+$; Elemental analysis: Found C, 51.2; H, 5.1; N, 13.9; $C_{21}H_{23}N_5O_3ClF$ 0.5$H_2O$ 1HCl Requires C, 51.1; H, 5.1; N, 14.2%.

EXAMPLE 62

7-(2-Bromoethoxy)-4-(4-chloro-2-fluoroanilino)-6-methoxyquinazoline (150 mg, 0.35 mmol) and 1-acetylpiperazine (135 mg, 1 mmol) were heated together at 140° C. for 10 minutes. The mixture was allowed to cool and was dissolved in a mixture of methylene chloride/ethyl acetate. The solution was washed with water, and then brine, dried ($MgSO_4$) and the solvent removed by evaporation. The residue was purified by column chromatography eluting with methylene chloride/methanol (9/1). The purified product was dissolved in methylene chloride and 2.9M ethereal hydrogen chloride was added. The precipitate was collected by filtration, washed with ether and dried under vacuum to give 7-(2-(4-acetylpiperazin-1-yl)ethoxy)-4-(4-chloro-2-fluoroanilino)-6-methoxyquinazoline hydrochloride (152 mg, 79%).

$^1$H NMR Spectrum: ($DMSOd_6$; $CF_3COOD$; 50° C.) 2.07 (s, 3H); 3.3–3.7(br s, 8H); 3.75(t, 2H); 4.05(s, 3H); 4.65(t, 2H); 7.45(br s, 2H); 7.6–7.7(m, 2H); 8.15(s, 1H); 8.9(s, 1H); MS-(EI): 473 [M.]$^+$; Elemental analysis: Found C, 49.8; H, 5.0; N, 12.5; $C_{23}H_{25}N_5O_3ClF$ 0.5$H_2O$ 1.9HCl Requires C, 50.0; H, 5.1; N, 12.7%.

The starting material was prepared as follows:

1,2-Dibromoethane (5.4 ml, 62 mmol) was added to a mixture of 4-(4-chloro-2-fluoroanilino)-7-hydroxy-6-methoxyquinazoline (5 g, 15.6 mmol), (prepared as described for the starting material in Example 2), and potassium carbonate (8.6 g, 62 mmol) in DMF (50 ml) and the mixture stirred for 18 hours at ambient temperature. Water was added and the resulting precipitate was collected by filtration. The solid was purified by chromatography on neutral alumina eluting with methylene chloride/methanol (95/5). The semi-purified product was repurified by chromatography on silica eluting with methylene chloride/methanol (97/3). The purified product was triturated with ether, collected by filtration, washed with ether and dried under vacuum to give 7-(2-bromoethoxy)-4-(4-chloro-2-fluoroanilino)-6-methoxyquinazoline (3.58 g, 54%).

$^1$H NMR Spectrum: ($DMSOd_6$) 3.28(s, 3H); 3.96(s, 3H); 4.48(t, 2H); 4.85(t, 2H); 7.21(s, 1H); 7.34(d, 1H); 7.5–7.6 (m, 2H); 7.80(s, 1H); 8.36(s, 1H); 9.55(s, 1H).

EXAMPLE 63

A mixture of 7-(2-(2-bromoethoxy)ethoxy)-4-(4-chloro-2-fluoroanilino)-6-methoxyquinazoline (150 mg, 0.32 mmol) in 1-methylpiperazine (2 ml) was heated at 100° C. for 1 hour. The mixture was allowed to cool and was partitioned between ethyl acetate and water. The organic layer was separated and washed with water and then brine, dried (MgSO$_4$) and the solvent removed by evaporation. The residue was purified by column chromatography on silica eluting with methylene chloride/methanol (85/15 followed by 80/20). The purified solid product was dissolved in methylene chloride/methanol (1/1) and 2.9M ethereal hydrogen chloride was added. The volatiles were removed by evaporation and the solid was triturated with ether, collected by filtration, washed with ether and dried under vacuum to give 4-(4-chloro-2-fluoroanilino)-6-methoxy-7-(2-(2-[4-methylpiperazin-1-yl]ethoxy)ethoxy)quinazoline hydrochloride (54 mg, 28%).

$^1$H NMR Spectra: (DMSOd$_6$; CF$_3$COOD; 50° C.) 2.9(s, 3H); 3.5–3.8(m, 10H); 3.95(br s, 4H); 4.03(s, 3H); 4.4(m, 2H); 7.40–7.45(m, 1H); 7.42(s, 1H); 7.55–7.65(m, 2H); 8.15(s, 1H); 8.8(s, 1H); MS-ESI: 490 [MH]$^+$; Elemental analysis: Found C, 46.0; H, 5.6; N, 10.9; C$_{24}$H$_{29}$N$_5$O$_3$ClF 1.5H$_2$O 2.9HCl Requires C, 46.3; H, 5.6; N, 11.2%.

The starting material was prepared as follows:

2-Bromoethyl ether (1.57 ml, 12 mmol) was added to a mixture of 4-(4-chloro-2-fluoroanilino)-7-hydroxy-6-methoxyquinazoline (1 g, 3.1 mmol), (prepared as described for the starting material in Example 2), and potassium carbonate (1.73 g, 12 mmol) in DMF (10 ml). The mixture was s for 18 hours at ambient temperature and was partitioned between ethyl acetate and water. The organic layer was separated, washed with water and then brine, dried (MgSO$_4$) and the solvent removed by evaporation. The residue was purified by column chromatography on silica eluting with methylene chloride/acetonitrile/methanol (60/38/2). The purified product was triturated with ether, collected by filtration, washed with ether and dried under vacuum to give 7-(2-(2-bromoethoxy)ethoxy)-4-(4-chloro-2-fluoroanilino)-6-methoxyquinazoline (763 mg, 52%).

$^1$H NMR Spectrum: (CDCl$_3$) 3.5(t, 2H); 3.9(t, 2H); 3.95(t, 2H); 4.03(s, 3H); 4.35(t, 2H); 7.03(s, 1H); 7.2–7.4(m, 4H); 8.55(t, 1H); 8.7(s, 1H); MS-ESI: 472 [MH]$^+$.

EXAMPLE 64

A solution of 7-(2-(2-bromoethoxy)ethoxy)-4-chloro-2-fluoroanilino)-6-methoxyquinazoline (150 mg, 0.32 mmol), (prepared as described for the starting material in Example 63), in pyrrolidine (2 ml) was heated at 80° C. for 5 hours. The mixture was allowed to cool and was partitioned between ethyl acetate and water. The organic layer was washed with water and then brine, dried (MgSO$_4$) and the solvent removed by evaporation. The residue was purified by column chromatography on silica eluting with methylene chloride/methanol/triethylamine (80/20/0 followed by 80/20/1). The purified product was dissolved in methylene chloride and 2.9M ethereal hydrogen chloride (1 ml) was added. The volatiles were removed by evaporation, the residue was triturated with ether, collected by filtration and dried under vacuum to give 4-(4-chloro-2-fluoroanilino)-6-methoxy-7-(2-(2-pyrrolidin-1-ylethoxy)ethoxy)quinazoline hydrochloride (35 mg, 20%).

$^1$H NMR Spectrum: (DMSOd$_6$; CF$_3$COOD) 1.8–1.9(m, 2H); 1.95–2.1(m, 2H); 3.05–3.15(m, 2H); 3.45(t, 2H); 3.55–3.65(m, 2H); 3.8–3.85(m, 2H); 3.95–4.0(m, 2H); 4.01(s, 3H); 4.4(br s, 2H); 7.39(s, 1H); 7.48(d, 1H); 7.65(t, 1H); 7.7(d, 1H); 8.11(s, 1H); 8.89(s, 1H); MS-ESI: 461 [MH]$^+$; Elemental analysis: Found C, 49.4; H, 5.4; N, 10.1; C$_{23}$H$_{26}$N$_4$O$_3$ClF 1.2H$_2$O 2HCl Requires C, 49.7; H, 5.5; N, 10.1%.

EXAMPLE 65

1-(2-(2-Bromoethyl)ethoxy)-2-pyrrolidinone (272 mg, 1.1 mmol) was added to a mixture of 4-(4-chloro-2-fluoroanilino)-7-hydroxy-6-methoxyquinazoline (250 mg, 0.78 mmol), (prepared as described for the starting material in Example 2), and potassium carbonate (324 mg, 2.3 mmol) in DMF (5 ml) and the mixture stirred for 4 hours at ambient temperature. The mixture was partitioned between ethyl acetate and water, the organic layer was separated, washed with water and then brine, dried (MgSO$_4$) and the solvent removed by evaporation. The residue was purified by column chromatography on alumina eluting with methylene chloride/acetonitrile/methanol (60/37/3). The semi-purified product was repurified by column chromatography on silica eluting with methylene chloride/methanol (95/5). The purified product was dissolved in methylene chloride and 2.9M ethereal hydrogen chloride (1 ml) was added. The volatiles were removed by evaporation, the residue was triturated with ether, collected by filtration, washed with ether and dried under vacuum to give 4-(4-chloro-2-fluoroanilino)-6-methoxy-7-(2-(2-[2-oxopyrrolidin-1-yl]ethoxy)ethoxy)quinazoline hydrochloride (63 mg, 16%).

$^1$H NMR Spectrum: (DMSOd$_6$, CF$_3$COOD) 1.85–1.95(m, 2H); 2.2(t, 2H); 3.35–3.45(m, 4H); 3.65(t, 2H); 3.9(br s, 2H); 4.02(s, 3H); 4.35(br s, 2H); 7.35(s, 1H); 7.45(d, 1H); 7.65(t, 1H); 7.7(d, 1H); 8.15(s, 1H); 8.88(s, 1H); MS-ESI: 475 [MH]$^+$; Elemental analysis: Found C, 53.2; H, 5.0; N 11.1; C$_{23}$H$_{24}$N$_4$O$_4$ClF 0.6H$_2$O 0.85HCl Requires C, 53.5; H, 5.1; N, 10.8%.

The starting material was prepared as follows:

A solution of 2-pyrrolidinone (1.5 g, 17.6mmol) in anhydrous toluene (8 ml) was added dropwise to a suspension of sodium hydride (741 mg, 18 mmol, prewashed with pentane) in anhydrous toluene (60 ml) and the mixture was stirred at 100° C. for 1.5 hours. The mixture was allowed to cool to ambient temperature and tetrabutylammonium bromide (57 mg, 0.176 mmol) was added followed by 2-bromoethyl ether (8 ml, 35 mmol). The mixture was stirred for 21 hours at ambient temperature, the insolubles were removed by filtration and the solid was washed with ether. The volatiles were removed from the filtrate by evaporation and the residue was purified by column chromatography on silica eluting with methylene chloride/acetonitrile/methanol (60/38/2) to give 1-(2-(2-bromoethyl)ethoxy)2-pyrrolidinone (971 mg, 23%).

$^1$H NMR Spectrum: (CDCl$_3$) 2.0–2.1(m, 2H); 2.4(t, 2H); 3.4–3.5(m, 4H); 3.52(t, 2H); 3.65(t, 1H); 3.78(t, 2H); MS-(EI): 237 [M]$^+$.

EXAMPLE 66

Diethyl azodicarboxylate (325 µl, 2 mmol) was added dropwise to a mixture of (E)-4-morpholinobut-2-en-1-ol (151 mg, 0.96 mmol), (J. Med. Chem. 1972, 15, 110–112), 4-(4-chloro-2-fluoroanilino)-7-hydroxy-6-methoxyquinazoline (220 mg, 0.688 mol), (prepared as described for the starting material in Example 2), and triphenylphosphine (541 mg, 2 mmol) in methylene chloride (4 ml). The mixture was stirred for 30 minutes at ambient temperature, and further (E)-4-morpholinobut-2-en-1-ol (10 mg, 0.06 mmol), triphenylphosphine (36 mg, 0.137 mol) and diethyl azodicarboxylate (22 µl, 0.14 mmol) were added. The mixture was stirred for 20 minutes and the volatiles were removed by evaporation. The residue was purified by column chromatography on silica eluting with methylene chloride/methanol (92/8). The purified solid was dissolved in methylene chloride and 2M ethereal hydrogen chloride (3 ml) was added. The volatiles were removed by evaporation and the solid was triturated with ether, collected by filtration, washed with ether and dried under vacuum to give (E)-4-

(4-chloro-2-fluoroanilino)-6-methoxy-7-(4-morpholinobut-2-en-1-yloxy)quinazoline hydrochloride (165 mg, 45%).

$^1$H NMR Spectrum: (DMSOd$_6$; CF$_3$COOD) 3.1–3.15(m, 2H); 3.35–3.45(m, 2H); 3.75(t, 2H); 3.9(d, 2H); 4.0(d, 2H); 4.03(s, 3H); 4.95(d, 2H); 6.05(td, 1H); 6.3(td, 1H); 7.45(s, 1H); 7.47(d, 1H); 7.62(t, 1H); 7.7(d, 1H); 8.25(s, 1H); 8.88(s, 1H); MS-ESI: 459 [MH]$^+$; Elemental analysis: Found C, 50.3; H, 5.3; N, 10.1; C$_{23}$H$_{24}$N$_4$O$_3$ClF 1.4H$_2$O 1.8HCl Requires C, 50.2; H, 5.2; N, 10.2%.

EXAMPLE 67

Diethyl azodicarboxylate (368 μl, 2.34 mmol) was added dropwise to a mixture of 4-(4-bromo-2-fluoroanilino)-7-hydroxy-6-methoxyquinazoline (284 mg, 0.78 mmol), (prepared as described for the starting material in Example 48), triphenylphosphine (613 mg, 2.34 mmol) and 4-(2-hydroxyethyl)-3-morpholinone (170 mg, 1.17 mmol), (EP580402A2), in methylene chloride (10 ml) under nitrogen. The mixture was stirred for 2.5 hours at ambient temperature, the insolubles were removed by filtration. The filtrate was purified by pouring it directly on to a column of silica and eluting with methylene chloride/ethyl acetate/methanol (60/35/5). The purified product was triturated with ether and collected by filtration. The solid was dissolved in methylene chloride containing a few drops of methanol and 3.8M ethereal hydrogen chloride (0.5 ml) was added. The volatiles were removed by evaporation and the residue was triturated with ether, collected by filtration and dried under vacuum to give 4-(4-bromo-2-fluoroanilino)-6-methoxy-7-(2-(3-oxomorpholino)ethoxy)quinazoline hydrochloride (108 mg, 26%).

$^1$H NMR Spectrum: (DMSOd$_6$; CF$_3$COOD) 3.56(t, 2H); 3.8–3.9(m, 4H); 4.06(s, 3H); 4.06(s, 2H); 4.4(t, 2H); 7.35(s, 1H); 7.5–7.6(m, 2H); 7.8(d, 1H); 8.13(s, 1H); 8.87(s, 1H); MS-ESI: 491 [MH]$^+$; Elemental analysis: Found C, 47.1; H, 4.1; N, 10.5; C$_{21}$H$_{20}$N$_4$O$_4$BrF 0.3H$_2$O 0.95HCl Requires C, 47.5; H, 4.1; N, 10.5%.

EXAMPLE 68

Diethyl azodicarboxylate (283 μl, 1.8 mmol) was added dropwise to a mixture of 4-(4-bromo-2-fluoroanilino)-7-hydroxy-6-methoxyquinazoline (218 mg, 0.6 mmol), (prepared as described for the starting material in Example 48), triphenylphosphine (95 μl, 0.84 mmol) and 1-(2-hydroxyethyl)-2-pyrrolidinone (95 μl, 0.84 mmol) in methylene chloride (8 ml) under nitrogen. The mixture was stirred for 4 hours at ambient temperature, and then purified by pouring it directly on to a column of silica and eluting with methylene chloride/acetonitrile/methanol (60/32.5/7.5). The purified product was triturated with ether and collected by filtration. The solid was dissolved in methylene chloride/methanol (1/1) and 2M ethereal hydrogen chloride (1 ml) was added. The volatiles were removed by evaporation, the residue was triturated with ether, collected by filtration and dried under vacuum to give 4-(4-bromo-2-fluoroanilino)-6-methoxy-7-(2-(2-oxopyrrolidin-1-yl)ethoxy)quinazoline hydrochloride (182 mg, 60%).

$^1$H NMR Spectrum: (DMSOd$_6$; CF$_3$COOD) 1.9–2.0(m, 2H); 2.24(t, 2H); 3.53(t, 2H); 3.7(t, 2H); 4.01(s, 3H); 4.34(t, 2H); 7.36(s, 1H); 7.5–7.6(m, 2H); 7.75(d, 1H); 8.16(s, 1H); 8.87(s, 1H); MS-ESI: 477 [MH]$^+$; Elemental analysis: Found C, 50.2; H, 4.3; N, 10.9; C$_{21}$H$_{20}$N$_4$O$_3$BrF 0.8HCl Requires C, 50.0; H, 4.2; N, 11.1%.

EXAMPLE 69

Diethyl azodicarboxylate (236 μl, 1.5 mmol) was added dropwise to a mixture of 4-(4-bromo-2-fluoroanilino)-7-hydroxy-6-methoxyquinazoline (182 mg, 0.5 mmol), (prepared as described for the starting material in Example 48), triphenylphosphine (393 mg, 1.5 mmol) and 2-(2-methoxyethoxy)ethanol (84 μl, 0.7 mmol) in methylene chloride (7 ml) under nitrogen. The mixture was stirred for 4 hours at ambient temperature, the reaction mixture was purified by pouring it directly on to a column of silica and eluting with ethyl acetate/petroleum ether (9/1 followed by 10/0). The purified product was triturated with ether and collected by filtration. The solid was dissolved in methylene chloride/methanol and 2M ethereal hydrogen chloride (1 ml) was added. The mixture was concentrated by evaporation and the precipitate was collected by filtration, washed with ether and dried under vacuum to give 4-(4-bromo-2-fluoroanilino)-6-methoxy-7-(2-(2-methoxyethoxy)ethoxy) quinazoline hydrochloride (84 mg, 34%).

$^1$H NMR Spectrum: (DMSOd$_6$; CF$_3$COOD) 3.26(s, 3H); 3.47(m, 2H); 3.64(m, 2H); 3.85(m, 2H); 4.02(s, 3H); 4.35 (m, 2H); 7.35(s, 1H); 7.5–7.7(m, 2H); 7.82(d, 1H); 8.12(s, 1H); 8.87(s, 1H); MS-ESI: 468 [MH]$^+$; Elemental analysis: Found C, 47.5; H, 4.4; N, 8.7; C$_{20}$H$_{21}$N$_3$O$_4$BrF 0.65H$_2$O 0.65HCl Requires C, 47.9; H, 4.6; N, 8.3%.

EXAMPLE 70

Diethyl azodicarboxylate (567 μl, 3.6 mmol) was added dropwise to a mixture of 4-(4-chloro-2-fluoroanilino)-7-hydroxy-6-methoxyquinazoline (383 mg, 1.2 mmol), (prepared as described for the starting material in Example 2), 4-(3-hydroxypropyl)-3,5-dioxomorpholine (291 mg, 1.68 mmol) and triphenylphosphine (944 mg, 3.6 mmol) in methylene chloride (10 ml) under nitrogen. The mixture was sired at ambient temperature for 6 hours and the insolubles were removed by filtration. The filtrate was purified by pouring it directly on to a column of silica and eluting with methylene chloride/acetonitrile/methanol (60/34/6 followed by 60/24/16 and 60/16/24). The semi-purified product was repurified by column chromatography eluting with methylene chloride/acetonitrile/methanol (5/4/1). The purified product was dissolved in methylene chloride/methanol 2M ethereal hydrogen chloride (1 ml) was added and the volatiles were removed by evaporation. The residue was triturated with ether, collected by filtration, washed with ether and dried under vacuum to give 4-(4-chloro-2-fluoroanilino)-7-(3-(3,5-dioxomorpholino)propoxy)-6-methoxyquinazoline hydrochloride (56 mg, 10%).

$^1$H NMR Spectrum: (DMSOd$_6$; CF$_3$COOD) 2.0–2.1(m, 2H); 3.35(t, 2H); 3.98(s, 2H); 4.01(s, 3H); 4.24(t, 2H); 7.33(s, 1H); 7.45(d, 1H); 7.62(t, 1H); 7.68(d, 1H); 8.13(s, 1H); 8.87(s, 1H); MS-ESI: 475 [MH]$^+$; Elemental analysis: Found C, 48.9; H, 4.4; C$_{22}$H$_{20}$N$_4$O$_5$ClF 1.4H$_2$O 1HCl Requires C, 49.2; H, 4.5.

The starting material was prepared as follows:

A solution of diglycolic anhydride (2.32 g, 20 mmol) in 3-amino-1-propanol (6 ml) was refluxed at 180° C. for 3 hours. The volatiles were removed by evaporation and the residue was purified by column chromatography on silica eluting with methylene chloride/methanol (8/2) to give 4-(3-hydroxypropyl)-3,5-dioxomorpholine (3.46 g, 99%).

$^1$H NMR Spectrum: (CDCl$_3$) 2.75–2.8(m, 2H); 3.1(br s, 1H); 3.45–3.5(m, 2H); 3.75(t, 2H); 4.04(s, 2H); MS-(EI): 174 [MH]$^+$.

EXAMPLE 71

Diethyl azodicarboxylate (472 μl, 3 mmol) was added dropwise to a mixture of 4-(4-chloro-2-fluoroanilino)-7- hydroxy-6-methoxyquinazoline (319.5 mg, 1 mmol), (prepared as described for the staring material in Example 2), triphenylphosphine (786 mg, 3 mmol) and 4-(2-hydroxyethyl)-3,5-dioxomorpholine (223 mg, 1.4 mmol) in methylene chloride (10 ml) under nitrogen. The mixture was stirred at ambient temperature for 4.5 hours and the insolubles were removed by filtration. The solvent was removed from the filtrate by evaporation and the residue was purified by column chromatography eluting with methylene chloride/acetonitrile/methanol (85/12.5/2.5). The purified product was dissolved in methylene chloride, 2M ethereal hydrogen chloride (1 ml) was added and the mixture was diluted with ether. The resulting precipitate was collected by filtration, washed with ether and dried under vacuum to give 4-(4-chloro-2-fluoroanilino)-7-(2-(3,5-dioxomorpholino) ethoxy)-6-methoxyquinazoline hydrochloride (97 mg, 20%).

$^1$H NMR (DMSOd$_6$; CF$_3$COOD) 4.0(s, 3H); 4.19(d, 2H); 4.39(t, 2H); 4.45(s, 4H); 7.35(s, 1H); 7.45(d, 1H); 7.67(t, 1H); 7.69(d, 1H); 8.12(s, 1H); 8.87(s, 1H); MS-ESI: 461 [MH]$^+$; Elemental analysis: Found C, 49.9; H, 3.9; N, 11.1; C$_{21}$H$_{18}$N$_4$O$_5$ClF 0.5H$_2$O 0.9HCl Requires C, 50.2; H, 4.0; N, 11.1%.

The starting material was prepared as follows:

Ethanolamine (2.44 g, 40 mmol) was added dropwise to a solution of diglycolic anhydride (2.32 g, 20 mmol) in pyridine (10 ml). The mixture was stirred for 5 minutes at ambient temperature and then heated at reflux for 2 hours. The volatiles were removed by evaporation and the residue was heated at 180° C. for 2 hours The reaction mixture was allowed to cool and was purified by column chromatography eluting with methylene chloride/methanol (9/1) to give 4-(2-hydroxyethyl)-3,5-dioxomorpholine (400 mg, 12.5%).

$^1$H NMR Spectrum: (CDCl$_3$) 1.6(br s, 1H); 3.8(t, 2H); 4.05(t, 2H); 4.4(s, 4H); MS-EI: 160[MH]$^+$;

EXAMPLE 72

Diethyl azodicarboxylate (378 μl, 2.4 mmol) was added dropwise to a mixture of 4-(4-bromo-2-fluoroanilino)-7-hydroxy-6-methoxyquinazoline (292 mg, 0.8 mmol), (prepared as described for the starting material in Example 48), triphenylphosphine (629 mg, 2.4 mmol) and 2-(2-morpholinoethoxy)ethanol (196 mg, 1.12 mmol), (prepared as described for the starting material in Example 53), in methylene chloride (10 ml) under nitrogen. The mixture was stirred for 3.5 hours at ambient temperature and the mixture was purified by pouring it directly on to a column of silica and eluting with methylene chloride/acetonitrile/methanol 6/3/1). The purified product was dissolved in methylene chloride/methanol and the insolubles were removed by filtration. 2M Ethereal hydrogen chloride (1 ml) was added to the filtrate and the volatiles were removed by evaporation. The residue was triturated with ether, collected by filtration, washed with ether and dried under vacuum to give 4-(4-bromo-2-fluoroanilino)-6-methoxy-7-(2-morpholinoethoxy)ethoxy)quinazoline hydrochloride (232 mg, 49%).

$^1$H NMR Spectrum: (DMSOd$_6$; CF$_3$COOD) 3.1–32(m, 2H); 3.35–3.4(br s, 2H); 3.45(d, 2H); 3.75(t, 2H); 3.9–4.0 (m,6H); 4.02(s, 3H); 4.4(br s, 2H); 7.45(s, 1H); 7.5–7.6(m, 2H); 7.8(m, 1H); 8.22(s, 1H); 8.87(s, 1H); MS-ESI: 523 [MH]$^+$; Elemental analysis: Found C, 46.3; H, 4.9; N, 9.2; C$_{23}$H$_{26}$N$_4$O$_4$BrF 0.5H$_2$O 1.8HCl Requires C, 46.3; H, 4.9; N, 9.4%.

EXAMPLE 73

Diethyl azodicarboxylate (220 μl, 1.4 mmol) was added dropwise to a mixture of 4-(4-bromo-2-fluoroanilino)-7-hydroxy-6-methoxyquinazoline (170 mg, 0.46 mmol), (prepared as described for the starting material in Example 48), triphenylphosphine (367 mg, 1.4 mmol) and 3-(1,1-dioxothiomorpholino)-1-propanol (135 mg, 0.7 mmol) in methylene chloride (4 ml) under nitrogen. The mixture was stirred for 1 hour at ambient temperature and further triphenylphosphine (61 mg, 0.23 mmol), 3-(1,1-dioxothiomorpholino)-1-propanol (30 mg, 0.23 mmol) and diethyl azodicarboxylate (37 μl, 0.23 mmol) were added. The mixture was stirred for 1 hour at ambient temperature and the mixture was purified by pouring it on to a column of silica and eluting with methylene chloride/methanol (95/5). The purified product was dissolved in methylene chloride/methanol, 2.2M ethereal hydrogen chloride (1 ml) was added and the volatiles were removed by evaporation. The residue was triturated with ether, collected by filtration, washed with ether and dried under vacuum to give 4-(4-bromo-2-fluoroanilino)-7-(3-(1,1-dioxothiomorpholino) propoxy)-6-methoxyquinazoline hydrochloride (138 mg, 47%).

$^1$H NMR Spectrum: (DMSOd$_6$; CF$_3$COOD) 2.3–2.4(m, 2H); 3.5(t, 2H); 3.7–3.8(br s, 4H); 3.85(br s, 4H); 4.03(s, 3H); 4.35(t, 2H); 7.4(s, 1H); 7.5–7.6(m, 2H); 7.8(d, 1H); 8.21(s, 1H); 8.88(s, 1H); MS-ESI: 539 [MH]$^+$; Elemental analysis: Found C, 42.1; H, 4.6; N, 8.6; C$_{22}$H$_{24}$N$_4$O$_4$BrFS 1.1H$_2$O 1.85HCl Requires C, 42.2; H, 4.5; N, 8.9%.

The starting material was prepared as follows:

A mixture of 3-amino-1-propanol (650 μl, 8.4 mmol) and vinyl sulphone (1 g, 8.4 mmol) was heated at 110° C. for 45 minute The mixture was allowed to cool and was purified by column chromatography eluting with methylene chloride/methanol (95/5) to give 3-(1,1-dioxothiomorpholino)-1-propanol (800 mg, 90%).

$^1$H NMR Spectrum: (CDCl$_3$) 1.7–1.8(m, 2H); 2.73(t, 2H); 3.06(br s, 8H); 3.25(s, 1H); 3.78(t, 2H); MS-ESI: 194 [MH]$^+$.

EXAMPLE 74

A solution of 2-methoxyethylsulphonyl chloride (42 mg, 0.26 mmol), (J. Amer. Chem. Soc. 1992, 114, 1743–1749), in acetonitrile (1 ml) was added to a mixture of 4-(4-chloro-2-fluoroanilino)-6-methoxy-7-(2-methylaminoethoxy) quinazoline (94 mg, 0.25 mmol), (prepared as described for the starling material in Example 60), and triethylamine (80 μl, 0.5 mmol) in acetonitrile (15 ml). The mixture was stirred for 10 minutes at ambient temperature, the volatiles were removed by evaporation and the residue was partitioned between methylene chloride and water. The organic layer was separated, washed with brine, dried (MgSO$_4$) and the solvent removed by evaporation. The residue was purified by column chromatography eluting with methylene chloride/methanol (97/3). The purified product was dissolved in methylene chloride (5 ml) and 2.2M ethereal hydrogen chloride (2 ml) was added and the volatiles were removed by evaporation. The residue was triturated with ether, collected by filtration, washed with ether and dried under vacuum to give 4-(4-chloro-2-fluoroanilino)-7-(2-([N-methyl-N-(2-methoxyethylsulphonyl)]amino)ethoxy)6-methoxyquinazoline hydrochloride (86 mg, 64%).

$^1$H NMR Spectrum: (DMSOd$_6$; CF$_3$COOD) 2.96(s, 3H); 3.28(s, 3H); 3.47(t, 2H); 3.6–3.7(m, 4H); 4.02(s, 3H); 4.37(t, 2H); 7.37(s, 1H); 7.46(d, 1H); 7.64(t, 1H); 7.7(d, 1H); 8.15(s, 1H); 8.88(s, 1H); MS-ESI 499 [MH]$^+$; Elemental analysis: Found C, 47.2; H, 4.9; N, 10.2; C$_{21}$H$_{24}$N$_4$O$_5$ClFS 1HCl Requires C, 47.1; H, 4.7; N, 10.5%.

EXAMPLE 75

Using a method analogous to that in Example 74, a mixture of 4-(4-chloro-2-fluoroanilino)-6-methoxy-7-(2- methylaminoethoxy)quinazoline (102 mg, 0.27 mmol), (prepared as described for the staring material in Example 60), and triethylamine (0.1 ml, 0.72 mmol) in acetonitrile (17 ml) was treated with 3-morpholinopropylsulphonyl chloride (75 mg, 0.28 mmol), (WO 930181), to give, after purification and hydrochloride salt formation, 4-(4-chloro-2-fluoroanilino)-6-methoxy-7-(2-([N-methyl-N-(3-morpholinopropylsulphonyl)]amino)ethoxy)quinazoline hydrochloride (96 mg, 54%).

$^1$H NMR Spectrum: (DMSOd$_6$; CF$_3$COOD) 2.1–2.2(m, 2H); 3.0(s, 3H); 3.05–3.15(m, 2H); 3.2–3.3(m, 2H); 3.3–3.4 (m, 2H); 3.45(d, 2H); 3.65–3.8(m, 4H); 3.95(d, 2H); 4.03(s, 3H); 4.39(t, 2H); 7.42(s, 1H); 7.45(d, 1H); 7.65(t, 1H); 7.7(d, 1H); 8.2(s, 1H); 8.9(s, 1H); MS-ESI: 568 [MH]$^+$.

EXAMPLE 76

Diethyl azodicarboxylate (0.18 ml, 1.14 mmol) was added dropwise to a mixture of 4-(4-chloro-2-fluoroanilino)-7-hydroxy-6-methoxyquinazoline (111 mg, 0.35 mmol), (prepared as described for the staring material in Example 2), triphenylphosphine (312 mg, 1.19 mmol) and (S)-1-(3-hydroxypropyl)-2-(N,N-dimethylcarbamoyl)pyrrolidine (84 mg, 0.42 mmol) in methylene chloride (10 ml) cooled at 0° C. under nitrogen. The mixture was stirred for 15 minutes at 0° C., the mixture was allowed to warm to ambient temperature and was then stirred for 22 hours. Further (S)-1-(3-hydroxypropyl)-2-(N,N-diethylcarbamoyl)pyrrolidine (10 mg, 0.05 mmol), triphenylphosphine (35 mg, 0.13 mmol) and diethyl azodicarboxylate (20 μl, 0.13 mmol) were added and the mixture was stirred for a further 2 hours. The mixture was partitioned between water and methylene chloride and the aqueous phase was adjusted to pH2 with 2M hydrochloric acid. The aqueous layer was separated, adjusted to pH9 with sodium hydrogen carbonate and was extracted with methylene chloride. The combined organic extracts were washed with water and then brine, dried (MgSO$_4$) and the solvent removed by evaporation. The residue was purified by column chromatography on silica eluting with methylene chloride/methanol (85/15 followed by 75/25 and 60/40). The purified product was dissolved in methylene chloride (5 ml) and methanol (1 ml), 3.9M ethereal hydrogen chloride (0.5 ml) was added and the mixture was diluted with ether. The resulting precipitate was collected by filtration, washed with ether, and dried under vacuum to give (S)-4-(4-chloro-2-fluoroanilino)-7-(3-(2-(N, N-dimethylcarbamoyl)pyrrolidin-1-yl)propoxy)-6-methoxyquinazoline hydrochloride (86 mg, 32%).

$^1$H NMR Spectrum: (DMSOd$_6$; CF$_3$COOD) 1.8–1.95(m, 2H); 2.1–2.3(m, 4H); 2.92(s, 3H); 3.0(s, 3H); 3.2–3.45(m, 3H); 3.75–3.85(m, 1H); 4.0(s, 3H); 4.32(t, 2H); 4.75(t, 1H); 7.4(s, 1H); 7.45(d, 1H); 7.65(t, 1H); 7.7(d, 1H); 8.25(s, 1H); 8.9(s, 1H); MS-ESI: 502 [MH]$^+$; Elemental analysis: Found C, 50.2; H, 5.5; N, 11.6; C$_{25}$H$_{29}$N$_5$O$_3$ClF 1H$_2$O$_2$HCl Requires C, 50.6; H, 5.6; N, 11.8%.

The starting material was prepared as follows:

A mixture of (S)-2-(N,N-dimethylcarbamoyl)pyrrolidine (426 mg, 3 mmol), (Chem. pharm. Bull. 1973, 21, 2112–2116), 3-bromo-1-propanol (0.41 ml, 4.5 mmol) and potassium carbonate (829 mg, 6 mmol) in acetonitrile (6 ml) was heated at reflux for 8 hours. The mixture was allowed to cool and was partitioned between methylene chloride and water. The organic layer was separated, washed with brine, dried (MgSO$_4$) and the solvent removed by evaporation. The residue was purified by column chromatography, eluting with methylene chloride/methanol (a gradient from 90/10 to 60/40) to give (S)-1-(3-hydroxypropyl)-2-(N,N-dimethylcarbamoyl)pyrrolidine (290 mg, 48%).

$^1$H NMR Spectrum: (CDCl$_3$; CD$_3$COOD) 1.8–2.1(m, 4H); 2.2–2.3(m, 1H); 2.6–2.7(m,1H); 3.0(s, 3H); 3.10(s, 3H); 3.4–3.6(m, 31); 3.75–3.85(m, 3H); 5.05(m, 1H); MS-ESI: 223 [MH]$^+$.

EXAMPLE 77

The following illustrate representative pharmaceutical dosage forms containing the compound of formula I, or a pharmaceutically acceptable salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur | 488.5 |
| Magnesium stearate | 1.5 |

| (e) Injection I | (50 mg/ml) |
|---|---|
| Compound X | 5.0% w/v |
| IN Sodium hydroxide solution | 15.0% v/v |
| 0.1N Hydrochloric acid (to adjust pH to 7.6) | |
| Polyethylene glycol 400 | 4.5% w/v |
| Water for injection to 100% | |

| (f) Injection II | 10 mg/ml) |
|---|---|
| Compound X | 1.0% w/v |
| Sodium phosphate BP | 3.6% w/v |
| 0.1N Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26%w/v |
| Citric acid | 0.38%w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

What is claimed is:
1. A quinazoline derivative of the formula I:

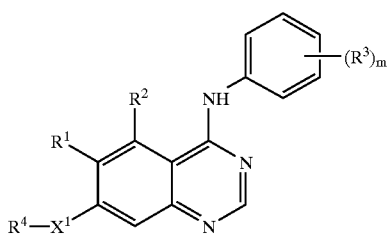

(I)

wherein:
m is an integer from 1 to 2;
R$^1$ represents hydrogen, hydroxy, halogeno, nitro, trifluoromethyl, cyano, $C_{1-3}$alkyl, $C_{1-3}$alkoxy, $C_{1-3}$alkylthio, or —NR$^5$R$^6$ (wherein R$^5$ and R$^6$, which may be the same or different, each represents hydrogen or $C_{1-3}$alkyl);
R$^2$ represents hydrogen, hydroxy, halogeno, methoxy, amino or nitro;
R$^3$ represents hydroxy, halogeno, $C_{1-3}$alkyl, $C_{1-3}$alkoxy, $C_{1-3}$alkanoyloxy, trifluoromethyl, cyano, amino or nitro;
X$^1$ represents —O—,
R$^4$ is selected from one of the following eleven groups:
1) $C_{1-5}$alkylR$^{12}$ (wherein R$^{12}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituent selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl) or $C_{1-5}$alkylR$^{13}$ (wherein R$^{13}$ is a group selected from pyrrolidin-1-yl, imidazolidin-1-yl and thiomorpholino, which group may bear one or two substituent selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl) carbamoyl, $C_{1-4}$alkanoyl and $C_{1-4}$alkoxycarbonyl);
2) $C_{2-5}$alkenylR$^{14}$ (wherein R$^{14}$ is a 5 or 6 membered saturated heterocyclic group with one or two heteroatoms, selected independently from O, S and N, which heterocyclic group may bear one or two substituent selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
3) $C_{3-5}$alkynylR$^{15}$ (wherein R$^{15}$ is a 5 or 6 membered saturated heterocyclic group with one or two heteroatoms, selected independently from O, S and N, which heterocyclic group may bear one or two substituent selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
4) $C_{1-5}$alkylX$^2C_{1-5}$alkylX$^3R^{16}$ (wherein X$^2$ and X$^3$ which may be the same or different are each —O—, —S—, —SO—, —SO$_2$—, —NR$^{17}$CO—, —CONR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, $C_{1-3}$alkyl or $C_{1-3}$alkoxyC$_{2-3}$alkyl) and R$^{16}$ represents hydrogen or $C_{1-3}$alkyl);
5) $C_{1-5}$alkylX$^4$COR$^{22}$ (wherein X$^4$ represents —O— or —NR$^{23}$— (wherein R$^{23}$ represents hydrogen, $C_{1-3}$alkyl or $C_{1-3}$alkoxyC$_{2-3}$alkyl) and R$^{22}$ represents —NR$^{24}$R$^{25}$ or —OR$^{26}$ (wherein R$^{24}$, R$^{25}$ and R$^{26}$ which may be the same or different each represents hydrogen, $C_{1-4}$alkyl or $C_{1-3}$alkoxyC$_{2-3}$alkyl));
6) $C_{1-5}$alkylX$^5R^{27}$ (wherein X$^5$ represents —O—, —S—, —SO—, —SO$_2$—, —OCO—, —NR$^{28}$CO—, —CONR$^{29}$—, —SO$_2$NR$^{30}$—, —NR$^{31}$SO$_2$— or —NR$^{32}$— (wherein R$^{28}$, R$^{29}$, R$^{30}$, R$^{31}$ and R$^{32}$ each independently represents hydrogen, $C_{1-3}$alkyl or $C_{1-3}$alkoxyC$_{2-3}$alkyl) or X$^5$ is carbonyl, and R$^{27}$ represents cyclopentyl, cyclohexyl or a 5 or 6 membered saturated heterocyclic group with one or two heteroatoms, selected independently from O, S and N, which cyclopentyl, cyclohexyl or heterocyclic group may bear one or two substituent selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl or R$^{27}$ is $C_{1-3}$allyl with the proviso that when R$^{27}$ is $C_{1-3}$alkyl, X$^5$ is —S—, —SO—, —SO$_2$—, —SO$_2$NR$^{30}$— or —NR$^{31}$SO$_2$—;
7) $C_{1-3}$alkoxyC$_{2-4}$alkyl or $C_{1-4}$alkyl;
8) $C_{1-5}$alkylX$^6C_{1-5}$alkylR$^{33}$ (wherein X$^6$ represents —O—, —S—, —SO—, —SO$_2$—, —NR$^{34}$CO—, —CONR$^{35}$—, —SO$_2$NR$^{36}$—, —NR$^{37}$SO$_2$— or —NR$^{38}$— (wherein R$^{34}$, R$^{35}$, R$^{36}$, R$^{37}$ and R$^{38}$ each independently represents hydrogen, $C_{1-3}$alkyl or $C_{1-3}$alkoxyC$_{2-3}$alkyl) and R$^{33}$ represents cyclopentyl, cyclohexyl or a 5 or 6 membered saturated heterocyclic group with one or two heteroatoms, selected independently from O, S and N, which cyclopentyl, cyclohexyl or heterocyclic group may bear one or two substitutes selected from oxo, hydroxy, halogeno, $C_{1-4}$alkyl), $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
9) R$^{39}$ (wherein R$^{39}$ is a group selected from pyrrolidin-3-yl, piperidine-3-yl and piperidine-4-yl which group may bear one or two substituent selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl);
10) $C_{1-5}$alkylR$^{40}$ (wherein R$^{40}$ is piperazin-1-yl which bears at least one substituent selected from $C_{1-4}$alkanoyl, $C_{1-4}$alkoxycarbonyl, $C_{1-4}$hydroxyalkyl and —CONR$^{41}$R$^{42}$ (wherein R$^{41}$ and R$^{42}$ each independently represents hydrogen or $C_{1-4}$alkyl); and
11) $C_{1-5}$alkylR$^{44}$ (wherein R$^{44}$ is morpholino which bears at least one and optionally two substituent selected from oxo, $C_{1-4}$alkyl, $C_{1-4}$hydroxyalkyl, carbamoyl, $C_{1-4}$alkylcarbamoyl, N,N-di($C_{1-4}$alkyl) carbamoyl, $C_{1-4}$alkanoyl and $C_{1-4}$alkoxycarbonyl);
with the further proviso that when R$^4$ is selected from group 7) R$^1$ and/or R$^2$ is/are nitro or at least one R$^3$ is $C_{1-3}$alkanoyloxy;
or a salt thereof.
2. A quinazoline derivative as claimed in claim 1 wherein R$^1$ represents hydrogen, hydroxy, cyano, nitro, trifluoromethyl, methyl, ethyl, methoxy or ethoxy.

3. A quinazoline derivative as claimed in claim 1 or claim 2 wherein $R^2$ is hydrogen.

4. A quinazoline derivative as claimed in claim 1 or claim 2 wherein the phenyl group bearing $(R^3)_m$ is of the formula II:

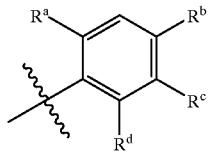

(II)

wherein:
$R^a$ represents hydrogen, methyl, fluoro, or chloro;
$R^b$ represents hydrogen, methyl, methoxy, bromo, fluoro or chloro;
$R^c$ represents hydrogen or hydroxy;
$R^d$ represents hydrogen, fluoro or chloro.

5. A quinazoline derivative as claimed in claim 1 or claim 2 wherein $R^4$ is selected from one of the following nine groups:

1) $C_{1-4}alkylR^{12}$ (wherein $R^{12}$ is a group selected from 1,3-dioxolan-2-yl, 1,3-dioxan-2-yl, 1,3-dithiolan-2-yl, 1,3-dithian-2-yl, pyrrolidin-2-yl, pyrrolidin-3-yl, piperidine-2-yl, piperidine-3-yl, piperidine-4-yl, morpholin-2-yl, morpholin-3-yl and piperazin-2-yl which group may bear one or two substituents selected from oxo, hydroxy, halogeno, $C_{1-3}alkyl$, $C_{1-3}hydroxyalkyl$, $C_{1-3}alkoxy$, carbamoyl, $C_{1-3}alkylcarbamoyl$, N,N-di($C_{1-3}alkyl$)carbamoyl, $C_{2-3}alkanoyl$ and $C_{1-3}alkoxycarbonyl$) or $C_{2-4}alkylR^{45}$ (wherein $R^{45}$ is a group selected from imidazolidine-1-yl, pyrrolidin-1-yl and thiomorpholino which group may bear one or two substituents selected from oxo, hydroxy, halogeno, $C_{1-3}alkyl$, $C_{1-3}hydroxyalkyl$, $C_{1-3}alkoxy$, carbamoyl, $C_{1-3}alkylcarbamoyl$, N,N-di($C_{1-3}alkyl$)carbamoyl, $C_{2-3}alkanoyl$ and $C_{1-3}alkoxycarbonyl$);

2) 1-$R^{46}$prop-1-en-3-yl, 1-$R^{46}$but-2-en-4-yl, 1-but-1-en-3-yl, 1-$R^{46}$pent-2-en-4-yl or 2-$R^{46}$pent-3-en-5yl (wherein $R^{46}$ is a 5 or 6 membered saturated heterocyclic group with one or two heteroatoms, selected independently from O, S and N, which heterocyclic group is linked to the alkenyl group through a carbon atom and which heterocyclic group may bear one or two substituent selected from oxo, hydroxy, halogeno, $C_{1-3}alkyl$, $C_{1-3}hydroxyalkyl$, $C_{1-3}alkoxy$, carbamoyl, $C_{1-3}alkylcarbamoyl$, N,N-di($C_{1-3}alkyl$)carbamoyl, $C_{2-3}alkanoyl$ and $C_{1-3}alkoxycarbonyl$) or 1-$R^{47}$but-2-en-4-yl, 1-$R^{47}$pent-2-en-4-yl or 2-$R^{47}$pent-3-en-5-yl (wherein $R^{47}$ is a 5 or 6 membered saturated heterocyclic group with one or two heteroatoms, of which one is N and the other is selected independently from O, S and N, which heterocyclic group is linked to the alkenyl group through a nitrogen atom and which heterocyclic group may bear one or two substituents selected from oxo, hydroxy, halogeno, $C_{1-3}alkyl$, $C_{1-3}hydroxyalkyl$, $C_{1-3}alkoxy$, carbamoyl, $C_{1-3}alkylcarbamoyl$, N,N-di($C_{1-3}alkyl$)carbamoyl, $C_{2-3}alkanoyl$ and $C_{1-3}alkoxycarbonyl$);

3) 1-$R^{48}$prop-1-yn-3-yl, 1-$R^{48}$but-2-yn-4-yl, 1-$R^{48}$but-1-yn-3-yl, 1-$R^{48}$pent-2-yn-4-yl or 2-$R^{48}$pent-3-yn-5-yl (wherein $R^{48}$ is a 5 or 6 membered saturated heterocyclic group with one or two heteroatoms, selected independently from O, S and N, which heterocyclic group is linked to the alkynyl group through a carbon atom and which heterocyclic group may bear one or two substituents selected from oxo, hydroxy, halogeno, $C_{1-3}alkyl$, $C_{1-3}hydroxyalkyl$, $C_{1-3}alkoxy$, carbamoyl, $C_{1-3}alkylcarbamoyl$, N,N-di($C_{1-3}alkyl$)carbamoyl, $C_{2-3}alkanoyl$ and $C_{1-3}alkoxycarbonyl$) or 1-$R^{49}$but-2-yn-4-yl, 1-$R^{49}$pent-2-yn-4-yl or 2-$R^{49}$pent-3-yn-5-yl (wherein $R^{49}$ is a 5 or 6 membered saturated heterocyclic group with one or two heteroatoms, of which one is N and the other is selected independently from O, S and N, which heterocyclic group is linked to the alkynyl group through a nitrogen atom and which heterocyclic group may bear one or two substituents selected from oxo, hydroxy, halogeno, $C_{1-3}alkyl$, $C_{1-3}hydroxyalkyl$, $C_{1-3}alkoxy$, carbamoyl, $C_{1-3}alkylcarbamoyl$, N,N-di($C_{1-3}alkylcarbamoyl$, $C_{2-3}alkanoyl$ and $C_{1-3}alkoxycarbonyl$);

4) $C_{2-3}alkylX^2C_{1-3}alkylX^3R^{16}$ (wherein $X^2$ and $X^3$ are as defined in claim 1 and $R^{16}$ represents hydrogen or $C_{1-3}alkyl$);

5) $C_{2-3}alkylX^4COR^{22}$ (wherein $X^4$ is as defined in claim 1 and $R^{22}$ represents —$NR^{24}R^{25}$ or —$OR^{26}$ (wherein $R^{24}$, $R^{25}$ and $R^{26}$ which may be the same or different each represents hydrogen, $C_{1-4}alkyl$ or $C_{1-2}alkoxyethyl$));

6) $C_{2-3}alkylX^5R^{27}$ (wherein $X^5$ is as defined in claim 1 and $R^{27}$ represents a group selected from cyclopentyl, cyclohexyl, pyrrolidinyl and piperidinyl which group is linked to $X^5$ through a carbon atom and which group may carry one substituent selected from oxo, hydroxy, halogeno, $C_{1-2}alkyl$, $C_{1-2}hydroxyalkyl$, $C_{1-2}alkoxy$, carbamoyl, $C_{1-2}alkylcarbamoyl$, N,N-di($C_{1-2}alkyl$) carbamoyl, acetyl and $C_{1-2}alkoxycarbonyl$ or $R^{27}$ is $C_{1-3}alkyl$ with the proviso that when $R^{27}$ is $C_{1-3}alkyl$, $X^5$ is —S—, —SO—, —$SO_2$—, —$SO_2N^{30}$— or —$NR^{31}SO_2$—);

7) $C_{2-3}alkylX^6C_{2-3}alkyl^{33}$ (wherein $X^6$ is as defined in claim 1 and $R^{33}$ represents a 5 or 6 membered saturated heterocyclic group with one or two heteroatoms, selected independently from O, S and N, which heterocyclic group may bear one or two substituent selected from oxo, hydroxy, halogeno, $C_{1-3}alkyl$, $C_{1-3}hydroxyalkyl$, $C_{1-3}alkoxy$, carbamoyl, $C_{1-3}alkylcarbamoyl$, N,N-di($C_{1-3}alkyl$)carbamoyl, $C_{2-3}alkanoyl$, and $C_{1-3}alkoxycarbonyl$);

8) $C_{2-3}alkylR^{40}$ is piperazin-1-yl which bears at least one substituent selected from acetyl, $C_{1-2}alkoxycarbonyl$, $C_{1-2}hydroxyalkyl$ and $CONR^{41}R^{42}$ (wherein $R^{41}$ and $R^{42}$ each independently represents hydrogen or $C_{1-2}alky$); and 9) $C_{2-3}alkylR^{44}$ is morpholino which bears at least one and optionally two substituents selected from oxo, $C_{1-2}alky$, $C_{1-2}hydroxyalkyl$, carbamoyl, $C_{1-2}alkylcarbamoyl$, N,N-di($C_{1-2}alkyl$)carbamoyl, acaetyl and $C_{1-2}alkoxycarbonyl$).

6. A quinazoline derivative as claimed in claim 5 wherein $R^4$ is selected from one of the following seven groups:

1) $C_1$–$3alkylR^{12}$ (wherein $R^{12}$ is a group selected from 1,3-dioxolan-2-yl, 1,3-dioxan-2-yl, 1,3-dithiolan-2-yl, 1,3-dithian-2-yl, pyrrolidin-2-yl, pyrrolidin-3-yl, piperidin-2-yl, piperidin-3-yl, piperidin-4-yl, morpholin-2-yl, morpholin-3-yl and piperazin-2-yl which group may bear one or two substituents selected from oxo, hydroxy, halogeno, $C_{1-2}alkyl$, $C_{1-2}hydroxyalkyl$, $C_{1-2}alkoxy$, carbamoyl, $C_{1-2}$alkylcarbamoyl, N,N-di($C_{1-2}$alkyl)carbamoyl, acetyl and $C_{1-2}$alkoxycarbonyl) or $C_{2-3}$alkyl$R^{45}$ (wherein $R^{45}$ is a group selected from imidazolidin-1-yl, pyrrolidin-1-yl and thiomorpholino which group may bear one or two substituents selected from oxo, hydroxy, halogeno, $C_{1-2}$alkyl, $C_{1-2}$hydroxyalkyl, $C_{1-2}$alkoxy, carbamoyl, $C_{1-2}$alkylcarbamoyl, N,N-di($C_{1-2}$alkyl)carbamoyl, acetyl and $C_{1-2}$alkoxycarbonyl];

2) 1-$R^{50}$but-2-en-4-yl (wherein $R^{50}$ is a group selected from imidazolidin-1-yl, 1,3-dioxolan-2-yl, 1,3-dioxan-2-yl, 1,3-dithiolan-2-yl, 1,3-dithian-2-yl, piperidin-4-yl, pyrrolidin-1-yl, pyrrolidin-3-yl, piperazin-1-yl, morpholino, thiomorpholino and piperidino which group may bear one or two substituents selected from oxo, hydroxy, halogeno, $C_{1-2}$alkyl, $C_{1-2}$hydroxyalkyl, $C_{1-2}$alkoxy, carbamoyl, $C_{1-2}$alkylcarbamoyl, N,N-di($C_{1-2}$alkyl)carbamoyl, acetyl and $C_{1-2}$alkoxycarbonyl).

3) 1-$R^{51}$but-2-yn-4-yl (wherein $R^{51}$ is a group selected from imidazolidin-1-yl, 1,3-dioxolan-2-yl, 1,3-dioxan-2-yl, 1,3-dithiolan-2-yl, 1,3-dithian-2-yl, piperidin-4-yl, pyrrolidin-1-yl, pyrrolidin-3-yl, piperazin-1-yl morpholino, thiomorpholino and piperidino which group may bear one or two substituents selected from oxo, hydroxy, halogeno, $C_{1-2}$alkyl, $C_{1-2}$hydroxyalkyl, $C_{1-2}$alkoxy, carbamoyl, $C_{1-2}$alkylcarbamoyl, N,N-di($C_{1-2}$alkyl)carbamoyl, acetyl and $C_{1-2}$alkoxycarbonyl);

4) $C_{2-3}$alkyl$X^2C_{1-3}$alkyl$X^3R^{16}$ (wherein $X^2$ and $X^3$ are as defined in claim 1 and $R^{16}$ represents hydrogen or $C_{1-3}$alkyl);

5) 2-(3,3-dimethylureido)ethyl, 3-(3,3dimethylureido) propyl, 2-(3-methylureido)ethyl, 3-(3-methylureido) propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, 2-(1,3,3-trimethylureido) ethyl, 3-1,3,3-trimethylureido)propyl, 2-(isopropoxycarbonylamino)ethyl, 3-(isopropoxycarbonylamino)propyl, 2-(isobutoxycarbonylamino)ethyl, 3-(isobutoxycarbonylamino)propyl, 2-(t-butoxycarbonylamino)ethyl or 3-(t-butoxycarbonylamino)propyl;

6) $C_{2-3}$alkyl$X^5R^{27}$ (wherein $R^{27}$ is $C_{1-2}$alkyl and $X^5$ is —S—, —SO—, —SO$_2$—, —SO$_2$NR$^{30}$— or —NR$^{31}$ SO$_2$—; and 7) $C_{2-3}$alky$X^6C_{2-3}$alkyl$R^{33}$ (wherein $X^6$ is as defined in claim 1 and $R^{33}$ represents a group selected from morpholino, 2-oxopyrrolidin-1-yl, pyrrolidin-1-yl, piperidino, piperazin-1-yl and 4-methylpiperazin-1-yl).

7. A quinazoline derivative of the formula 1a:

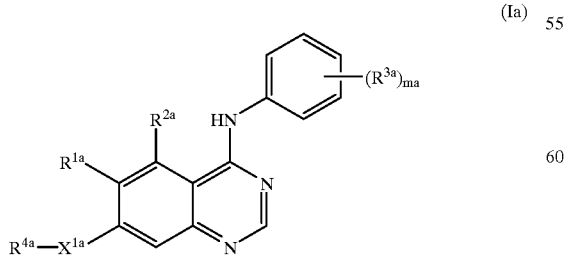

(Ia)

wherein:
$R^{1a}$ is hydrogen or methoxy;

$R^{2a}$ is hydrogen;
the phenyl group bearing $(R^{3a})_{ma}$ is the 4-chloro-2-fluorophenyl group or the 4-bromo-2-fluorophenyl group;
$X^{1a}$ is —O—;
$R^{4a}$ is selected from one of the following nine groups:
1) $C_{1-4}$alkyl$R^{7a}$ (wherein $R^{7a}$ is a group selected from 1,3-dioxolan-2-yl, 1,3-dioxan-2-yl, 1,3-dithiolan-2-yl, 1,3-dithian-2-yl, pyrrolidin-2-yl, pyrrolidin-3-yl, piperidin-2-yl, piperidin-3-yl, piperidin-4-yl, morpholin-2-yl, morpholin-3-yl and piperazin-2-yl which group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl)carbamoyl, $C_{2-3}$alkanoyl and $C_{1-3}$alkoxycarbonyl) or $C_{2-3}$alkyl$R^{8a}$ (wherein $R^{8a}$ is a group selected from imidazolidin-1-yl, pyrrolidin-1-yl and thiomorpholino which group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl)carbamoyl, $C_{2-3}$alkanoyl and $C_{1-3}$alkoxycarbonyl);

2) 1-$R^{9a}$prop-1-en-3-yl, 1-$R^{9a}$but-2-en-4-yl, 1-$R^{9a}$but-1-en-3-yl, 1-$R^{9a}$pent-2-en-4-yl or 2-$R^{9a}$pent-3-en-5-yl (wherein $R^{9a}$ is a 5 or 6 membered saturated heterocyclic group with one or two heteroatoms, selected independently from O, S and N, which heterocyclic group is linked to the alkenyl group through a carbon atom and which heterocyclic group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl)carbamoyl, $C_{2-3}$alkanoyl and $C_{1-3}$alkoxycarbonyl) or 1-$R^{10a}$but-2-en-4-yl, 1-$R^{10a}$pent-2-en-4-yl or 2-$R^{10a}$pent-3-en-5-yl (wherein $R^{10a}$ is a 5 or 6 membered saturated heterocyclic group with one or two heteroatoms, of which one is N and the other is selected independently from O, S and N, which heterocyclic group is linked to the alkenyl group through a nitrogen atom and which heterocyclic group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbomoyl, N,N-di ($C_{1-3}$alkyl)carbamoyl, $C_{1-3}$alkanoyl and $C_{1-3}$alkoxycarbonyl);

3) 1-$R^{11a}$prop-1-yn-3-yl, 1-$R^{11a}$but-2-yn-4-yl, 1-$R^{11a}$but-1-yn-3-yl, 1-$R^{11a}$pent-2-yn-4-yl or 2-$R^{11a}$pent-3-yn-5-yl (wherein $R^{11a}$ is a 5 or 6 membered saturated heterocyclic group with one or two heteroatoms, selected independently from O, S and N, which heterocyclic group is linked to the alkynyl group through a carbon atom and which heterocyclic group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl) carbamoyl, $C_{2-3}$alkanoyl and $C_{1-3}$alkoxycarbonyl) or 1-$R^{12a}$but-2-yn-4-yl, 1-$^{12a}$pent-2-yn-4-yl or 2-$R^{12a}$pent-3-yn-5-yl (wherein $R^{12a}$ is a 5 or 6 membered saturated heterocyclic group with one or two heteroatoms, of which one is N and the other is selected independently from O, S and N, which heterocyclic group is linked to the alkynyl group through a nitrogen atom and which heterocyclic group may bear one or two substituents selected from oxo, hydroxy, halogeno, $C_{1-3}$alkyl, $C_{1-3}$hydroxyalkyl, $C_{1-3}$alkoxy, carbarmoyl, $C_{1-3}$alkylcarbamoyl, N,N-di($C_{1-3}$alkyl)carbamoyl, $C_{1-3}$alkanoyl and $C_{1-3}$alkoxycarbonyl);

4) $C_{2-3}alkylX^{2a}C_{1-3}alkylX^{3a}R^{13a}$ (wherein $X^{2a}$ and $X^{3a}$ which may be the same or different each represents, —O—, —S—, —SO—, —SO$_2$—, —NR$^{14a}$CO—, or —NR$^{15a}$— (wherein R$^{14a}$ and R$^{15a}$ each independently represents hydrogen, $C_{1-2}$alkyl or $C_{1-2}$alkoxyethyl) and R$^{13a}$ represents hydrogen or $C_{1-3}$alkyl);

5) C2-3alkylX$^{4a}$COR$^{16a}$ (wherein X$^{4a}$ represents —O— or —NR$^{17a}$—(wherein R$^{17a}$ represents hydrogen, $C_{1-3}$alkyl or $C_{1-2}$alkoxyethyl) and R$^{16a}$ represents —NR$^{18a}$R$^{19a}$ or —OR$^{20a}$ (wherein R$^{18a}$, R$^{19a}$ and R$^{20a}$ which may be the same or different each represents hydrogen, $C_{1-4}$alkyl or $C_{1-2}$alkoxyethyl));

6) $C_{2-3}alkylX^{5a}R^{21a}$ (wherein X$^{5a}$ represents carbonyl, —O—, —S—, —SO—, —SO$_2$—, —NR$^{22a}$CO—, —NR$^{23a}$SO$_2$—, or —NR$^{24a}$— (wherein R$^{22a}$, R$^{23a}$ and R$^{23a}$ each independently represents hydrogen, $C_{1-2}$alkyl or $C_{1-2}$alkoxyethyl) and R$^{21a}$ represents a group selected from cyclopentyl, cyclohexyl, pyrrolidinyl and piperidinyl which group is linked to X$^{5a}$ through a carbon atom and which group may carry one substituent selected from oxo, hydroxy, halogeno, $C_{1-2}$alkyl, $C_{1-2}$hydroxyalkyl, $C_{1-2}$alkoxy, carbamoyl, $C_{1-2}$alkylcarbamoyl, N,N-di($C_{1-2}$alkyl) carbamoyl, acetyl and $C_{1-2}$alkoxycarbonyl or R$^{21a}$ is $C_{1-3}$alkyl with that proviso that when R$^{21a}$ is $C_{1-3}$alkyl, X$^{5a}$ is —S—, —SO—, —SO$_2$— or —NR$^{23a}$SO$_2$—);

7) $C_{2-3}alkylX^{6a}C_{2-3}alkylR^{25a}$ (wherein X$^{6a}$ represents —O—, —S—, —SO—, —SO$_2$—, —NR$^{26a}$CO—, —NR$^{27a}$SO$_2$— or —NR$^{28a}$-(wherein R$^{26a}$, R$^{27a}$ and R$^{28a}$ each independently represents hydrogen, $C_{1-2}$alkyl or $C_{1-2}$alkoxyethyl) and R$^{25a}$ represents a 5 or 6 membered saturated heterocyclic group with one or two heteratoms selected independently from O, S and N, which heterocyclic group may bear one or two substituents selected from oxo, hydroxy, halogeno, $C_{1-3}$alkyl, $C_{1-3}$hydroxyalkyl, $C_{1-3}$alkoxy, carbamoyl, $C_{1-3}$alkylcarbamoyl, N,N-di($C_{1-3}$alkyl) cabamoyl, $C_{2-3}$alkanoyl, and C1-3allkoxycarbonyl);

8) $C_{2-3}alkylR^{29a}$ (wherein R$^{29a}$ is piperizin-1-yl which bears at least one substituent selected from acetyl, $C_{1-2}$alkoxycarbonyl, $C_{1-2}$hydroxyalkyl and CONR$^{30a}$R$^{31a}$ (wherein R$^{30a}$ and R$^{31a}$ each independently represents hydrogen or $C_{1-2}$alkyl); and 9) $C_{2-3}alkylR^{33a}$ (wherein R$^{33a}$ is morpholino which bears at least one and optionally two substituents selected from oxo, $C_{1-2}$alkyl, $C_{1-2}$hydroxyalkyl, carbamoyl, $C_{1-2}$alkylcarbamoyl, N,N-di($C_{1-2}$alkyl) carbamoyl, acetyl and $C_{1-2}$alkoxycarbonyl);

or a salt thereof.

8. A quinazoline derivative as claimed in claim 1 selected from:

4-(4-chloro-2-fluoroanilino)-7-(1,3-dioxolan-2-ylmethoxy)-6-methoxyquinzoline;

4-(4-chloro-2-fluoroanilino)-6-methoxy-7-(4-morpholinobut-2-en-1-yloxy)quinazoline;

(E)-4-(4-chloro-2-fluoroanilino)-6-methoxy-7-(4-morpholinobut-2-en-1-yloxy)-quinazoline;

4-(4-chloro-2-fluoroanilino)-7-(3-(2,6-dimethylmorpholino)propoxy)-6-methoxyquinazoline;

4-(4-chloro-2-fluoroanilino)-6-methoxy-7-(3-([N-methyl-N-methylsulphonyl]amino)-propoxy) quinazoline;

7-(2-[N-tert-butoxycarbonylamino]ethoxy)-4-(4-chloro-2-fluoroanilino)-6-methoxyquinazoline;

4-(4-bromo-2-fluoroanilino)-6-methoxy-7-(3-([N-methyl-N-methylsulphonyl]amino)-propoxy) quinazoline;

4-(4-chloro-2-fluoroanilino)-6-methoxy-7-2-(2-oxoimidazolidin-1-yl)ethoxy)quinazoline;

4-(4-chloro-2-fluoroanilino)-6-methoxy-7-(2-(3-oxomorpholino)ethoxy)quinazoline;

4-(4-bromo-2-fluoroanilino)-6-methoxy-7-(2-(3-oxomorpholino)ethoxy)quinazoline;

4-(4-chloro-2-fluoroanilino)-6-methoxy-7-(2-thiomorpholinoethoxy)quinazoline;

(S)-4-(4-bromo-2-fluoroanilino)-7-(3-(2-carbamoylpyrrolidin-1-yl)propoxy-6-methoxyquinazoline;

4-(4-chloro-2-fluoroanilino)-6-methoxy-7-(3-(2-oxopyrrolidin-1-yl)propoxy)quinazoline;

4-(4-chloro-2-fluoroanilino)-6-methoxy-7-(2-(2-oxopyrrolidin-1-yl)ethoxy)-quinazoline;

(S)-7-(3-(2-carbamoylpyrrolidin-1-yl)propoxy)-4-(4-chloro-2-fluoroanilino)-6-methoxyquinazoline, 4-(4-chloro-2-fluoroanilino)-6-methoxy-7-(2-(2-morpholinoethoxy)ethoxy)-quinazoline; and 4-(4-bromo-2-fluoroanilino)-6-methoxy-7-(3-(2-oxopyrrolidin-1-yl)propoxy)-quinazoline;

and salts thereof.

9. A quinazoline derivative as claimed in claim 1 selected from:

4-(4-chloro-2-fluoroanilino)-6-methoxy-7-(2-(2-methoxyethoxy)ethoxy)quinazoline;

4-(4-chloro-2-fluoroanilino)-6-methoxy-7-(1-methylpiperidin-3-yl)-methoxyquinazoline;

4-(4-bromo-2-fluoroanilino)-7-3-(1,1-dixothiomorpholino)propoxy)-6-methoxyquinazoline;

4-(4-bromo-2-fluoroanilino)-6-methoxy-7-(2-(2-methoxyethoxy)ethoxy)quinazoline, 4-(4-chloro-2-fluoroanilino)-6-methoxy-7-(2-2-pyrrolidin-1-ylethoxy)ethoxy)-quinazoline;

4-(4-chloro-2-fluoroanilino)-6-methoxy-7-(2-(2-[4-methylpiperazin-1-yl]ethoxy)-ethoxy)quinazoline;

4-(4-chloro-2-fluoroanilino)-6-methoxy-7-(2-([N-methyl-N-methoxyacetyl]amino)-ethoxy)quinazoline; and 4-(4-bromo-2-fluoroanilino)-6-methoxy-7-(2-2-oxopyrrolidin-1-yl)ethoxy)quinazoline;

and salts thereof.

10. A quinazoline derivative as claimed in claim 1 selected from:

(E)-4-(4-chloro-2-fluoroanilino)-6-methoxy-7-(4-(pyrrolidin-1-yl)but-2-en-1-yloxy)-quinazoline;

4-(4-chloro-2-fluoroanilino)-6-methoxy-7-(3-(methylsulphonyl)propoxy)quinazoline;

(S)-4-4-chloro-2-fluoroanilino)-6-methoxy-7-(1-methylpiperidin-3-yl)-methoxyquinazoline; and (R)-4-(4-chloro-2-fluoroanilino)-6-methoxy-7-(1-methylpiperidin-3-yl)-methoxyquinazoline;

and salts thereof.

11. A quinazoline derivative as claimed in claim 1 selected from:

4-(4-chloro-2-fluoroanilino)-6-methoxy-7-(3-(methylsulphonyl)propoxy)quinazoline;

and salts thereof.

12. A quinazoline derivative as claimed in any one of claims 1 and 7–11 in the form of pharmaceutically acceptable salt.

13. A quinazoline derivative as claimed in claim 1 or claim 2 wherein $R^1$ represents methoxy.

14. A quinazoline derivative as claimed in claim 1 or claim 2 wherein m is 2.

15. A quinazoline derivative as claimed in claim 1 or claim 2 wherein the phenyl group bearing $(R^3)m$ is the 4-chloro-2-fluorophenyl group or the 4-bromo-2-fluorophenyl group.

16. A quinazoline derivative as claimed in claim 1 or claim 2 wherein $R^4$ is selected from one of the following six groups:
  1) $C_{1-3}$alkyl$R^{12}$ (wherein $R^{12}$ is 1,3-dioxolan-2-yl, 1,3-dioxan-2-yl, 1,3dithiolan-2-yl, 1,3-dithian-2-yl, pyrrolidin-2-yl, pyrrolidin-3-yl, piperidin-2-yl, piperidin-3-yl, piperidin-4-yl, 1-methylpiperidin-2-yl, 1-methylpiperidin-3-yl, 1-methylpiperidin-4- yl, 1-methylpyrrolidin-2-yl, 1-methylpyrrolidin-3-yl, piperazin-2-yl, 1-methylpiperazine-2-yl, 4-methylpiperazin-2-yl, 1,4-dimethylpiperazin-2-yl, morpholin-2-yl, morpholin-3-yl, 4-methylmorpholin-2-yl or 4-methylmorpholin-3- yl) or $C_{2-3}$alkyl$R^{45}$ (wherein $R^{45}$ is pyrrolidin-1-yl, thiomorpholino, 1,1-dioxothiomorpholino, 2-oxopyrrolidin-1-yl, 2-(N-methylcarbamoyl)pyrrolidin-1-yl, 2-(N,N-dimethylcarbamoyl)pyrrolidin-1-yl, 2-carbamoylpyrrolidin-1yl, 2- oxoimidazolidin-1-yl or 3-methyl-2-oxoimidazolidin-1-yl);
  2) 1-$R^{50}$but-2-en-4-yl (wherein $R^{50}$ is 2-oxoimidazolidin-1-yl, 1,3-dioxolan-2-yl, 1,3- dioxan-2-yl, 1,3-dithiolan-2-yl, 1,3-dithian-2-yl, piperidin-4-yl, 1-methylpiperidin-4- yl, pyrrolidin-1-yl, 1-methylpyrrolidin-3-yl, piperazin-1-yl, morpholino, thiomorpholino, 4-methylpiperazin-1-yl, piperidino or 3-methyl-2-oxoimidazolidin- 1-yl);
  3) 1-$R^{51}$but-2-yn-4-yl (wherein $R^{51}$ is 2-oxoimidazolidin-1-yl, 1,3-dioxolan-2-yl, 1,3- dioxan-2-yl, 1,3-dithiolan-2-yl, 1,3-dithian-2-yl, piperidin-4-yl, 1-methylpiperidin-4- yl, pyrrolidin-1-yl, 1-methylpyrrolidin-3-yl, piperazin-1-yl, morpholino, thiomorpholino, 4-methylpiperazin-1-yl, piperidino or 3-methyl-2-oxoimidazolidin- 1-yl);
  4) $C_{2-3}$alkyl$X^2C_{1-3}$alkyl$X^3R^{16}$ (wherein $X^2$ and $X^3$ are as defined in claim 17 and $R^{16}$ represents hydrogen or $C_{1-3}$alkyl);
  5) $C_{2-3}$alkyl$X^5R^{27}$ (wherein $R^{27}$ is $C_{1-2}$ alkyl and $X^5$ is -S-, -SO-, -SO$_2$-, -SO$_2$NR$^{30}$-or- NR$^{31}$SO$_2$-(wherein $R^{30}$ and $R^{31}$ are as defined in claim 1)); and
  6) $C_{2-3}$alkyl$X^6C_{2-3}$alkyl$R^{33}$ (wherein $X^6$ is as defined in claim 1 and $R^{33}$ represents a group selected from pyrrolidin-1-yl, 4-methylpiperazin-1-yl and morpholino).

17. A quinazoline derivative of the formula I:

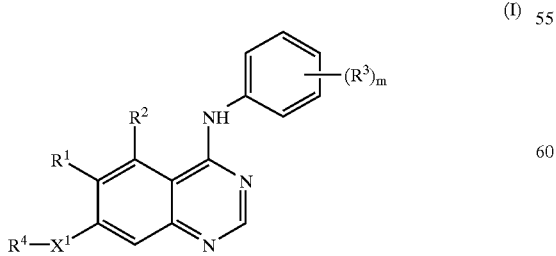

(I)

wherein:
m is an integer from 1 to 2;

$R^1$ represents hydrogen, hydroxy, halogeno, nitro, trifuloromethyl, eyano, $C_{1-3}$alkyl, $C_{1-3}$alkoxy, $C_{1-3}$alkylthio, or -NR$^5$R$^6$ (wherein $R^5$and $R^6$, which may be the same or different, each represents hydrogen or $C_{1-3}$alkyl);

$R_2$ represents hydrogen, hydroxy, halageno, methoxy, amino or nitro;

$R_3$ represents hydroxy, halogeno, $C_{1-3}$alkyl, $C_{1-3}$alkoxy, $C_{1-3}$alkanoyloxy, trifluoromethyl, cyano, amino or nitro;

$X^1$ represents -O-;

$R^4$ is selected from one of the following seven groups:
  1) $C_{1-5}$alkyl$R^{12}$ (wherein $R^{12}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy) or $C_{1-5}$alkyl$R^{13}$ (wherein $R^{13}$ is a group selected from pyrrolidin-1-yl, imidazolidin-1-yl and thiomorpholino, which group may bear one or two substituents selected from oxo, hydroxy, halogeno, $C_{1-4}$alkyl, $C_{1-4}$hydroxyalkyl and $C_{1-4}$alkoxy);
  2) $C_{2-5alkenyl}R^{14}$ (wherein $R^{14}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroyalkyl and $C_{1-4}$alkoxy);
  3) $C_{2-5}$alkynyl$R^{15}$ (wherein $R^{15}$ is a 5 or 6 membered saturated heterocyclic group with one or two heteroatoms, selected independently from O, S and N, which heterocyclic group may bear one or two substituents selected from oxo, hydroxy halogeno, $C_{1-4}$alkyl, $C_{1-4}$hydroxyalkyl and $C_{1-4}$alkoxy);
  4) $C_{1-5}$alkyl$X^2C_{1-5}$alkyl$X^3R^{16}$ (wherein $X^2$ and $X^3$ which may be the same or different are each -O-, -S-, -SO-, -SO$_2$-, -NR$^{17}$CO-, -CONR$^{18-}$, -$^{SO}$$_2$NR$^{19}$-, -NR$^{20}$SO- or -NR$^{21}$- (wherein $R^{17}$, $R^{18}$, $R^{19}$, $R^{20}$ and $R^{21}$ each independetly represents hydrogen, $C_{1-3}$alkyl or $C_{1-3}$alkoxy$C_{2-3}$alkyl) and $R^{16}$ represents hydrogen or $C_{1-3}$alkyl);
  5) $C_{1-5}$alkyl$X^4$COR$^{22}$ (wherein $X^4$ represents -O- or -NR$^{23}$-(wherein $R^{23}$ represents hydrogen, $C_{1-3}$alkyl or $C_{1-3}$alkoxy$C_{2-3}$alkyl) and $R^{22}$ represents -NR$^{24}$R$^{25}$ or -OR$^{26}$ (wherein $R^{24}$, $R^{25}$ and $R^{26}$ which may be the same or different each represents hydrogen, $C_{1-4}$alkyl or $C_{1-3}$alkoxy$C_{2-3}$alkyl));
  6) $C_{1-5}$alkyl$X^5R^{27}$ (wherein $X^5$ represents -O-, -S-, -SO$_2$-, -OCO-, -NR$^{28}$CO-, -CONR$^{29}$-, -SO$_2$NR$^{30}$-, -NR$^{31}$SO$_2$- or -NR$^{32}$-(wherein $R^{28}$, $R^{29}$, $R^{30}$, $R^{31}$ and $R^{32}$ each independently represents hydrogen, $C_{1-3}$alkyl or $C_{1-3}$alkoxy$C_{2-3}$alkyl) and $R^{27}$ represents cyclopentyl, cyclohexyl or a 5 or 6 membered saturated heterocyclic group with one or two heteroatoms, selected independently from O, S and N, which cyclopentyl, cyclohexyl or heterocyclic group may bear one or two substituents selected from oxo, hydroxy, halogeno, $C_{1-4}$alkyl, $C_{1-4}$hydroxyalkyl and $C_{1-4}$alkoxy; and
  7) $C_{1-3}$alkoxy$C_{2-4}$alkyl or $C_{1-4}$alkyl;
with the proviso that when $R^4$ is selected from group 7) $R^1$ and/or $R^2$ is/are nitro or at least one $R^3$ is $C_{1-3}$alkanoyloxy;
and salts thereof.

18. A quinazoline derivative as claimed in claim 17 wherein $R^1$ represents methoxy.

19. A quinazoline derivative as claimed in 17 or claim 18 wherein $R^2$ represents hydrogen.

20. A quinazoline derivative as claimed in claim 17 or claim 18 wherein the phenyl group bearing $(R^3)m$ is of the formula II:

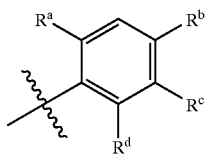

(II)

wherein:

$R^a$ represents hydrogen, methyl, fluoro or chloro;

$R^b$ represents hydrogen, methyl, methoxy, bromo, fluoro or chloro;

$R^c$ represents hydrogen or hydroxy;

$R^d$ represents hydrogen, fluoro or chloro.

21. A process for the preparation of a quinazoline derivative of formula I or salt thereof (as defined in claim 1) which comprises:

(a) the reaction of a compound of the formula III:

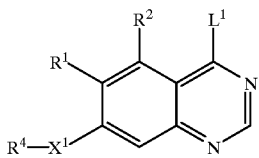

(III)

(wherein $R^1$, $R^2$, $X^1$ and $R^4$ are as defined in claim 1 and $L^1$ is a displaceble moiety), with a compound of the formula IV:

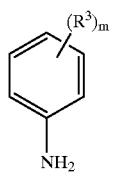

(IV)

(wherein $R^3$ and m are as defined in claim 1) whereby to obtain compounds of the formula I and salts thereof;

(b) for the preperation of compounds of formula I and salts thereof in which the group of formula IIa:

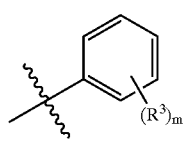

(IIa)

(wherein $R^3$ and m are as defined in claim 1) represents a phenyl group carrying one or more hydroxy groups, the deprotection of a compound of formula V:

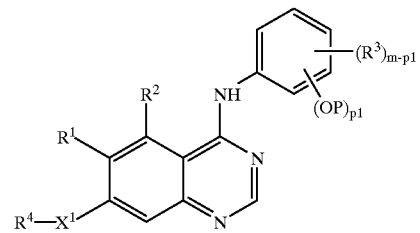

(V)

(wherein $X^1$, m, $R^1$, $R^2$, $R^3$ and $R^4$ are as defined in claim 1, P represents a phenolic hydroxy protecting group and p1 is an integer from 1 to 5 equal to the number of protected hydroxy groups and such that m-p1 is equal to the number of $R^3$ substituents which are not protected hydroxy);

(c) for the preparation of those compounds of formula I and salts thereof wherein the substituent $X^1$ is —O—, the reaction of a compound of the formula VI:

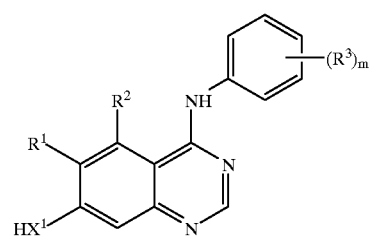

(VI)

(wherein $X^1$, $R^1$, $R^2$ and $R^3$ are as defined in claim 1) with a compound of formula VII:

$R^4$—$L^1$ (VII)

(wherein $R^{14}$ is as defined im claim 1 and $L^1$ is as defined herein);

(d) the reaction of a compound of the formula VII:

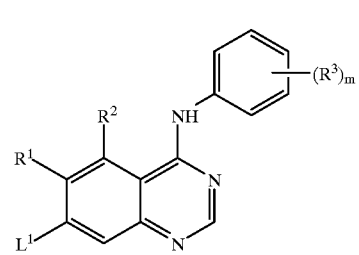

(VIII)

with a compound of the formula IX:

$R^4$—$X^1$—H (IX)

(wherein $R^1$, $R^2$, $R^3$, $R^4$, m and $X^1$ are as defined in claim 1 and $L^1$ is as defined herein);

(e) for the preparation of compounds of formula I and salts thereof wherein $R^4$ is $C_{1-5}$alkyl$R^{53}$, wherein $R^{53}$ is selected from one of the following three groups:

1) $X^7R^{27}$ (wherein $X^7$ represents —O—, —S—, —SO$_2$—, —NR$^{54}$CO—, —NR$^{55}$SO$_2$— or —NR$^{56}$— (wherein $R^{54}$, $R^{55}$ and $R^{56}$ each independently represents hydrogen, $C_{1-3}$alkyl or $C_{1-3}$alkoxy$C_{2-3}$alkyl) and $R^{27}$ is as defined in claim 1);

2) $X^8C_{1-5}$alkyl$X^3R^{16}$ (wherein $X^8$ represents —O—, —S—, —SO$_{12}$—, —NR$^{57}$CO—, —NR$^{58}$SO$_2$— or —NR$^{59}$— (wherein $R^{57}$, $R^{58}$ and $R^{59}$ each independently represents hydrogen, $C_{1-3}$alkyl or $C_{1-3}$alkoxy$C_{2-3}$alkyl) and $X^3$ and $R^{16}$ are as defined in claim 1); and 3) $X^9C_{1-5}$alkyl$R^{33}$ (wherein $X^9$ represents —O—, —S—, —SO$_2$—, —NR$^{60}$CO—NR$^{61}$SO$_2$— or —NR$^{62}$— (wherein $R^{60}$, $R^{61}$ and $R^{62}$ each independently represent hydrogen, $C_{1-3}$alkyl or $C_{1-3}$alkoxy$C_{2-3}$alkyl) and $R^{33}$ is as defined in claim 1);

the reaction of a compound of the formula X:

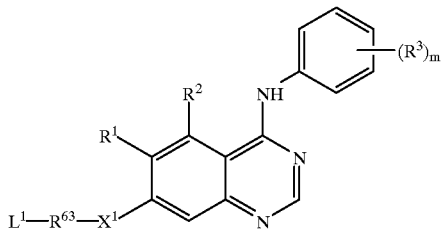

(X)

(wherein $X^1$, $R^1$, $R^2$, $R^3$ and m are as defined in claim 1, $L^1$ is as defined herein and $R^{63}$ is $C_{1-5}$alkyl) with a compound of the formula XI:

$R^{53}$—H (XI)

(wherein $R^{53}$ is as defined herein) to give a compound of the formula I;

(f) for the preparation of compounds of the formula I wherein $R^4$ is $C_{2-5}$alkyl$R^{45}$, (wherein $R^{45}$ is a group selected from imidazolidin-1-yl, pyrrolidin-1-yl and thiomorpholino, which group may bear one or two substituents selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl), the reaction of a compound of formula X (wherein $R^{63}$ is $C_{2-5}$alkyl) with a compound of the formula XIa:

$R^{45}$—H (XIa)

(wherein $R^{45}$ is as defined herein) to give a compound of the formula I;

(g) for the preparation of those compounds of the formula I and salts thereof wherein the substituent $R^1$ is represented by —NR$^5$R$^6$ where one or both of $R^5$ and $R^6$ are $C_{1-3}$alkyl, the reaction of compounds of formula I wherein the substituent $R^1$ is an amino group with an alkylating agent;

(h) for the prepation of compounds of formula I and salts thereof wherein one or more of the substituents $R^1$, $R^2$ or $R^3$ is an amino group, the reduction of a corresponding compound of formula I wherein the substituent(s) at the corresponding position(s) of the quinazoline and/or aniline ring is/are a nitro group(s):

and when a pharmaceutically acceptable salt of a quinazoline derivative of formula I is required, reaction of the compound obtained with an acid or base whereby to obtain the desired pharmaceutically acceptable salt.

22. A pharmaceutical composition which comprises as active ingredient a compound of formula I as defined in any one of claims 1 and 7–11 or a pharmaceutically acceptable salt thereof, in association with a pharmaceutically acceptable excipient or carrier.

23. A method for producing an antiangiogenic and/or vascular permeability reducing effect in a warm-blooded animal in need of such treatment which comprises administering to said animal an effective amount of a compound of formula I or a pharmaceutically acceptable salt thereof as defined in any one of claims 1 and 7–11.

* * * * *